United States Patent
Peng et al.

(10) Patent No.: US 9,637,484 B2
(45) Date of Patent: May 2, 2017

(54) CYCLOALKYL ACID DERIVATIVE, PREPARATION METHOD THEREOF, AND PHARMACEUTICAL APPLICATION THEREOF

(71) Applicants: Shanghai Hengrui Pharmaceutical Co., Ltd., Shanghai (CN); Jiangsu Hengrui Medicine Co., Ltd., Lianyungang, Jiangsu (CN)

(72) Inventors: Jianbiao Peng, Shanghai (CN); Piaoyang Sun, Jiangsu (CN); Jiong Lan, Shanghai (CN); Chunyan Gu, Shanghai (CN); Xiaotao Li, Shanghai (CN); Bonian Liu, Shanghai (CN); Chunzhou Han, Shanghai (CN); Qiyue Hu, Shanghai (CN); Fangfang Jin, Shanghai (CN); Qing Dong, Shanghai (CN); Guoqing Cao, Shanghai (CN)

(73) Assignees: SHANGHAI HENGRUI PHARMACEUTICAL CO., LTD., Shanghai (CN); JIANGSU HENGRUI MEDICINE CO., LTD., Lianyungang, Jiangsu (CN)

( * ) Notice: Subject to any disclaimer, the term of this patent is extended or adjusted under 35 U.S.C. 154(b) by 0 days.

(21) Appl. No.: 14/889,563

(22) PCT Filed: Apr. 29, 2014

(86) PCT No.: PCT/CN2014/076447
§ 371 (c)(1),
(2) Date: Nov. 6, 2015

(87) PCT Pub. No.: WO2014/183555
PCT Pub. Date: Nov. 20, 2014

(65) Prior Publication Data
US 2016/0108035 A1    Apr. 21, 2016

(30) Foreign Application Priority Data

May 13, 2013 (CN) .......................... 2013 1 0174990

(51) Int. Cl.
| | |
|---|---|
| *C07D 471/04* | (2006.01) |
| *A61K 31/47* | (2006.01) |
| *C07D 215/36* | (2006.01) |
| *C07D 215/38* | (2006.01) |
| *C07D 215/48* | (2006.01) |
| *C07C 323/62* | (2006.01) |
| *A61K 31/277* | (2006.01) |
| *A61K 31/4375* | (2006.01) |
| *A61K 45/06* | (2006.01) |
| *C07C 321/28* | (2006.01) |

(52) U.S. Cl.
CPC .......... *C07D 471/04* (2013.01); *A61K 31/277* (2013.01); *A61K 31/4375* (2013.01); *A61K 31/47* (2013.01); *A61K 45/06* (2013.01); *C07C 321/28* (2013.01); *C07C 323/62* (2013.01); *C07D 215/36* (2013.01); *C07D 215/38* (2013.01); *C07D 215/48* (2013.01); *C07C 2101/04* (2013.01)

(58) Field of Classification Search
CPC .. C07D 215/48; C07D 215/38; C07D 215/36; C07D 471/04; A61K 45/06; A61K 31/47; A61K 31/4375; A61K 31/277
See application file for complete search history.

(56) References Cited

U.S. PATENT DOCUMENTS 8,084,483 B2    12/2011  Quart et al.

FOREIGN PATENT DOCUMENTS

| EP | 1820515 A1 | 8/2007 |
|---|---|---|
| WO | 03087098 A1 | 10/2003 |
| WO | 2006057460 A1 | 6/2006 |
| WO | 2006132739 A2 | 12/2006 |

(Continued)

OTHER PUBLICATIONS

John, CA 25:8708, abstract only of Journal fuer Praktische Chemie (Leipzig), 1930, vol. 128, 218-222.*
Sattui,Theragpeutic Advances in Musculoskeletal Disease, 8(4), 145-159, 2016.*
So, J Clin Inves, vol. 120(6), 2010, 1791-1799.*
Tan, Abstract No. 2963, Meeting 2014 ACR/ARHP annual meeting, http://acrabstracts.ort/abstract/the-urat1-uric-acid-transporter-is-important-in-uric-acid-homeostasis-and-its-activity-may-be-altered-in-gout-patients-and-in-drug-induced-hyperuricemia/, 2014.*

(Continued)

*Primary Examiner* — D M Seaman
(74) *Attorney, Agent, or Firm* — Panitch Schwarze Belisario & Nadel LLP

(57) ABSTRACT

Cycloalkyl acid derivatives, a preparation method thereof, and a pharmaceutical application thereof are described. In particular, a cycloalkyl acid derivative represented by general formula (I) and a medical salt thereof, a preparation method thereof, and an application of the cycloalkyl acid derivative and the medical salt thereof as URAT1 inhibitors, and particularly as therapeutic agents for diseases related to an abnormal uric acid level are described, wherein definitions of substituent groups in general formula (I) are the same as the definitions in the specification.

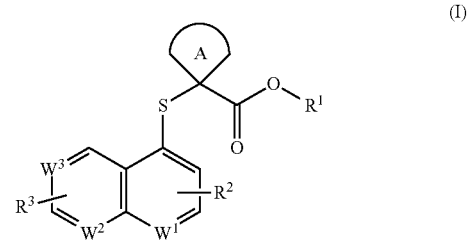

20 Claims, No Drawings

(56) References Cited

FOREIGN PATENT DOCUMENTS

| WO | 2008124083 A2 | 10/2008 |
|---|---|---|
| WO | 2008153129 A1 | 12/2008 |
| WO | 2010044403 A1 | 4/2010 |
| WO | 2011046800 A1 | 4/2011 |
| WO | 2011159839 A2 | 12/2011 |

OTHER PUBLICATIONS

Enomoto et al., "Molecular identification of a renal urate-anion exchanger that regulates blood urate levels," Nature, vol. 417, No. 6887, pp. 447-452 (May 23, 2002).

Iwai et al., "A high prevalence of renal hypouricemia caused by inactive SLC22A12 in Japanese," Kidney International, vol. 66, No. 3, pp. 935-944 (2004).

Taniguchi et al., "A common mutation in an organic anion transporter gene, SLC22A12, is a suppressing factor for the development of gout," Arthritis & Rheumatism, vol. 52, No. 8, pp. 2576-2577 (Aug. 2005).

Graessler et al., "Association of the Human Urate Transporter 1 With Reduced Renal Uric Acid Excretion and Hyperuricemia in a German Caucasian Population," Arthritis & Rheumatism, vol. 54, No. 1, pp. 292-300 (Jan. 2006).

Guan et al., "High-resolution melting analysis for the rapid detection of an intronic single nucleotide polymorphism in SLC22A12 in male patients with primary gout in China," Scand J Rheumatol., vol. 38, No. 4, pp. 276-281 (2009).

Madrid et al., "Synthesis of ring-subsituted 4-aminoquinolines and evaluation of their antimalarial activities," Bioorganic & Medicinal Chemistry Letters, vol. 15, No. 4, pp. 1015-1018 (2005).

Wang et al., "[11C]GSK2126458 and [18F]GSK2126458, the first radiosynthesis of new potential PET agents for imaging of PI3K and mTOR in cancers," Bioorganic & Medicinal Chemistry Letters, vol. 22, No. 4, pp. 1569-1574 (2012).

Sharma et al., "Synthesis and Biological Activity of Substituted Quinolones Derived from 6-Fluoro-3-Carbethoxy-1H-Quinolin-4-One," Indian Journal of Heterocyclic Chemistry, vol. 15, No. 3, pp. 253-258 (2006).

Lan et al., "Synthesis of mono-substituted derivatives of 6-aminoquinoline," Chinese Chemical Letters, vol. 22, No. 3, pp. 253-255 (2011).

Database CA [Online]. Columbus, Ohio, US: Chemical Abstracts Service, RN 1065092-21-8 (Oct. 23, 2008).

Database CA [Online]. Columbus, Ohio, US: Chemical Abstracts Service, RN 1065092-18-3 (Oct. 23, 2008).

International Search Report issued Aug. 4, 2014 in International Application No. PCT/CN2014/076447.

\* cited by examiner

CYCLOALKYL ACID DERIVATIVE, PREPARATION METHOD THEREOF, AND PHARMACEUTICAL APPLICATION THEREOF

CROSS-REFERENCE TO RELATED APPLICATION

This application is a Section 371 of International Application No. PCT/CN2014/076447, filed Apr. 29, 2014, which was published in the Chinese language on Nov. 20, 2014, under International Publication No. WO 2014/183555 A1, and the disclosure of which is incorporated herein by reference.

FIELD OF THE INVENTION

The present invention relates to a novel cycloalkyl acid derivative and a pharmaceutically acceptable salt thereof, a preparation method thereof, and the pharmaceutical composition containing the same, and its use as a URAT1 inhibitor, and particularly as a therapeutic agent for diseases related to an abnormal uric acid level.

BACKGROUND OF THE INVENTION

Uric acid is a metabolite of purine in vivo. Due to the lack of uricase, which degrades uric acid in the human body, uric acid is mainly excreted from the body through the kidney and intestine, wherein the kidney is the major route of uric acid excretion. Transportation of uric acid in the kidney directly regulates the level of serum uric acid. Decreased excretion or increased production of uric acid can lead to hyperuricemia, 90% of which is caused by the decrease of uric acid excretion. Recently, the prevalence of hyperuricemia and gout has increased significantly with the improvement of people's living standard. Hyperuricemia and primary gout show a significant positive correlation with obesity, hyperlipidemia, hypertension, diabetes and atherosclerosis etc. Therefore, hyperuricemia and gout are metabolic diseases seriously harmful to human health, similar to diabetes.

Hyperuricemia refers to a body condition with the concentration of uric acid in the blood beyond the normal range (37° C., serum uric acid content is over 416 μmol/PL (70 mg/PL) in male; over 357 μmol/PL (60 mg/PL) in female). In 2009, hyperuricemia prevalence was 10.0% in the Shanghai area, with 11.1% for males, and 9.4% for females; hyperuricemia prevalence in Beijing was 17.86% among 1120 subjects, with 25.74% for males and 10.52% for females; the prevalence of the Guangzhou area ranked first in the country with 27.9% for males and 12.4% for females, and the total prevalence rate was up to 21.81%.

Gout is a heterogeneous, metabolic disease caused by long-term purine metabolic disorder and/or decreased uric acid excretion. Gout can be divided into primary and secondary types, its clinical features are hyperuricemia, recurrent acute arthritis, and are generally associated with cardiovascular and cerebrovascular diseases, thereby threatening human life. High-risk populations include men and menopausal women; and the peak incidence is 40-50 years old. The prerequisite cause of gout is hyperuricemia, when uric acid content in serum extends beyond the normal range, and urate deposition in tissues can also cause gout histological changes. 5%-12% of hyperuricemia patients eventually developed gout only when they appeared to have the symptoms of urate crystal deposition, arthritis, kidney disease, kidney stone etc.

Physiological and pharmacological studies found a kidney urate transport classic mode: glomerular filtration, renal tubular reabsorption, renal tubular secretion and reabsorption after secretion. Any factor that impacts the aforesaid four processes will impact renal excretion of uric acid. More than 98% of uric acid filtrated by glomerulus can be reabsorpted and then secreted by proximal renal tubule, which is the most important factor that impacts uric acid excretion. Proximal convoluted tubule (also known as proximal tubule curved portion) SI segment is a reabsorption place, 98% to 100% of filtrated uric acid enters into the epithelial cells here via the urate transporter 1 (URAT1) in the brush border membrane of tubular epithelial cells.

URAT1 is also called OAT4L (organic anion transporter 4-like) or urate anion exchanger 1. Human URAT1 (hURAT1), encoded by the SLC22A12 gene (containing 10 exons and 9 introns) on chromosome 11 q 13, has 42% homology with OAT4. Human URAT1 is a complete transmembrane protein of 555 amino acid residues, consisting of 12 transmembrane domains, a —NH2 terminal domain and a —COOH terminal domain located inside the cell. Enomoto et al. (*Nature*. 2002; 417(6887): 447-52) found that hURAT1 had a function of transporting urate, which was time-dependent and saturated. Studies found that SLC22A12 gene carried in renal hypouricemia patients was mutated, thereby losing the ability of encoding URAT1, which suggested that URAT1 was important for uric acid reabsorption in the kidney. Specific mutations of the URAT1 gene sequence of Japanese carrying SLC22A12 heterozygous decreased the serum uric acid concentration and gout incidence. Iwai et al. (*Kidney Int*. 2004; 66(3): 935-44) studied SLC22A12 gene polymorphisms in Japanese population, and found that particular polymorphisms of the gene were related to hypouricemia, and expression in vitro demonstrated that some mutations can lead to loss of the uric-acid-transport function of URAT1. Taniguchi et al. (*Arthritis Rheum*. 2005; 52(8): 2576-2577) found that the G774A mutation of SCL22A12 inhibited gout occurrence, and the serum uric acid level in patients with heterozygous G774A mutation was significantly lower than in healthy people. Graessler et al. (*Arthritis Rheum*. 2006; 54(1): 292-300) reported that an N-terminal gene polymorphism found in Germany's Caucasian population was related to a decrease of renal uric acid excretion. Guan et al. (*Scand J Rheumatol*. 2009; 38(4): 276-81) studied polymorphisms of the sr893006 gene sequence of SLC22A12 in 124 primary gout patients and 168 healthy Chinese male subjects, suggesting that the polymorphism of this gene sequence may be a genetic risk factor for Chinese male patients with hyperuricemia. URAT1 will be a new target for the development of a drug for treating gout and hyperuricemia.

Currently, there are many compounds for treating hyperuricemia and gout in clinical trials and the marketing stage, in which URAT1 specific inhibitors in clinical trials are only lesinurad (phase III) and RDEA-3170 (Phase I) from Ardea Biosciences. Patent applications disclosing URAT1 inhibitors include WO2006057460, WO2008153129, WO2010044403, WO2011046800 and WO2011159839, etc.

In order to achieve better treatment, and to better meet the market demands, we hope to develop a new generation of URAT1 inhibitors with high efficiency and low toxicity. The present disclosure provides new structural URAT1 inhibitors, and it is found that compounds having such structures have good activity, and exhibit excellent decrease of serum uric acid concentration, and treatment effect for hyperuricemia and gout.

SUMMARY OF THE INVENTION

The present invention is directed to provide a compound of formula (I), a tautomer, mesomer, racemate, enantiomer, or diastereomer thereof, or a mixture thereof, or a pharmaceutically acceptable salt thereof:

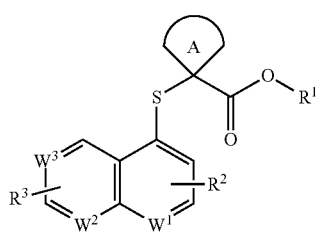

(I)

wherein:

ring A is cycloalkyl, wherein the cycloalkyl is optionally substituted with one or more groups selected from the group consisting of halogen, cyano, nitro, amino, hydroxy, oxo, alkyl, haloalkyl, hydroxyalkyl, alkoxy, cycloalkyl, heterocyclyl, aryl, heteroaryl, carboxyl and alkoxycarbonyl;

$W^1$ is N or $CR^a$;
$W^2$ is N or $CR^b$;
$W^3$ is N or $CR^c$;

$R^a$, $R^b$ and $R^c$ are each independently selected from the group consisting of hydrogen, halogen, cyano, nitro, alkyl, alkenyl, alkynyl, cycloalkyl, heterocyclyl, aryl, heteroaryl, —$OR^4$, —$S(O)_mR^4$, —$C(O)R^4$, —$C(O)OR^4$, —$C(O)NR^5R^6$, —$NR^5R^6$ and —$NR^5C(O)R^6$, wherein the alkyl, alkenyl, alkynyl, cycloalkyl, heterocyclyl, aryl and heteroaryl are each independently optionally substituted with one or more groups selected from the group consisting of halogen, cyano, nitro, oxo, alkyl, haloalkyl, hydroxyalkyl, alkenyl, alkynyl, cycloalkyl, heterocyclyl, aryl, heteroaryl, —$OR^4$, —$S(O)_mR^4$, —$C(O)R^4$, —$C(O)OR^4$, —$C(O)NR^5R^6$, —$NR^5R^6$ and —$NR^5C(O)R^6$;

$R^1$ is hydrogen or alkyl;

$R^2$ and $R^3$ are each independently selected from the group consisting of hydrogen, halogen, cyano, nitro, alkyl, haloalkyl and hydroxyalkyl;

$R^4$ is selected from the group consisting of hydrogen, alkyl, halogen, cycloalkyl, heterocyclyl, aryl or heteroaryl, wherein the alkyl, cycloalkyl, heterocyclyl, aryl and heteroaryl are each independently optionally substituted with one or more groups selected from the group consisting of halogen, cyano, nitro, hydroxy, oxo, alkyl, haloalkyl, hydroxyalkyl, alkoxy, cycloalkyl, heterocyclyl, aryl, heteroaryl, carboxyl, alkoxycarbonyl, —$C(O)NR^5R^6$, —$NR^5R^6$ and —$NR^5C(O)R^6$;

$R^5$ and $R^6$ are each independently selected from the group consisting of hydrogen, alkyl, cycloalkyl, heterocyclyl, aryl and heteroaryl, wherein the alkyl, cycloalkyl, heterocyclyl, aryl and heteroaryl are each independently optionally substituted with one or more groups selected from the group consisting of halogen, cyano, nitro, amino, hydroxy, oxo, alkyl, haloalkyl, hydroxyalkyl, alkoxy, cycloalkyl, heterocyclyl, aryl, heteroaryl, carboxyl and alkoxycarbonyl; and m is 0, 1, or 2.

In a preferred embodiment of the invention, in the compound of formula (I) or a tautomer, mesomer, racemate, enantiomer, or diastereomer thereof, or mixture thereof, or a pharmaceutically acceptable salt thereof, ring A is cycloalkyl, preferably $C_{3-6}$ cycloalkyl, more preferably cyclopropyl, cyclobutyl or cyclopentyl, and most preferably cyclobutyl.

In another preferred embodiment of the invention, in the compound of formula (I) or a tautomer, mesomer, racemate, enantiomer, or diastereomer thereof, or mixture thereof, or a pharmaceutically acceptable salt thereof, $R^c$ is selected from the group consisting of hydrogen, halogen, cyano, alkyl, cycloalkyl, aryl, —$OR^4$, —$NR^5R^6$ and —$NR^5C(O)R^6$, wherein the alkyl, cycloalkyl and aryl are each independently optionally substituted with one or more groups selected from the group consisting of halogen, cyano, nitro, oxo, alkyl, haloalkyl, hydroxyalkyl, cycloalkyl and heterocyclyl; and $R^4$ to $R^6$ are as defined in the above formula (I).

In another preferred embodiment of the invention, in the compound of formula (I) or a tautomer, mesomer, racemate, enantiomer, or diastereomer thereof, or mixture thereof, or a pharmaceutically acceptable salt thereof, $R^c$ is selected from the group consisting of hydrogen, halogen, alkyl and haloalkyl.

In another preferred embodiment of the invention, in the compound of formula (I) or a tautomer, mesomer, racemate, enantiomer, or diastereomer thereof, or mixture thereof, or a pharmaceutically acceptable salt thereof, $W^2$ is CH.

In another preferred embodiment of the invention, in the compound of formula (I) or a tautomer, mesomer, racemate, enantiomer, or diastereomer thereof, or mixture thereof, or a pharmaceutically acceptable salt thereof, $R^1$ is hydrogen.

In another preferred embodiment of the invention, in the compound of formula (I) or a tautomer, mesomer, racemate, enantiomer, or diastereomer thereof, or mixture thereof, or a pharmaceutically acceptable salt thereof, $R^1$ is alkyl.

In another preferred embodiment of the invention, in the compound of formula (I) or a tautomer, mesomer, racemate, enantiomer, or diastereomer thereof, or mixture thereof, or a pharmaceutically acceptable salt thereof, $R^2$ is hydrogen.

In another preferred embodiment of the invention, in the compound of formula (I) or a tautomer, mesomer, racemate, enantiomer, or diastereomer thereof, or mixture thereof, or a pharmaceutically acceptable salt thereof, $R^3$ is hydrogen or halogen.

In another preferred embodiment of the invention, the compound of formula (I) or a tautomer, mesomer, racemate, enantiomer, or diastereomer thereof, or mixture thereof, or a pharmaceutically acceptable salt thereof, is a compound of formula (II) or a tautomer, mesomer, racemate, enantiomer, or diastereomer thereof, or mixture thereof, or a pharmaceutically acceptable salt thereof:

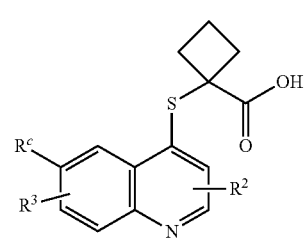

(II)

wherein:

$R^c$, $R^2$, and $R^3$ are as defined in formula (I).

In another preferred embodiment of the invention, the compound of formula (I) or a tautomer, mesomer, racemate, enantiomer, or diastereomer thereof, or mixture thereof, or a pharmaceutically acceptable salt thereof, is a compound of formula (III) or a tautomer, mesomer, racemate, enantiomer, or diastereomer thereof, or mixture thereof, or a pharmaceutically acceptable salt thereof:

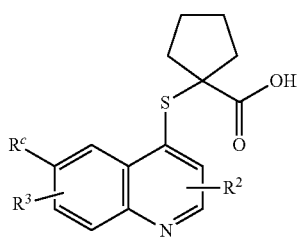

(III)

wherein:

R$^c$, R$^2$, and R$^3$ are as defined in formula (I).

In another preferred embodiment of the invention, the compound of formula (I) or a tautomer, mesomer, racemate, enantiomer, or diastereomer thereof, or mixture thereof, or a pharmaceutically acceptable salt thereof, is a compound of formula (IV) or a tautomer, mesomer, racemate, enantiomer, or diastereomer thereof, or mixture thereof, or a pharmaceutically acceptable salt thereof:

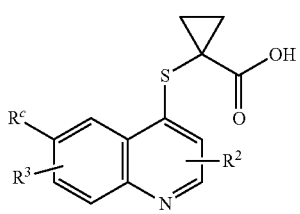

(IV)

wherein:

R$^c$, R$^2$, and R$^3$ are as defined in formula (I).

Typical compounds of the present invention include, but are not limited to the following:

| Example No. | Structure and Name |
|---|---|
| 1 | 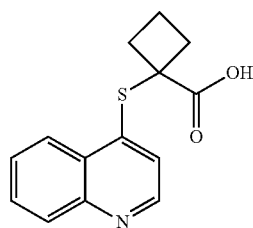<br>1-(quinolin-4-ylthio)cyclo-butanecarboxylic acid |
| 2 | 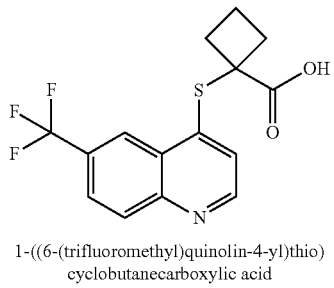 [SMILES: O=C(O)C1(Sc2ccnc3ccc(C(F)(F)F)cc23)CCC1]<br>1-((6-(trifluoromethyl)quinolin-4-yl)thio)cyclobutanecarboxylic acid |
| 3 | 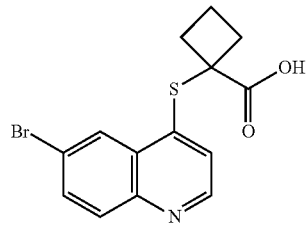<br>1-((6-bromoquinolin-4-yl)thio)cyclo-butanecarboxylic acid |
| 4 | 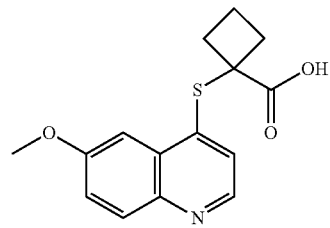<br>1-((6-methoxyquinolin-4-yl)thio)cyclo-butanecarboxylic acid |
| 5 | 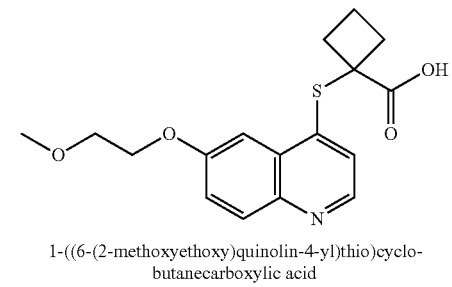 [SMILES: COCCOc1ccc2nccc(SC3(C(=O)O)CCC3)c2c1]<br>1-((6-(2-methoxyethoxy)quinolin-4-yl)thio)cyclo-butanecarboxylic acid |
| 6 | 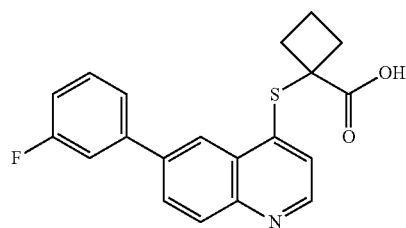<br>1-((6-(3-fluorophenyl)quinolin-4-yl)thio)cyclo-butanecarboxylic acid |

| Example No. | Structure and Name |
|---|---|
| 7 | 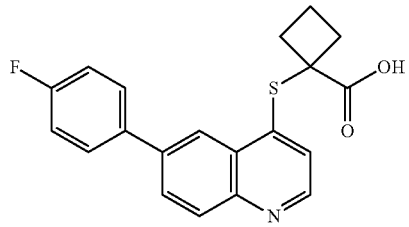<br>1-((6-(4-fluorophenyl)quinolin-4-yl)thio)cyclo-butanecarboxylic acid |
| 8 | 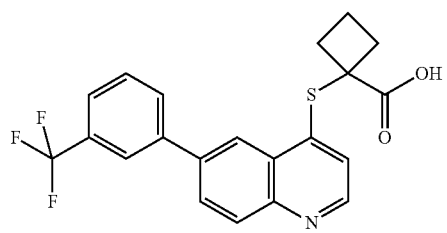<br>1-((6-(3-trifluoromethyl)phenyl)quinolin-4-yl)thio)cyclobutanecarboxylic acid |
| 9 | 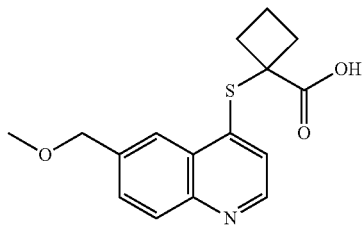<br>1-((6-(methoxymethyl)quinolin-4-yl)thio)cyclobutanecarboxylic acid |
| 10 | 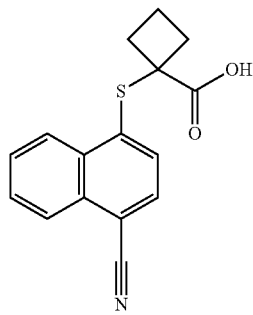<br>1-((4-cyanonaphthalen-1-yl)thio)cyclobutanecarboxylic acid |
| 11 | 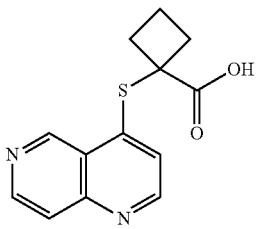<br>1-((1,6-naphthyridin-4-yl)thio)cyclobutanecarboxylic acid |
| 12 | 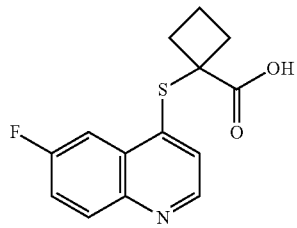<br>1-((6-fluoroquinolin-4-yl)thio)cyclobutanecarboxylic acid |
| 13 | 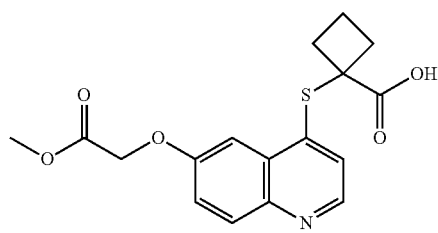<br>1-((6-(2-methoxy-2-oxoethoxy)quinolin-4-yl)thio)cyclobutanecarboxylic acid |
| 14 | 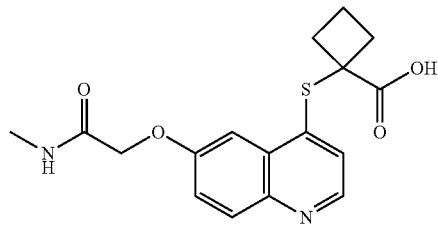<br>1-((6-(2-(methylamino)2-oxoethoxy)quinolin-4-yl)thio)cyclobutanecarboxylic acid |
| 15 | 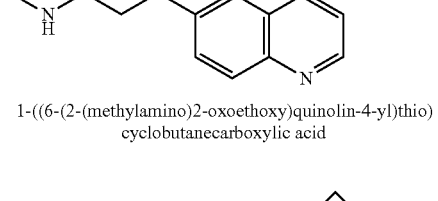<br>1-((6-(2-hydroxyethoxy)quinolin-4-yl)thio)cyclobutanecarboxylic acid |
| 16 | 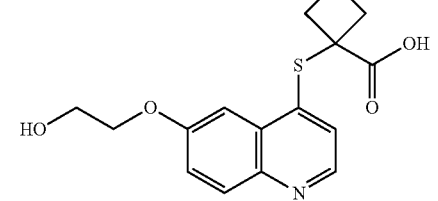<br>1-((6-acetamidoquinolin-4-yl)thio)cyclo-butanecarboxylic acid |

-continued

| Example No. | Structure and Name |
|---|---|
| 17 | 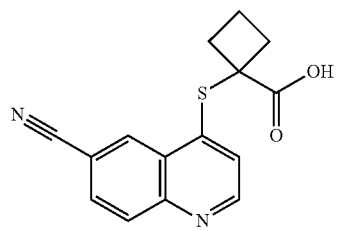<br>1-((6-cyanoquinolin-4-yl)thio)cyclo-butanecarboxylic acid |
| 18 | 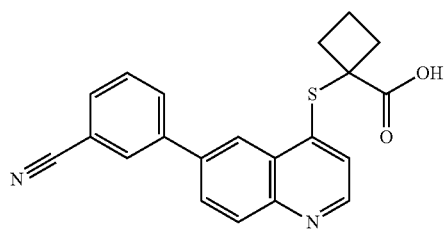<br>1-((6-(3-cyanophenyl)quinolin-4-yl)thio)cyclobutane-carboxylic acid |
| 19 | 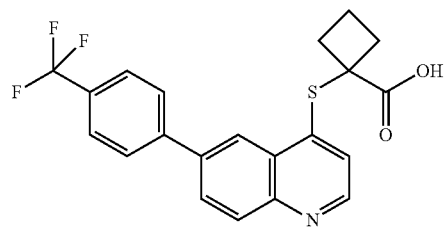<br>1-((6-(4-(trifluoromethyl)phenyl)quinolin-4-yl)thio)cyclobutanecarboxylic acid |
| 20 | 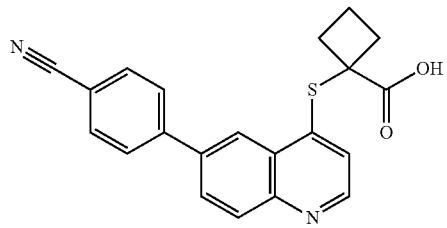<br>1-((6-(4-cyanophenyl)quinolin-4-yl)thio)cyclobutane-carboxylic acid |
| 21 | 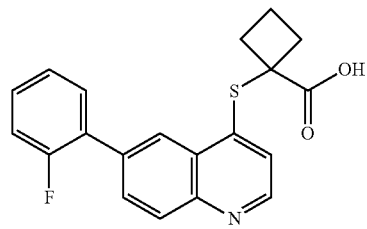<br>1-((6-(2-fluorophenyl)quinolin-4-yl)thio)cyclo-butanecarboxylic acid |

-continued

| Example No. | Structure and Name |
|---|---|
| 22 | 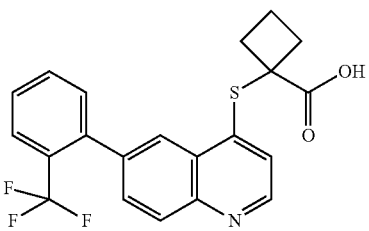<br>1-((6-(2-(trifluoromethyl)phenyl)quinolin-4-yl)thio)cyclobutanecarboxylic acid |
| 23 | 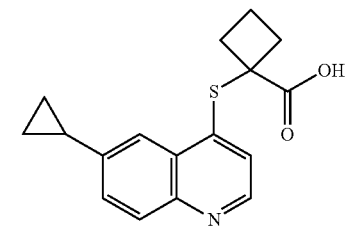<br>1-((6-cyclopropylquinolin-4-yl)thio)cyclobutanecarboxylic acid |
| 24 | 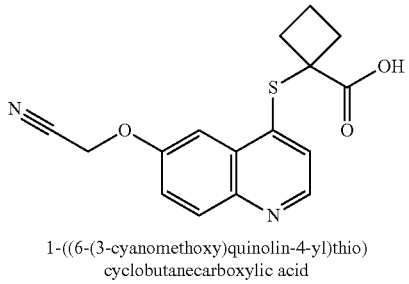 [SMILES: N#CCOc1ccc2nccc(SC3(C(=O)O)CCC3)c2c1]<br>1-((6-(3-cyanomethoxy)quinolin-4-yl)thio)cyclobutanecarboxylic acid |
| 25 | 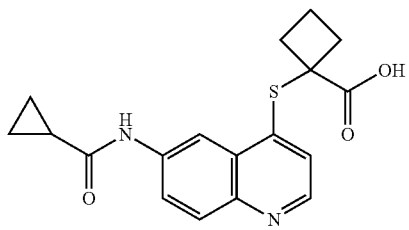<br>1-((6-(cyclopropanecarboxamido)quinolin-4-yl)thio)cyclobutanecarboxylic acid |
| 26 | 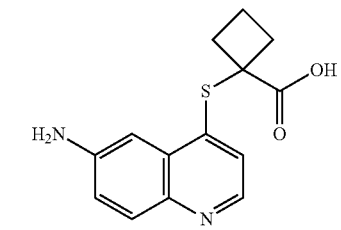<br>1-((6-aminoquinolin-4-yl)thio)cyclo-butanecarboxylic acid |

-continued

| Example No. | Structure and Name |
|---|---|
| 27 | 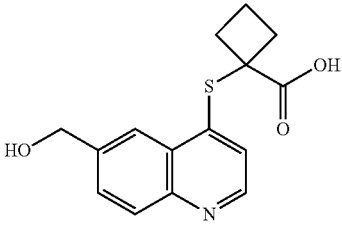<br>1-((6-(hydroxymethyl)quinolin-4-yl)thio)cyclobutanecarboxylic acid |
| 28 | 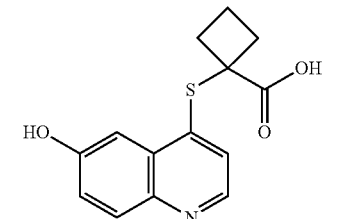<br>1-((6-hydroxyquinolin-4-yl)thio)cyclobutanecarboxylic acid |
| 29 | 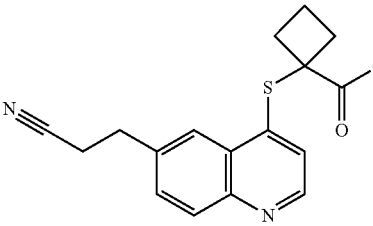<br>1-((6-(2-cyanoethyl)quinolin-4-yl)thio)cyclobutanecarboxylic acid |
| 30 | 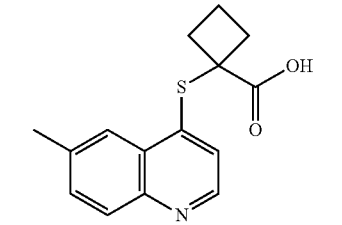<br>1-((6-methylquinolin-4-yl)thio)cyclobutanecarboxylic acid |
| 31 | 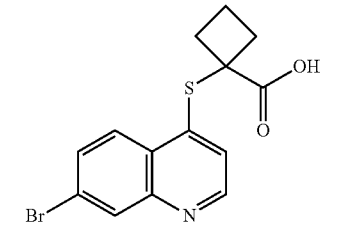<br>1-((7-bromoquinolin-4-yl)thio)cyclobutanecarboxylic acid |

-continued

| Example No. | Structure and Name |
|---|---|
| 32 | 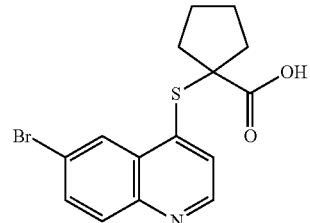<br>1-((6-bromoquinolin-4-yl)thio)cyclopentanecarboxylic acid |
| 33 | 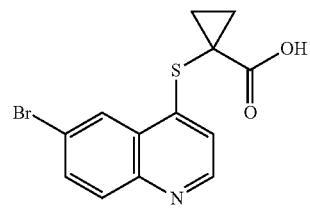<br>1-((6-bromoquinolin-4-yl)thio)cyclopropanecarboxylic acid |
| 1b | 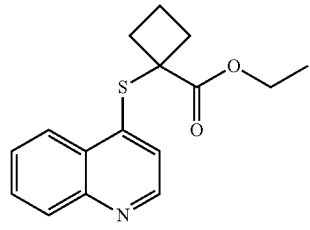<br>1b<br>ethyl 1-(quinolin-4-ylthio)cyclobutanecarboxylate |
| 2d | 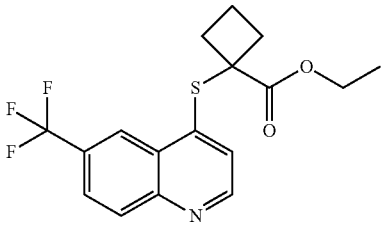<br>2d<br>ethyl 1-((6-(trifluoromethyl)quinolin-4-yl)thio)cyclobutanecarboxylate |
| 3c | 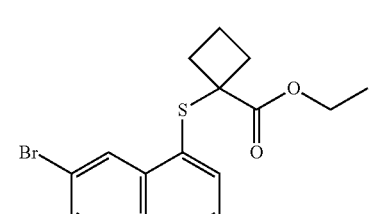<br>3c<br>ethyl 1-((6-bromoquinolin-4-yl)thio)cyclobutanecarboxylate |

| Example No. | Structure and Name |
|---|---|
| 4c | 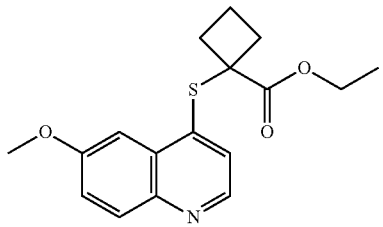
4c
ethyl 1-((6-methoxyquinolin-4-yl)thio)cyclobutanecarboxylate |
| 5a | 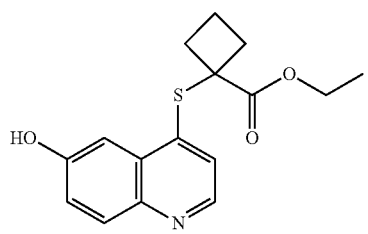
5a
ethyl 1-((6-hydroxyquinolin-4-yl)thio)cyclobutanecarboxylate |
| 5b | 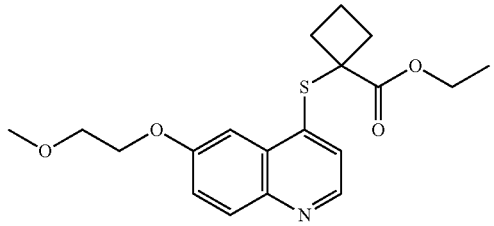
5b
ethyl 1-((6-(2-methoxyethoxy)quinolin-4-yl)thio)cyclobutanecarboxylate |
| 6b | 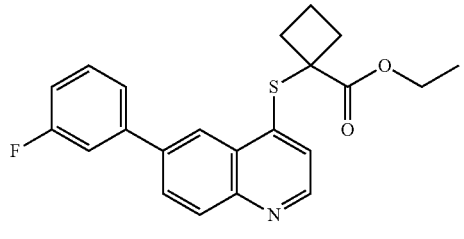
6b
ethyl 1-((6-(3-fluorophenyl)quinolin-4-yl)thio)cyclobutanecarboxylate |
| 7b | 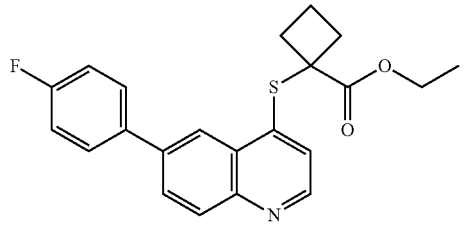
7b
ethyl 1-((6-(4-fluorophenyl)quinolin-4-yl)thio)cyclobutanecarboxylate |
| 8b | 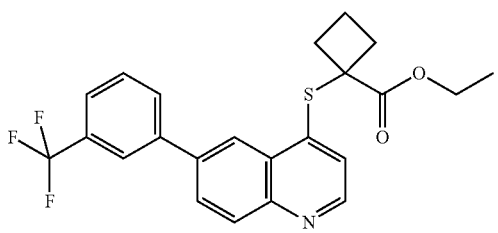
8b
ethyl 1-((6-(3-trifluoromethyl)phenyl)quinolin-4-yl)thio)cyclobutanecarboxylate |
| 9e | 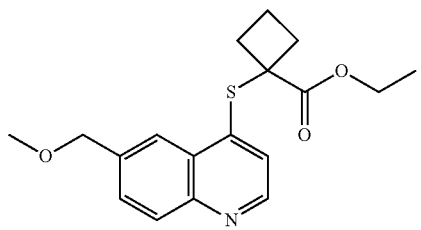
9e
ethyl 1-((6-(methoxymethyl)quinolin-4-yl)thio)cyclobutanecarboxylate |
| 10b | 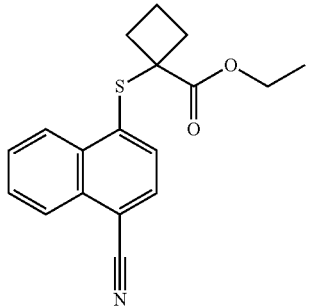
10b
ethyl 1-((4-cyanonaphthalen-1-yl)thio)cyclobutanecarboxylate |
| 11c | 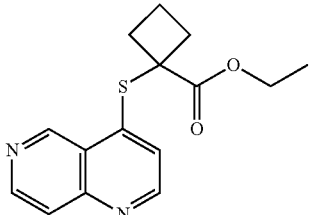
11c
ethyl 1-((1,6-naphthyridin-4-yl)thio)cyclobutanecarboxylate |

-continued

| Example No. | Structure and Name |
|---|---|
| 12c | 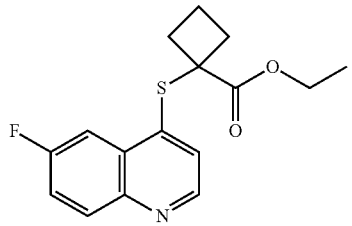
12c
ethyl 1-((6-fluoroquinolin-4-yl)thio)cyclobutanecarboxylate |
| 13a | 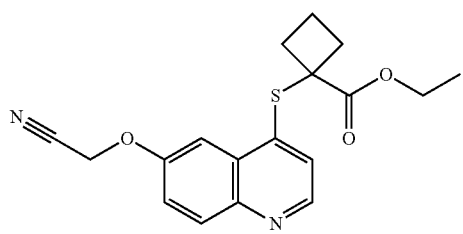
13a
ethyl 1-((6-(cyanomethoxy)quinolin-4-yl)thio)cyclobutanecarboxylate |
| 14a | 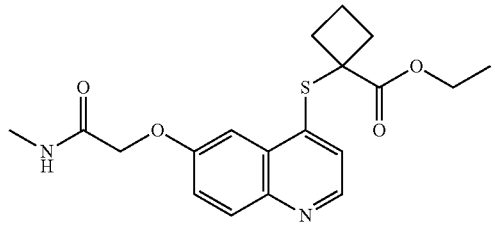
14a
ethyl 1-((6-(2-(methylamino)-2-oxoethoxy)quinolin-4-yl)thio)cyclobutanecarboxylate |
| 15a | 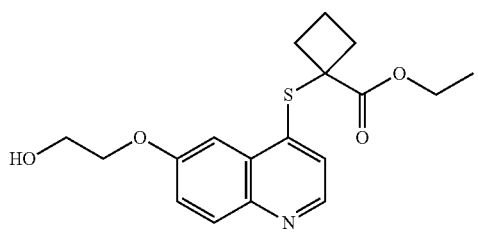
15a
ethyl 1-((6-(2-hydroxyethoxy)quinolin-4-yl)thio)cyclobutanecarboxylate |
| 16c | 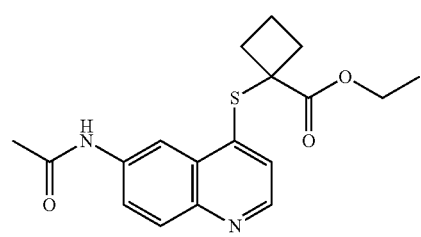
16c
ethyl 1-((6-acetamidoquinolin-4-yl)thio)cyclobutanecarboxylate |

-continued

| Example No. | Structure and Name |
|---|---|
| 17a | 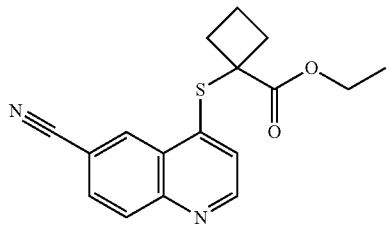
17a
ethyl 1-((6-cyanoquinolin-4-yl)thio)cyclobutanecarboxylate |
| 18b | 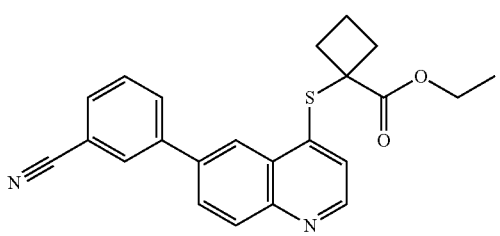
18b
ethyl 1-((6-(3-cyanophenyl)quinolin-4-yl)thio)cyclobutanecarboxylate |
| 19b | 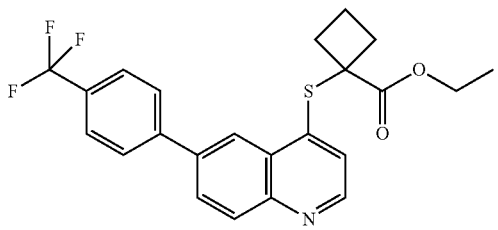
19b
ethyl 1-((6-(4-trifluoromethyl)phenyl)quinolin-4-yl)thio)cyclobutanecarboxylate |
| 20b | 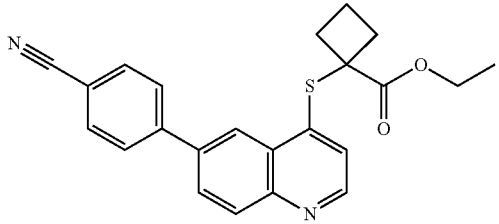
20b
ethyl 1-((6-(4-cyanophenyl)quinolin-4-yl)thio)cyclobutanecarboxylate |

| Example No. | Structure and Name |
|---|---|
| 21b | 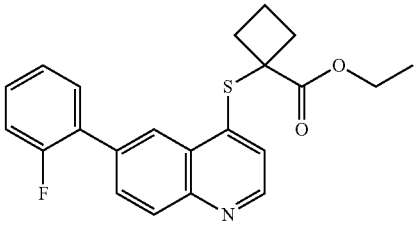<br>21b<br>ethyl 1-((6-(2-fluorophenyl)quinolin-4-yl)thio)cyclobutanecarboxylate |
| 22b | 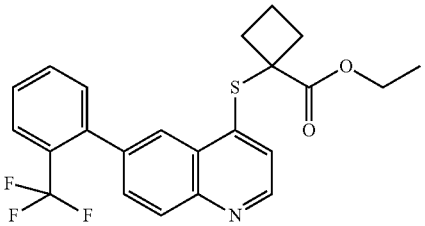<br>22b<br>ethyl 1-((6-(2-(trifluoromethyl)phenyl)quinolin-4-yl)thio)cyclobutanecarboxylate |
| 23b | 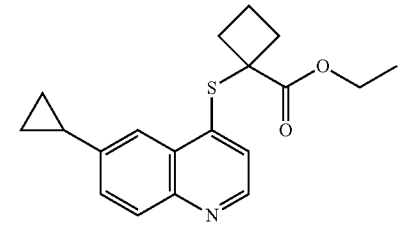<br>23b<br>ethyl 1-((6-cyclopropylquinolin-4-yl)thio)cyclobutanecarboxylate |
| 25b | 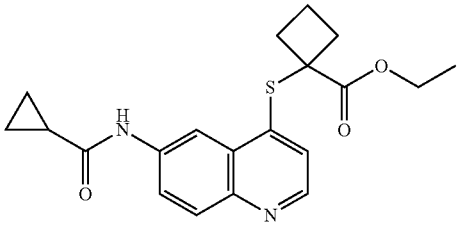<br>25b<br>ethyl 1-((6-(cyclopropanecarboxamido)quinolin-4-yl)thio)cyclobutanecarboxylate |
| 27b | 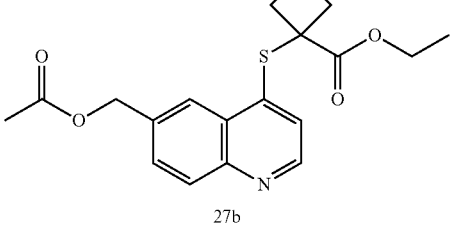<br>27b<br>ethyl 1-((6-(acetoxymethyl)quinolin-4-yl)thio)cyclobutanecarboxylate |
| 29f | 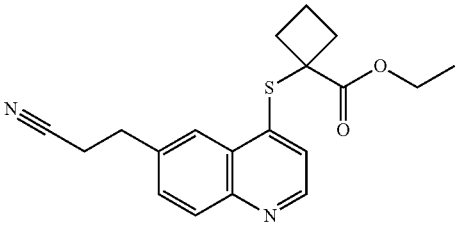<br>29f<br>ethyl 1-((6-(2-cyanoethyl)quinolin-4-yl)thio)cyclobutanecarboxylate |
| 30a | 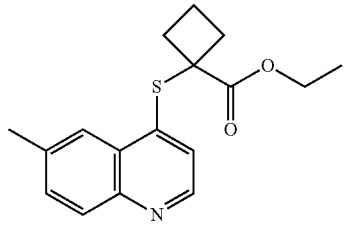<br>30a<br>ethyl 1-((6-methylquinolin-4-yl)thio)cyclobutanecarboxylate |
| 31c | 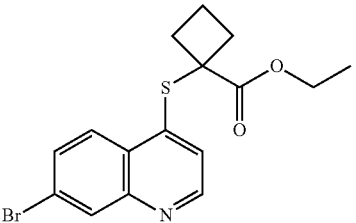<br>31c<br>ethyl 1-((7-bromoquinolin-4-yl)thio)cyclobutanecarboxylate |
| 32a | 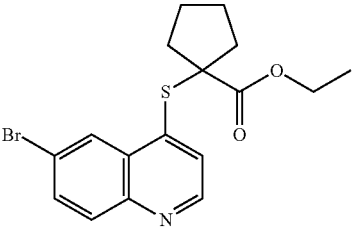<br>32a<br>ethyl 1-((6-bromoquinolin-4-yl)thio)cyclopentanecarboxylate |
| 33b | 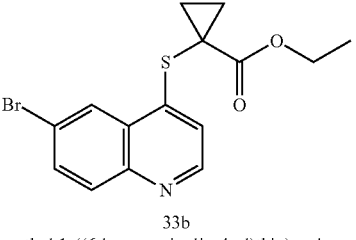<br>33b<br>ethyl 1-((6-bromoquinolin-4-yl)thio)cyclopropanecarboxylate | or a tautomer, mesomer, racemate, enantiomer, or diastereomer thereof, or mixture thereof, or a pharmaceutically acceptable salt thereof.

In another aspect, the invention provides a process of preparing a compound of general formula (I), or a tautomer, mesomer, racemate, enantiomer, or diastereomer thereof, or mixture thereof, or a pharmaceutically acceptable salt thereof, comprising a step of:

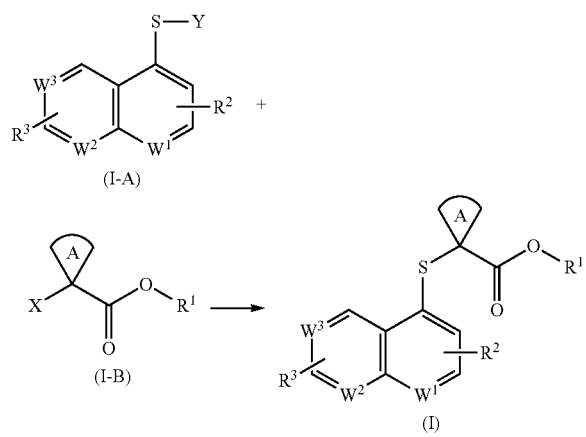

reacting a compound of formula (I-A) with a compound of formula (I-B) via a substitution reaction, and optionally hydrolyzing the resulting product under an alkaline condition to obtain a compound of formula (I);

wherein: X is a leaving group selected from the group consisting of halogen, OMs, OTs and OTf, preferably halogen; Y is a hydrogen or sodium atom; and ring A, $W^1$ to $W^3$, and $R^1$ to $R^3$ are as defined in formula (I).

In another aspect, the invention provides a compound of formula (I-A), or a tautomer, mesomer, racemate, enantiomer, or diastereomer thereof, or mixture thereof, or a pharmaceutically acceptable salt thereof:

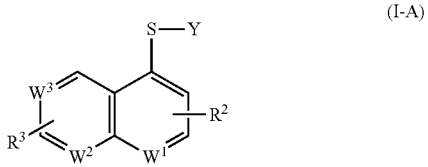

wherein:
Y is a hydrogen or sodium atom;
$W^1$ is N;
$W^2$ is $CR^b$;
$W^3$ is N or $CR^c$;
$R^b$ is hydrogen;
$R^c$ is selected from the group consisting of hydrogen, halogen, cyano, nitro, alkyl, alkoxy, alkenyl, alkynyl, cycloalkyl, heterocyclyl, aryl, heteroaryl, $-OR^4$, $-S(O)_mR^4$, $-C(O)R^4$, $-C(O)OR^4$, $-C(O)NR^5R^6$, $-NR^5R^6$ and $-NR^5C(O)R^6$, wherein the alkyl, alkoxy, alkenyl, alkynyl, cycloalkyl, heterocyclyl, aryl and heteroaryl are each independently optionally substituted with one or more groups selected from the group consisting of halogen, cyano, nitro, oxo, alkyl, haloalkyl, hydroxyalkyl, alkoxy, cycloalkyl, heterocyclyl, aryl, heteroaryl, $-OR^4$, $-S(O)_mR^4$, $-C(O)R^4$, $-C(O)OR^4$, $-C(O)NR^5R^6$, $-NR^5R^6$ and $-NR^5C(O)R^6$;

$R^2$ and $R^3$ are each independently hydrogen;

preferably, $R^c$ is alkyl or alkoxy, wherein the alkyl and alkoxy are each independently optionally substituted with one or more groups selected from the group consisting of cyano, nitro, oxo, alkyl, haloalkyl, hydroxyalkyl, alkenyl, alkynyl, cycloalkyl, heterocyclyl, aryl, heteroaryl, $-OR^4$, $-S(O)_mR^4$, $-C(O)R^4$, $-C(O)OR^4$, $-C(O)NR^5R^6$, $-NR^5R^6$ and $-NR^5C(O)R^6$;

$R^4$ is selected from the group consisting of hydrogen, alkyl, halogen, cycloalkyl, heterocyclyl, aryl and heteroaryl, wherein the alkyl, cycloalkyl, heterocyclyl, aryl and heteroaryl are each independently optionally substituted with one or more groups selected from the group consisting of halogen, cyano, nitro, hydroxy, oxo, alkyl, haloalkyl, hydroxyalkyl, alkoxy, cycloalkyl, heterocyclyl, aryl, heteroaryl, carboxyl, alkoxycarbonyl, $-C(O)NR^5R^6$, $-NR^5R^6$ and $-NR^5C(O)R^6$;

$R^5$ and $R^6$ are each independently selected from the group consisting of hydrogen, alkyl, cycloalkyl, heterocyclyl, aryl and heteroaryl, wherein the alkyl, cycloalkyl, heterocyclyl, aryl and heteroaryl are each independently optionally substituted with one or more groups selected from the group consisting of halogen, cyano, nitro, amino, hydroxy, oxo, alkyl, haloalkyl, hydroxyalkyl, alkoxy, cycloalkyl, heterocyclyl, aryl, heteroaryl, carboxyl and alkoxycarbonyl; and m is 0, 1, or 2.

Typical compounds of formula (I-A) include, but are not limited to the following:

| Example No. | Structure and Name |
|---|---|
| 9d | ![structure] <br> 9d <br> sodium 6-(methoxymethyl) quinoline-4-thiolate 9d |
| 11b | ![structure] <br> 11b <br> 1,6-naphthyridine-4-thiol 11b |
| 24c | ![structure] <br> 24c <br> 2-((4-mercaptoquinolin-6-yl)oxy) acetonitrile 24c |

| Example No. | Structure and Name |
|---|---|
| 29e | 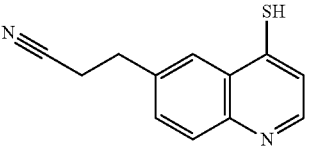<br>29e<br>3-(4-mercaptoquinolin-6-yl)propanenitrile 29e | or a tautomer, mesomer, racemate, enantiomer, or diastereomer thereof, or mixture thereof, or a pharmaceutically acceptable salt thereof.

The present invention also relates to a pharmaceutical composition comprising a therapeutically effective amount of a compound of formula (I), or a tautomer, mesomer, racemate, enantiomer, or diastereomer thereof, or mixture thereof, or a pharmaceutically acceptable salt thereof, and a pharmaceutically acceptable carrier, diluent or excipient. The pharmaceutical composition further comprises one or more additional uric-acid-lowering drugs selected from the group consisting of URAT1 inhibitors, xanthine oxidase inhibitors, xanthine dehydrogenase inhibitors and xanthine oxidoreductase inhibitors, preferably allopurinol, febuxostat or FYX-051.

The present invention also relates to use of a compound of formula (I), or a tautomer, mesomer, racemate, enantiomer, or diastereomer thereof, or mixture thereof, or a pharmaceutically acceptable salt thereof, or a pharmaceutical composition comprising the same, in the preparation of a medicament for inhibiting URAT1.

The present invention also relates to use of a compound of formula (I), or a tautomer, mesomer, racemate, enantiomer, or diastereomer thereof, or mixture thereof, or a pharmaceutically acceptable salt thereof, or the pharmaceutical composition comprising the same, in the preparation of a medicament for decreasing serum uric acid levels.

The present invention also relates to use of a compound of formula (I), or a tautomer, mesomer, racemate, enantiomer, or diastereomer thereof, or mixture thereof, or a pharmaceutically acceptable salt thereof, or a pharmaceutical composition comprising the same, in the preparation of a medicament for the treatment or prevention of diseases characterized by an abnormal uric acid level, wherein the diseases are selected from the group consisting of gout, recurrent gout attack, gouty arthritis, hyperuricemia, hypertension, cardiovascular disease, coronary heart disease, Lesch-Nyhan syndrome, Kelley-Seegmiller syndrome, kidney disease, kidney stone, kidney failure, joint inflammation, arthritis, urolithiasis, plumbism, hyperparathyroidism, psoriasis, sarcoidosis and hypoxanthine-guanine phosphoribosyltransferase deficiency, preferably gout and hyperuricemia.

The present invention also relates to use of a compound of formula (I), or a tautomer, mesomer, racemate, enantiomer, or diastereomer thereof, or mixture thereof, or a pharmaceutically acceptable salt thereof, or a pharmaceutical composition comprising the same, in the preparation of a medicament for decreasing serum uric acid levels, wherein the medicament is further combined with one or more additional uric-acid-lowering drugs selected from URAT1 inhibitors, xanthine oxidase inhibitors, xanthine dehydrogenase inhibitors and xanthine oxidoreductase inhibitors, preferably allopurinol, febuxostat and FYX-051, etc.

The present invention also relates to a method for inhibiting URAT1 comprising a step of administering to a subject in need thereof a therapeutically effective amount of a compound of formula (I), or a tautomer, mesomer, racemate, enantiomer, or diastereomer thereof, or mixture thereof, or a pharmaceutically acceptable salt thereof, or a pharmaceutical composition comprising the same.

The present invention also relates to a method for decreasing serum uric acid levels comprising a step of administering to a subject in need thereof a therapeutically effective amount of a compound of formula (I), or a tautomer, mesomer, racemate, enantiomer, or diastereomer thereof, or mixture thereof, or a pharmaceutically acceptable salt thereof, or a pharmaceutical composition comprising the same.

In other words, the present invention also relates to a method for the treatment or prevention of diseases characterized by an abnormal uric acid level, comprising a step of administering to a subject in need thereof a therapeutically effective amount of a compound of formula (I), or a tautomer, mesomer, racemate, enantiomer, or diastereomer thereof, or mixture thereof, or a pharmaceutically acceptable salt thereof, or a pharmaceutical composition comprising the same, wherein the diseases are selected from the group consisting of gout, recurrent gout attack, gouty arthritis, hyperuricemia, hypertension, cardiovascular disease, coronary heart disease, Lesch-Nyhan syndrome, Kelley-Seegmiller syndrome, kidney disease, kidney stones, kidney failure, joint inflammation, arthritis, urolithiasis, plumbism, hyperparathyroidism, psoriasis, sarcoidosis and hypoxanthine-guanine phosphoribosyltransferase deficiency, preferably gout or hyperuricemia.

The present invention also relates to a method for decreasing serum uric acid levels comprising a step of administering to a subject in need thereof a therapeutically effective amount of a compound of formula (I), or a tautomer, mesomer, racemate, enantiomer, or diastereomer thereof, or mixture thereof, or a pharmaceutically acceptable salt thereof, or a pharmaceutical composition comprising the same, and one or more additional uric-acid-lowering drugs selected from the group consisting of URAT1 inhibitors, xanthine oxidase inhibitors, xanthine dehydrogenase inhibitors and xanthine oxidoreductase inhibitors, preferably allopurinol, febuxostat or FYX-051, etc.

The present invention also relates to a compound of formula (I), or a tautomer, mesomer, racemate, enantiomer, or diastereomer thereof, or mixture thereof, or a pharmaceutically acceptable salt thereof, or the pharmaceutical composition comprising the same, for use as a medicament for inhibiting the activity of URAT1.

The present invention also relates to a compound of formula (I), or a tautomer, mesomer, racemate, enantiomer, or diastereomer thereof, or mixture thereof, or a pharmaceutically acceptable salt thereof, or a pharmaceutical composition comprising the same, for use as a medicament for decreasing serum uric acid levels.

The present invention also relates to a compound of formula (I), or a tautomer, mesomer, racemate, enantiomer, or diastereomer thereof, or mixture thereof, or a pharmaceutically acceptable salt thereof, or a pharmaceutical composition comprising the same, for use as a medicament for the treatment or prevention of diseases characterized by an abnormal uric acid level, wherein the diseases are selected from the group consisting of gout, recurrent gout attack, gouty arthritis, hyperuricemia, hypertension, cardiovascular disease, coronary heart disease, Lesch-Nyhan syndrome, Kelley-Seegmiller syndrome, kidney disease, kidney stone, kidney failure, joint inflammation, arthritis, urolithiasis, plumbism, hyperparathyroidism, psoriasis, sarcoidosis and hypoxanthine-guanine phosphoribosyltransferase deficiency, preferably gout or hyperuricemia.

The present invention also relates to a compound of formula (I), or a tautomer, mesomer, racemate, enantiomer, or diastereomer thereof, or mixture thereof, or a pharmaceutically acceptable salt thereof, or a pharmaceutical composition comprising the same, for use as a medicament for decreasing serum uric acid levels, wherein the medicament further comprises one or more additional uric-acid-lowering drugs selected from the group consisting of URAT1 inhibitors, xanthine oxidase inhibitors, xanthine dehydrogenase inhibitors and xanthine oxidoreductase inhibitors, preferably allopurinol, febuxostat or FYX-051, etc.

The pharmaceutical composition comprising the active ingredient can be in a form suitable for oral administration, for example, tablets, troches, lozenges, aqueous or oily suspensions, dispersible powders or granules, emulsions, hard or soft capsules, or syrups or elixirs. Compositions intended for oral use are optionally prepared according to known methods, and such compositions may contain one or more agents selected from the group consisting of sweetening agents, flavoring agents, coloring agents and preserving agents in order to provide pharmaceutically acceptable and palatable preparations. Tablets contain the active ingredient in admixture with non-toxic pharmaceutically acceptable excipients which are suitable for the manufacture of tablets. These excipients may be inert excipients, such as calcium carbonate, sodium carbonate, lactose, calcium phosphate or sodium phosphate; granulating and disintegrating agents, such as microcrystalline cellulose, sodium crosscarmellose, corn starch or alginic acid; binding agents, such as starch, gelatin, polyvinylpyrrolidone or acacia; and lubricating agents, such as magnesium stearate, stearic acid or talc. The tablets may be uncoated or coated by known techniques to mask the taste of the drug or delay disintegration and absorption in the gastrointestinal tract, thereby providing sustained release over a long period. For example, a water soluble taste masking material such as hydroxypropyl methylcellulose or hydroxypropylcellulose, or a material for extending time such as ethyl cellulose or cellulose acetate butyrate can be used.

Oral formulations can also be presented as hard gelatin capsules in which the active ingredient is mixed with an inert solid diluent, such as calcium carbonate, calcium phosphate or kaolin, or as soft gelatin capsules in which the active ingredient is mixed with a water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, such as sodium carboxymethylcellulose, methylcellulose, hydroxypropylmethylcellulose, sodium alginate, polyvinylpyrrolidone and gum acacia; dispersing or wetting agents which may be a naturally occurring phosphatide, such as lecithin, or condensation products of an alkylene oxide with fatty acids, such as polyoxyethylene stearate, or condensation products of ethylene oxide with long chain aliphatic alcohols, such as heptadecaethyleneoxy cetanol, or condensation products of ethylene oxide with partial esters derived from fatty acids and hexitols, such as polyoxyethylene sorbitan monooleate, or condensation products of ethylene oxide with partial esters derived from fatty acids and hexitol anhydrides, such as polyethylene sorbitan monooleate. The aqueous suspensions can also contain one or more preservatives, such as ethylparaben or n-propylparaben, one or more coloring agents, one or more flavoring agents, and one or more sweeting agents, such as sucrose, saccharin or aspartame.

Oil suspensions can be formulated by suspending the active ingredient in a vegetable oil, such as arachis oil, olive oil, sesame oil or coconut oil, or in a mineral oil such as liquid paraffin. The oil suspensions can contain a thickening agent, such as beeswax, hard paraffin or cetyl alcohol. The aforesaid sweetening agents and flavoring agents can be added to provide a palatable preparation. These compositions can be preserved by the addition of an antioxidant such as butylated hydroxyanisole or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, such as sweetening, flavoring and coloring agents, may also be presented. These compositions may be preserved by the addition of an antioxidant such as ascorbic acid.

The pharmaceutical compositions can also be in the form of oil-in-water emulsions. The oil phase may be a vegetable oil, such as olive oil or arachis oil, or a mineral oil, such as liquid paraffin or mixtures thereof. Suitable emulsifying agents can be naturally occurring phosphatides, such as soy bean lecithin, and esters or partial esters derived from fatty acids and hexitol anhydrides, such as sorbitan monooleate, and condensation products of the partial esters with ethylene oxide, such as polyoxyethylene sorbitan monooleate. The emulsions can also contain sweetening agents, flavoring agents, preservatives and antioxidants. Syrups and elixirs can be formulated with sweetening agents, such as glycerol, propylene glycol, sorbitol or sucrose. Such formulations can also contain a demulcent, a preservative, a coloring agent and an antioxidant.

The pharmaceutical compositions can be in the form of sterile injectable aqueous solutions. Among the acceptable vehicles and solvents that can be employed are water, Ringer's solution and isotonic sodium chloride solution. The sterile injectable preparation can also be a sterile injectable oil-in-water microemulsion in which the active ingredient is dissolved in the oil phase. For example, the active ingredient can be first dissolved in a mixture of soybean oil and lecithin, then the oil solution is introduced into a mixture of water and glycerol and processed to form a microemulsion. The injectable solutions or microemulsions can be introduced into an individual's bloodstream by local bolus injection. Alternatively, it may be advantageous to administer the solution or microemulsion in such a way as to maintain a constant circulating concentration of the compound of the invention. In order to maintain such a constant concentration, a continuous intravenous delivery device can be utilized. An example of such a device is the Deltec CADD-PLUS™ model 5400 intravenous pump.

The pharmaceutical compositions can be in the form of sterile injectable aqueous or oily suspensions for intramuscular and subcutaneous administration. The suspensions can be formulated according to the known art by using the aforesaid suitable dispersing or wetting agents and suspending agents. The sterile injectable preparation can also be a sterile injectable solution or suspension in a nontoxic parenterally acceptable diluent or solvent, for example, a solution in 1,3-butanediol. In addition, a sterile, fixed oil can be conventionally employed as a solvent or a suspending medium. For this purpose, any blend fixed oil for synthesizing mono- or diglycerides can be employed. In addition, fatty acids such as oleic acid can be used in the preparation of injections.

The compounds of the invention can also be administered in the form of suppositories for rectal administration. The compositions can be prepared by mixing the active ingredient with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

It is known to those skilled in the art that the dosage of a drug depends on a variety of factors including, but not limited to the following factors: activity of particular compound, age of patient, weight of patient, general health of patient, behavior of patient, diet of patient, time of administration, route of administration, rate of excretion, drug combination etc. In addition, the best treatment, such as treatment model, daily dose of a compound of formula (I) or the type of pharmaceutically acceptable salt thereof can be verified by traditional treatment programs.

DETAILED DESCRIPTION OF THE INVENTION

Unless otherwise stated, the terms used in the specification and claims have the meanings described below.

"Alkyl" refers to a saturated aliphatic hydrocarbon group including $C_1$-$C_{20}$ straight chain and branched chain groups. Preferably, an alkyl group is an alkyl having 1 to 10 carbon atoms, and more preferably, an alkyl having 1 to 6 carbon atoms, and most preferably, an alkyl having 1 to 4 carbon atoms. Representative examples include, but are not limited to, methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-nonyl, 2-methyl-2-ethylhexyl, 2-methyl-3-ethylhexyl, 2,2-diethylpentyl, n-decyl, 3,3-diethylhexyl, 2,2-diethylhexyl, and isomers or branched chains thereof. More preferably, an alkyl group is a lower alkyl having 1 to 6 carbon atoms. Representative examples include, but are not limited to, methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, etc. The alkyl group can be substituted or unsubstituted. When substituted, the substituent group(s) can be substituted at any available connection point, and preferably the substituent group(s) is one or more groups independently selected from the group consisting of alkyl, alkenyl, alkynyl, alkyloxyl, alkylsulfo, alkylamino, halogen, thiol, hydroxy, nitro, cyano, cycloalkyl, heterocyclyl, aryl, heteroaryl, cycloalkoxy, heterocyclic alkoxy, cycloalkylthio, heterocyclic alkylthio, oxo group, amino, haloalkyl, hydroxyalkyl, carboxyl and alkoxycarbonyl.

"Alkenyl" refers to an alkyl defined as above that has at least two carbon atoms and at least one carbon-carbon double bond, for example, vinyl, 1-propenyl, 2-propenyl, 1-, 2-, or 3-butenyl, etc., preferably $C_{2-10}$ alkenyl, more preferably $C_{2-6}$ alkenyl, and most preferably $C_{2-4}$ alkenyl. The alkenyl group can be substituted or unsubstituted. When substituted, the substituent group(s) is preferably one or more groups independently selected from the group consisting of alkyl, alkenyl, alkynyl, alkoxy, alkylsulfo, alkylamino, halogen, thiol, hydroxy, nitro, cyano, cycloalkyl, heterocyclyl alkyl, aryl, heteroaryl, cycloalkoxy, heterocyclic alkoxy, cycloalkylthio, heterocyclic alkylthio, oxo group, amino, haloalkyl, hydroxyalkyl, carboxyl and alkoxycarbonyl.

"Alkynyl" refers to an alkyl defined as above that has at least two carbon atoms and at least one carbon-carbon triple bond, for example, ethynyl, 1-propynyl, 2-propynyl, 1-, 2-, or 3-butynyl, etc., preferably $C_{2-10}$ alkynyl, more preferably $C_{2-6}$ alkynyl, and most preferably $C_{2-4}$ alkynyl. The alkynyl group can be substituted or unsubstituted. When substituted, the substituent group(s) is preferably one or more groups independently selected from the group consisting of alkyl, alkenyl, alkynyl, alkoxy, alkylsulfo, alkylamino, halogen, thiol, hydroxy, nitro, cyano, cycloalkyl, heterocyclic alkyl, aryl, heteroaryl, cycloalkoxy, heterocyclic alkoxy, cycloalkylthio, heterocyclic alkylthio, oxo group, amino, haloalkyl, hydroxyalkyl, carboxyl and alkoxycarbonyl.

"Cycloalkyl" refers to a saturated or partially unsaturated monocyclic or polycyclic hydrocarbon group having 3 to 20 carbon atoms, preferably 3 to 12 carbon atoms, more preferably 3 to 10 carbon atoms, even more preferably 3 to 6 carbon atoms, and most preferably cyclopropyl or cyclobutyl. Representative examples of monocyclic cycloalkyls include, but are not limited to, cyclopropyl, cyclobutyl, cyclopentyl, cyclopentenyl, cyclohexyl, cyclohexenyl, cyclohexadienyl, cycloheptyl, cycloheptatrienyl, cyclooctyl, etc, preferably cyclopropyl or cyclohexenyl. Polycyclic cycloalkyl includes a cycloalkyl having a spiro ring, fused ring or bridged ring. The cycloalkyl group can be substituted or unsubstituted. When substituted, preferably the substituent group(s) is one or more groups independently selected from the group consisting of alkyl, alkenyl, alkynyl, alkyloxyl, alkylsulfo, alkylamino, halogen, thiol, hydroxy, nitro, cyano, cycloalkyl, heterocyclyl, aryl, heteroaryl, cycloalkoxy, heterocyclic alkoxy, cycloalkylthio, heterocyclic alkylthio, oxo group, amino, haloalkyl, hydroxyalkyl, carboxyl and alkoxycarbonyl.

"Heterocyclyl" refers to a 3 to 20 membered saturated or partially unsaturated monocyclic or polycyclic hydrocarbon group having one or more heteroatoms selected from the group consisting of N, O, and $S(O)_m$ (wherein m is an integer selected from 0, 1 and 2) as ring atoms, but excluding —O—O—, —O—S— or —S—S— in the ring, with the remaining ring atoms being C. Preferably, a heterocyclyl is 3 to 12 atoms, wherein 1 to 4 atoms are heteroatoms; more preferably 3 to 10 atoms; and most preferably 5 to 6 atoms. Representative examples of monocyclic heterocyclyls include, but are not limited to, pyrrolidyl, piperidyl, piperazinyl, morpholinyl, sulfo-morpholinyl, homopiperazinyl, pyranyl, tetrahydrofuranyl, etc. Polycyclic heterocyclyl includes the heterocyclyl having a spiro ring, fused ring or bridged ring. The heterocyclyl group can be substituted or unsubstituted. When substituted, preferably the substituent group(s) is one or more groups independently selected from the group consisting of alkyl, alkenyl, alkynyl, alkyloxyl, alkylsulfo, alkylamino, halogen, thiol, hydroxy, nitro, cyano, cycloalkyl, heterocyclyl, aryl, heteroaryl, cycloalkoxy, heterocyclic alkoxy, cycloalkylthio, heterocyclic alkylthio, oxo group, amino, haloalkyl, hydroxyalkyl, carboxyl and alkoxycarbonyl.

"Aryl" refers to a 6 to 14 membered all-carbon monocyclic ring or polycyclic fused ring (a "fused" ring system means that each ring in the system shares an adjacent pair of carbon atoms with another ring in the system), which has a completely conjugated pi-electron system. Preferably, an aryl is 6 to 10 membered, more preferably phenyl and naphthyl, and most preferably phenyl. The aryl can be fused to the ring of a heteroaryl, heterocyclyl or cycloalkyl, wherein the ring bound to the parent structure is aryl. Representative examples include, but are not limited to, the following groups:

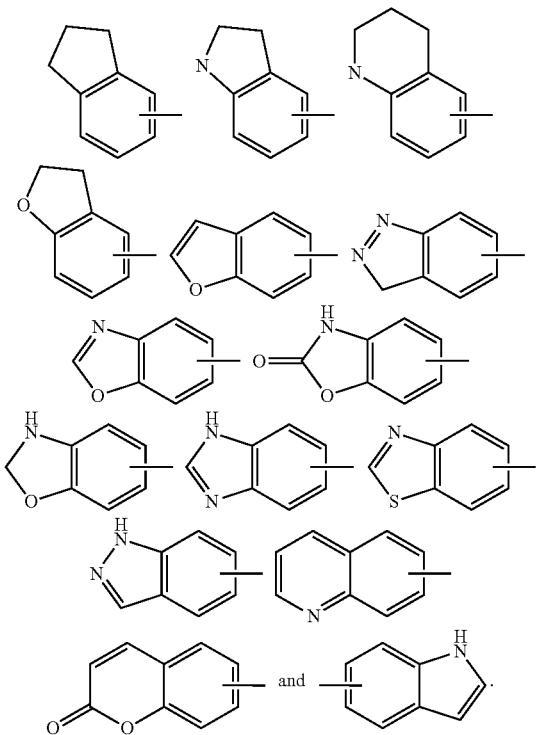

The aryl group can be substituted or unsubstituted. When substituted, the substituent group(s) is preferably one or more groups independently selected from the group consisting of alkyl, alkenyl, alkynyl, alkoxy, alkylsulfo, alkylamino, halogen, thiol, hydroxy, nitro, cyano, cycloalkyl, heterocyclyl, aryl, heteroaryl, cycloalkoxy, heterocyclic alkoxy, cycloalkylthio, heterocyclic alkylthio, amino, haloalkyl, hydroxyalkyl, carboxyl and alkoxycarbonyl, —OR$^4$, —S(O)$_m$R$^4$, —C(O)R$^4$, —C(O)NR$^5$R$^6$, —NR$^5$R$^6$ and —NR$^5$C(O)R$^6$, wherein R$^4$, R$^5$, R$^6$, and m are as defined in formula (I).

"Heteroaryl" refers to an aryl system having 1 to 4 heteroatoms selected from the group consisting of O, S and N, and having 5 to 14 ring atoms. Preferably, a heteroaryl is 5- to 10-membered, more preferably 5- or 6-membered, for example, thiadiazolyl, pyrazolyl, oxazolyl, oxadiazolyl, imidazolyl, triazolyl, thiazolyl, furyl, thienyl, pyridyl, pyrrolyl, N-alkyl pyrrolyl, pyrimidinyl, pyrazinyl, imidazolyl, tetrazolyl, etc. The heteroaryl can be fused with the ring of an aryl, heterocyclyl or cycloalkyl, wherein the ring bound to the parent structure is heteroaryl. Representative examples include, but are not limited to, the following groups:

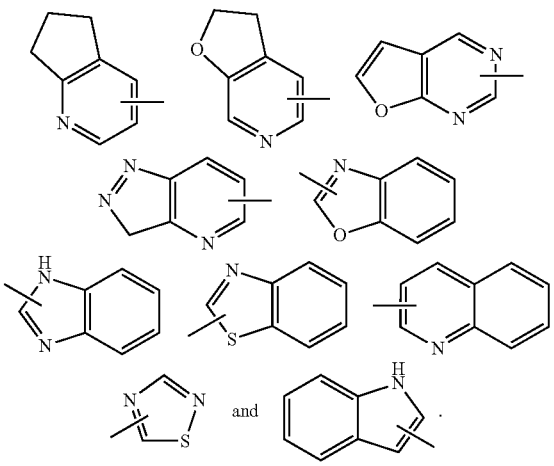

The heteroaryl group can be substituted or unsubstituted. When substituted, the substituent group(s) is preferably one or more groups independently selected from the group consisting of alkyl, alkenyl, alkynyl, alkoxy, alkylsulfo, alkylamino, halogen, thiol, hydroxy, nitro, cyano, cycloalkyl, heterocyclyl, aryl, heteroaryl, cycloalkoxy, heterocyclic alkoxy, cycloalkylthio, heterocyclic alkylthio, amino, haloalkyl, hydroxyalkyl, carboxyl and alkoxycarbonyl.

"Alkoxy" refers to both an —O-(alkyl) and an —O-(unsubstituted cycloalkyl) group, wherein the alkyl and cycloalkyl are defined as above. Representative examples include, but are not limited to, methoxy, ethoxy, propoxy, butoxy, cyclopropyloxy, cyclobutyloxy, cyclopentyloxy, cyclohexyloxy, and the like. The alkoxy can be substituted or unsubstituted. When substituted, the substituent is preferably one or more groups independently selected from the group consisting of alkyl, alkenyl, alkynyl, alkoxy, alkylsulfo, alkylamino, halogen, thiol, hydroxy, nitro, cyano, cycloalkyl, heterocyclyl, aryl, heteroaryl, cycloalkoxy, heterocyclic alkoxy, cycloalkylthio, heterocyclic alkylthio, amino, haloalkyl, hydroxyalkyl, carboxyl and alkoxycarbonyl.

"Haloalkyl" refers to an alkyl group substituted by one or more halogens, wherein the alkyl is as defined above.

"Hydroxy" refers to an —OH group.

"Hydroxy alkyl" refers to an alkyl group substituted by a hydroxy group, wherein the alkyl is as defined above.

"Halogen" refers to fluoro, chloro, bromo or iodo atoms.

"Amino" refers to an —NH$_2$ group.

"Cyano" refers to a —CN group.

"Nitro" refers to a —NO$_2$ group.

"Oxo group" refers to a ═O group.

"Carboxyl" refers to a —C(O)OH group.

"Alkoxycarbonyl" refers to a —C(O)O(alkyl) or (cycloalkyl) group, wherein the alkyl and cycloalkyl are defined as above.

"Optional" or "optionally" means that the event or circumstance described subsequently can, but need not occur, and the description includes the instances in which the event or circumstance does or does not occur. For example, "the heterocyclic group optionally substituted by an alkyl" means that an alkyl group can be, but need not be, present, and the description includes the case of the heterocyclic group being substituted with an alkyl and the heterocyclic group being not substituted with an alkyl.

"Substituted" refers to one or more hydrogen atoms in the group, preferably up to 5, more preferably 1 to 3 hydrogen atoms, each independently substituted with a corresponding number of substituents. It goes without saying that the substituents exist in their only possible chemical position. The person skilled in the art is able to determine if the substitution is possible or impossible without paying excessive efforts by experiment or theory. For example, the combination of amino or hydroxy group having free hydrogen and carbon atoms having unsaturated bonds (such as olefinic) may be unstable.

A "pharmaceutical composition" refers to a mixture of one or more of the compounds described in the present invention or physiologically/pharmaceutically acceptable salts or prodrugs thereof and other chemical components such as physiologically/pharmaceutically acceptable carriers and excipients. The purpose of a pharmaceutical composition is to facilitate administration of a compound to an organism, which is conducive to the absorption of the active ingredient, thus displaying biological activity.

Synthesis Method of the Compound of the Present Invention

In order to complete the purpose of the invention, the present invention applies the following technical solution:

A process of preparing a compound of formula (I) of the invention, a tautomer, racemate, enantiomer, or diastereomer thereof, or a mixture thereof, or a pharmaceutically acceptable salt thereof, comprises the steps of:

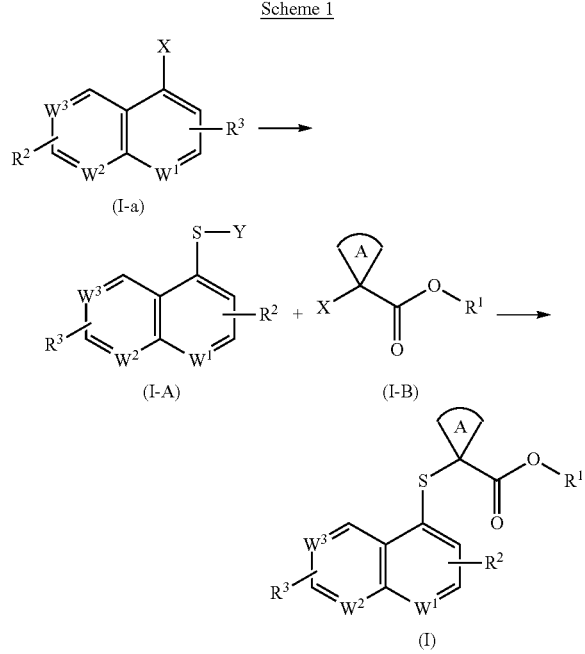

reacting a compound of formula (I-a) with sodium sulfide in a solvent to obtain a fused ring compound (I-A); reacting the compound of fused ring compound (I-A) with a compound of formula (I-B) via a substitution reaction, and optionally hydrolyzing the resulting product under an alkaline condition to obtain a compound of formula (I);

wherein: X is a leaving group selected from the group consisting of halogen, OMs (methanesulfonyloxy), OTs (p-tosyloxy) and OTf (trifluoromethanesulfonyloxy), preferably halogen; Y is a hydrogen or sodium atom; ring A, $W^1$ to $W^3$, $R^1$ to $R^3$ are as defined in formula (I).

A process of preparing a compound of formula (II), or a tautomer, mesomer, racemate, enantiomer, or diastereomer thereof, or mixture thereof, or a pharmaceutically acceptable salt thereof, comprises the steps of:

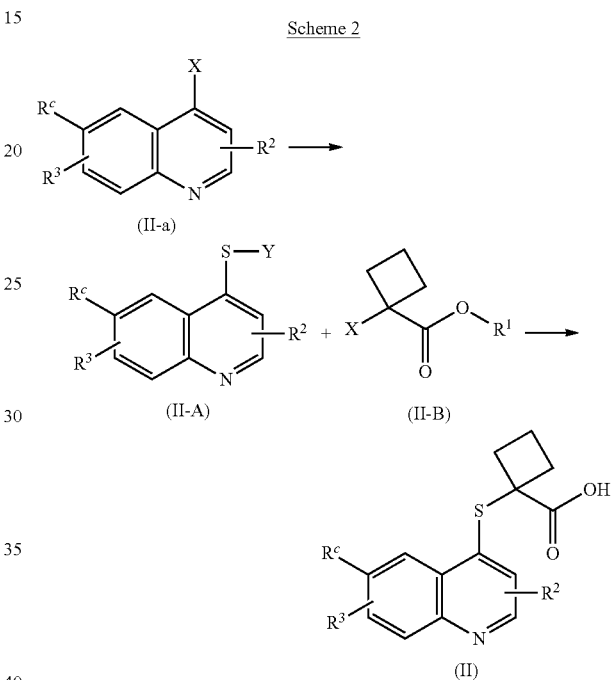

reacting a compound of formula (II-a) with sodium sulfide in a solvent to obtain a quinoline compound (II-A); reacting the quinoline compound (II-A) with a compound of formula (II-B) via a substitution reaction, and optionally hydrolyzing the resulting product under an alkaline condition to obtain a compound of formula (II);

wherein: X is a leaving group selected from the group consisting of halogen, OMs, OTs and OTf, preferably halogen; Y is a hydrogen or sodium atom; $R^1$ is selected from the group consisting of hydrogen and alkyl, $R^c$, $R^2$, and $R^3$ are as defined in formula (II).

A process of preparing a compound of formula (III), or a tautomer, mesomer, racemate, enantiomer, or diastereomer thereof, or mixture thereof, or a pharmaceutically acceptable salt thereof, comprises the steps of:

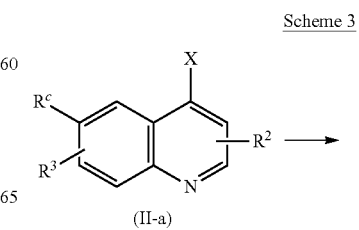

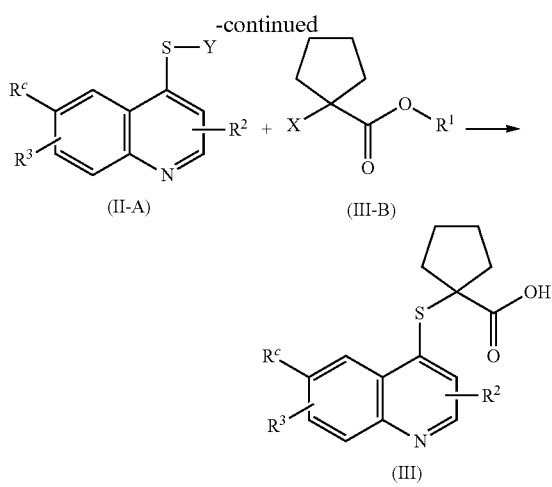

reacting a compound of formula (II-a) with sodium sulfide in a solvent to obtain a quinoline compound (II-A); reacting the quinoline compound (II-A) with a compound of formula (III-B) via a substitution reaction, and optionally hydrolyzing the resulting product under an alkaline condition to obtain a compound of formula (III);

wherein: X is a leaving group selected from the group consisting of halogen, OMs, OTs and OTf, preferably halogen; Y is a hydrogen or sodium atom; $R^1$ is selected from the group consisting of hydrogen and alkyl, $R^c$, $R^2$, and $R^3$ are as defined in formula (III).

A process of preparing a compound of formula (IV), or a tautomer, mesomer, racemate, enantiomer, or diastereomer thereof, or mixture thereof, or a pharmaceutically acceptable salt thereof, comprises the steps of:

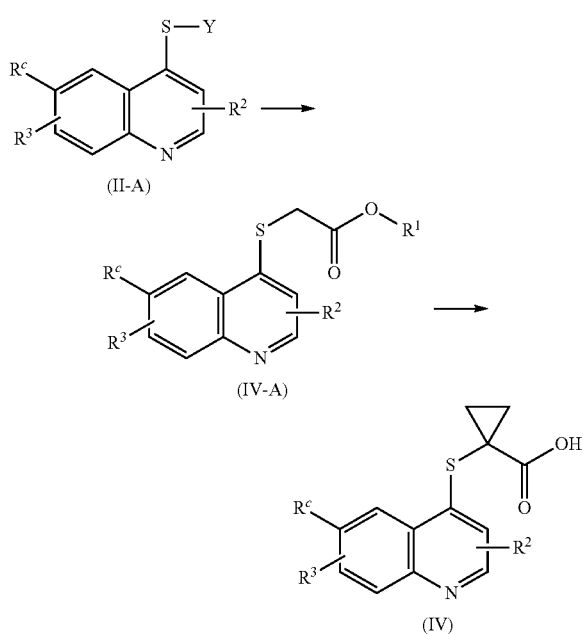

reacting a quinoline compound (II-A) with haloacetate via a substitution reaction to obtain a compound of formula (IV-A); reacting the compound of formula (IV-A) with dihalo-ethane, and optionally hydrolyzing the resulting product under an alkaline condition to obtain a compound of formula (IV);

wherein: Y is a hydrogen or sodium atom; $R^1$ is selected from the group consisting of hydrogen and alkyl, $R^c$, $R^2$, and $R^3$ are as defined in formula (IV).

In the aforesaid schemes, the alkaline condition is provided by a reagent including an organic alkali and an inorganic alkali, wherein the organic alkali includes, but is not limited to, triethylamine, pyridine, 2,6-lutidine, n-butyllithium, potassium tert-butoxide and tetrabutyl ammonium bromide; and the inorganic alkali includes, but is not limited to, cesium carbonate, sodium carbonate, sodium bicarbonate, potassium carbonate, potassium bicarbonate, lithium hydroxide, sodium hydroxide, potassium hydroxide and sodium hydride.

In the aforesaid schemes, the solvent includes, but is not limited to, N,N-dimethylformamide, methanol, ethanol, water, tetrahydrofuran, dichloromethane, 1,4-dioxane, acetonitrile, 1,2-dichloroethane, dimethylsulfoxide and diphenyl ether.

Preferred Embodiments

The invention will be further illustrated with reference to the following specific examples. It is to be understood that these examples are merely intended to demonstrate the invention without limiting the scope of the invention.

The experimental methods in the following examples for which no specific conditions are indicated will be carried out according to conventional conditions or recommended conditions of the raw materials and the product manufacturer. The experimental reagents for which no specific sources are indicated will be conventional reagents generally purchased from market.

EXAMPLES

Compound structures were identified by nuclear magnetic resonance (NMR) and/or mass spectrometry (MS). NMR was determined by a Bruker AVANCE-400 machine. The solvents were deuterated-dimethyl sulfoxide (DMSO-$d_6$), deuterated-chloroform (CDCl$_3$) and deuterated-methanol (CD$_3$OD), with tetramethylsilane (TMS) as an internal standard. NMR chemical shifts (δ) were given in $10^{-6}$ (ppm).

MS was determined by a FINNIGAN LCQAd (ESI) mass spectrometer (manufacturer: Thermo, type: Finnigan LCQ advantage MAX).

High performance liquid chromatography (HPLC) was determined on an Agilent 1200DAD high pressure liquid chromatography spectrometer (Sunfire C18 150×4.6 mm chromatographic column) and a Waters 2695-2996 high pressure liquid chromatography spectrometer (Gimini C18 150×4.6 mm chromatographic column).

The average inhibition rate of kinase and IC$_{50}$ were determined by a NovoStar ELISA (BMG Co., Germany).

For thin-layer silica gel chromatography (TLC) Yantai Huanghai HSGF254 or Qingdao GF254 silica gel plate was used. The dimension of the plates used in TLC were 0.15 mm to 0.2 mm, and the dimension of the plates used in product purification were 0.4 mm to 0.5 mm.

Column chromatography generally used Yantai Huanghai 200 to 300 mesh silica gel as carrier.

The known starting materials of the invention can be prepared by conventional synthesis methods in the prior art, or can be purchased from ABCR GmbH & Co. KG, Acros Organics, Aldrich Chemical Company, Accela ChemBio Inc., or Dari Chemical Company, etc.

Unless otherwise stated, the following reactions were placed under nitrogen atmosphere or argon atmosphere.

The term "argon atmosphere" or "nitrogen atmosphere" means that a reaction flask is equipped with a 1 L argon or nitrogen balloon.

The term "hydrogen atmosphere" means that a reaction flask is equipped with a 1 L hydrogen balloon.

Pressured hydrogenation reactions were performed with a Parr 3916EKX hydrogenation spectrometer and a QL-500 hydrogen generator or a HC2-SS hydrogenation spectrometer.

In hydrogenation reactions, the reaction system was generally vacuumed and filled with hydrogen, with the above operation repeated three times.

Unless otherwise stated, the solution used in the examples refers to an aqueous solution.

Unless otherwise stated, the reaction temperature in the examples was room temperature.

Room temperature was the most appropriate reaction temperature, and the range of the room temperature was 20° C. to 30° C.

The reaction process was monitored by thin layer chromatography (TLC), and the system of developing solvent included: A: dichloromethane and methanol system, B: n-hexane and ethyl acetate system, C: petroleum ether and ethyl acetate system, D: acetone. The ratio of the volume of the solvent was adjusted according to the polarity of the compounds.

The elution system for purification of the compounds by column chromatography and thin layer chromatography included: A: dichloromethane and methanol system, B: n-hexane and ethyl acetate system, C: n-hexane and acetone system, D: n-hexane, E: ethyl acetate. The volume of the solvent was adjusted according to the polarity of the compounds, and sometimes a little alkaline reagent, such as triethylamine or acidic reagent, was also added.

Example 1

1-(quinolin-4-ylthio)cyclobutanecarboxylic acid

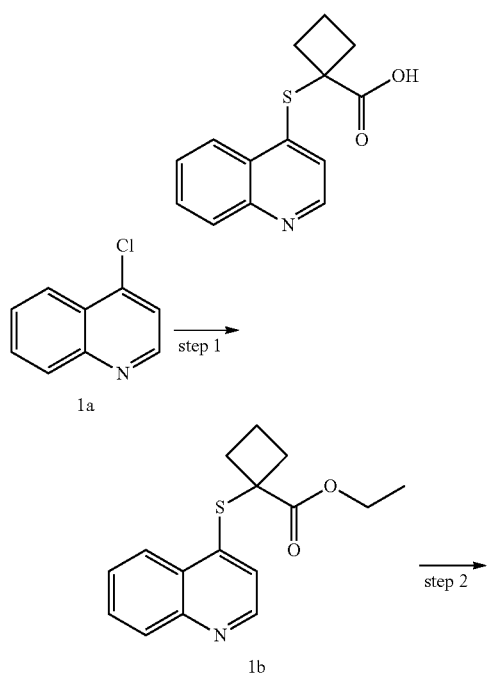

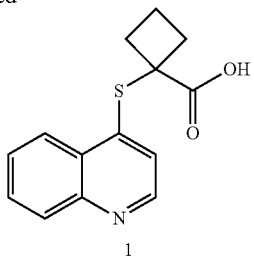

Step 1

Ethyl 1-(quinolin-4-ylthio)cyclobutanecarboxylate 4-chloroquinoline 1a (300 mg, 1.83 mmol) and sodium sulphide (143 mg, 1.83 mmol) were added to 4 mL of N,N-dimethylformamide. Upon completion of the addition, the reaction solution was heated to 70° C. and stirred for 4 hours. The reaction process was monitored by TLC until completion of the reaction, and a DMF solution of sodium 4-quinolyl thiol was obtained, and used directly in the next step. Ethyl 1-bromocyclobutanecarboxylate (154 mg, 0.72 mmol) was directly added to the pre-prepared DMF solution of sodium 4-quinolyl thiol. The reaction solution was heated to 70° C. and stirred for 16 hours until TLC showed completion of the reaction. 100 mL of saturated brine was added, and the reaction solution was extracted with ethyl acetate (100 mL×3). The organic phases were combined, dried over anhydrous sodium sulfate and filtered. The filtrate was concentrated under reduced pressure to obtain the title compound ethyl 1-(quinolin-4-ylthio)cyclobutanecarboxylate 1b, which was used directly in the next step.

MS m/z (ESI): 288.1 [M+1]

Step 2

1-(quinolin-4-ylthio)cyclobutanecarboxylic acid

Ethyl 1-(quinolin-4-ylthio)cyclobutanecarboxylate 1b (172 mg, 0.6 mmol) was dissolved in 8 mL of a mixture of methanol and water (V:V=1:1), followed by addition of sodium hydroxide (96 mg, 2.4 mmol). Upon completion of the addition, the reaction solution was heated to 50° C. and stirred for 4 hours. The reaction solution was evaporated under reduced pressure to remove methanol. The aqueous phase was washed with diethyl ether (4 mL×1), added dropwise with 1 M hydrochloric acid to adjust the pH to 1, and washed with diethyl ether, followed by addition of saturated sodium carbonate solution to adjust the pH to 4. The precipitates were formed and filtered. The filter cake was dried to obtain the title compound 1-(quinolin-4-ylthio)cyclobutanecarboxylic acid 1 (110 mg, a pale yellow solid), yield: 71%.

MS m/z (ESL): 260.1 [M+1]

$^1$H NMR (400 MHz, DMSO-d$_6$) δ 13.15 (s, 1H), 8.72 (d, J=4.8 Hz, 1H), 8.10 (d/=8.4 Hz, 1H), 8.01 (d, J=8.4 Hz, 1H), 7.81 (t, J=7.6 Hz, 1H), 7.66 (t, J=7.6 Hz, 1H), 7.16 (d, J=4.8 Hz, 1H), 2.92 (dt, J=12.8, 9.2 Hz, 2H), 2.45-2.30 (m, 2H), 2.30-2.20 (m, 1H), 2.10-1.95 (m, 1H).

Example 2

1-((6-(trifluoromethyl)quinolin-4-yl)thio)cyclobutanecarboxylic acid

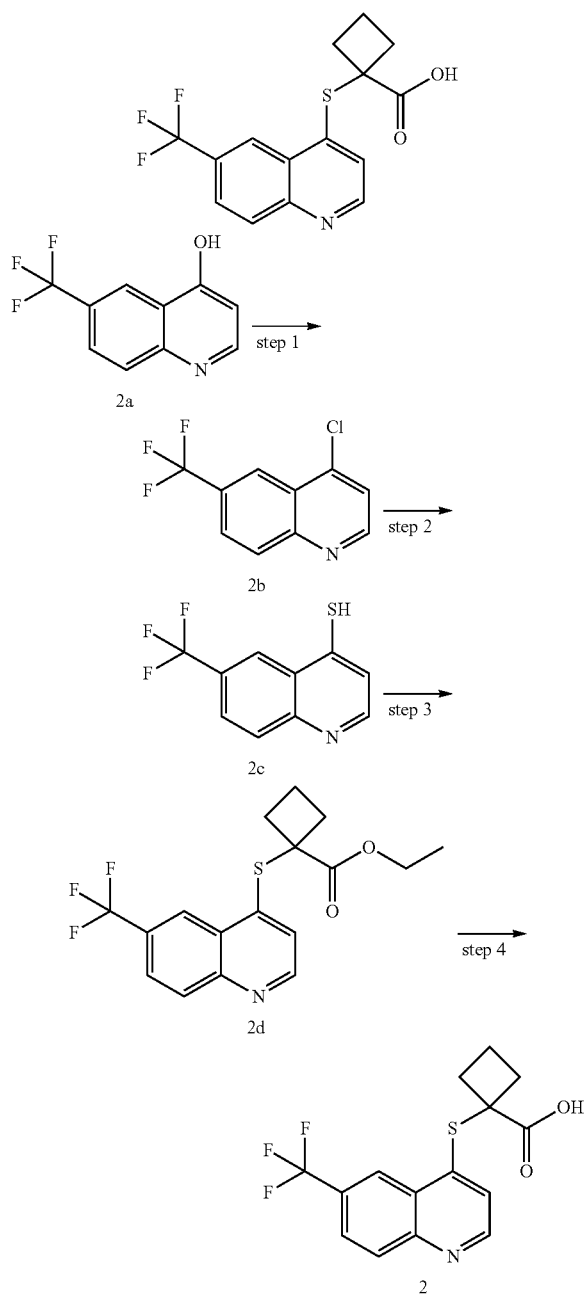

Step 1

4-chloro-6-(trifluoromethyl)quinoline 6-(trifluoromethyl)quinolin-4-ol 2a (50 mg, 0.2 mmol, prepared by a well known method disclosed in "*Bioorganic & Medicinal Chemistry Letters,* 2005, 15(4), 1015-1018") was added to phosphorus oxychloride (108 mg, 0.7 mmol). Upon completion of the addition, the reaction solution was heated to 90° C. and stirred for 2 hours, then added dropwise with a saturated solution of sodium bicarbonate to adjust the pH to 8~9, and extracted with ethyl acetate (30 mL×3). The organic phases were combined, and concentrated under reduced pressure to obtain the title compound 4-chloro-6-(trifluoromethyl)quinoline 2b (60 mg, a colorless oil), which was used directly in the next step.

Step 2

6-(trifluoromethyl)quinoline-4-thiol 4-chloro-6-(trifluoromethyl)quinoline 2b (50 mg, 0.2 mmol) and sodium sulphide (51 mg, 0.6 mmol) were added to 5 mL of N,N-dimethylformamide. Upon completion of the addition, the reaction solution was heated to 80° C. and stirred for 2 hours. The reaction solution was mixed with 50 mL of water and added dropwise with 1 M hydrochloric acid to adjust the pH to 5~6, then extracted with ethyl acetate (50 mL×3). The organic phases were combined, dried over anhydrous sodium sulfate and filtered. The filtrate was concentrated under reduced pressure to obtain the title compound 6-(trifluoromethyl)quinoline-4-thiol 2c (40 mg, a yellow solid), yield: 81%.

MS m/z (ESI): 230.1 [M+1]

Step 3

Ethyl 1-((6-(trifluoromethyl)quinolin-4-yl)thio)cyclobutanecarboxylate 6-(trifluoromethyl)quinoline-4-thiol 2c (40 mg, 0.17 mmol), ethyl 1-bromocyclobutanecarboxylate (43 mg, 0.21 mmol) and cesium carbonate (171 mg, 0.52 mmol) were added to 5 mL of N,N-dimethylformamide, successively. The reaction solution was heated to 60° C. and stirred for 2 hours, then concentrated under reduced pressure. The residue was mixed with 20 mL of water, stirred uniformly, and extracted with ethyl acetate (20 mL×3). The organic phases were combined, dried over anhydrous sodium sulfate, and filtered. The filtrate was concentrated under reduced pressure to obtain the title compound ethyl 1-((6-(trifluoromethyl)quinolin-4-yl)thio)cyclobutanecarboxylate 2d (10 mg, a pale yellow oil), which was used directly in the next step.

MS m/z (ESI): 356.1 [M+1]

$^1$H NMR (400 MHz, CDCl$_3$) δ 8.77 (d, J=4.77 Hz, 1H), 8.46 (s, 1H), 8.18 (d, J=8.78 Hz, 1H), 7.83-7.95 (m, 1H), 7.21 (d, J=5.02 Hz, 1H), 4.17 (q, J=7.1 Hz, 2H), 2.93-3.07 (m, 2H), 2.41-2.54 (m, 2H), 2.26-2.41 (m, 1H), 2.01-2.19 (m, 1H), 1.17 (t, J=7.15 Hz, 3H)

Step 4

1-((6-(trifluoromethyl)quinolin-4-yl)thio)cyclobutanecarboxylic acid

Ethyl 1-((6-(trifluoromethyl)quinolin-4-yl)thio)cyclobutanecarboxylate 2d (160 mg, 0.45 mmol) was dissolved in 6 mL of a mixture of methanol and water (V:V=1:1), followed by addition of sodium hydroxide (54 mg, 21.35 mmol). Upon completion of the addition, the reaction solution was stirred for 2 hours, then concentrated under reduced pressure. The residue was mixed with 20 mL of water, stirred uniformly, added dropwise with 1 M hydrochloric acid to adjust the pH to 5~6, and then extracted with ethyl acetate (20 mL×3). The organic phases were combined, dried over anhydrous sodium sulfate, and filtered. The filtrate was concentrated under reduced pressure and the residue was purified by thin layer chromatography with elution system A to obtain the title compound 1-((6-(trifluoromethyl)quinolin-4-yl)thio)cyclobutanecarboxylic acid 2 (10 mg, a pale yellow solid), yield: 6.8%.

MS m/z (ESI): 328.2 [M+1]

$^1$H NMR (400 MHz, DMSO-d$_6$) δ 8.88 (d, 1H), 8.40 (s, 1H), 8.23 (d, 1H), 8.08 (d, 1H) 7.32 (d, 1H), 2.88-2.95 (m, 2H), 2.35-2.42 (m, 2H), 2.22-2.24 (m, 1H), 2.02-2.04 (m, 1H)

Example 3

1-((6-bromoquinolin-4-yl)thio)cyclobutanecarboxylic acid

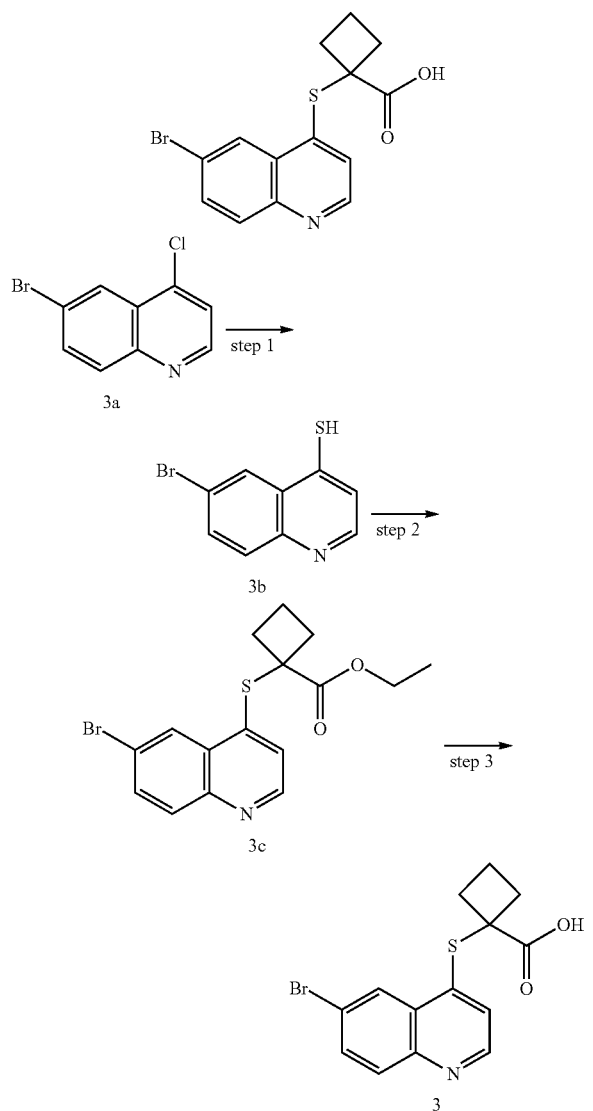

Step 1

6-bromoquinoline-4-thiol 6-bromo-4-chloroquinoline 3a (260 mg, 1.1 mmol, prepared by a well known method disclosed in "*Bioorganic & Medicinal Chemistry Letters,* 2012, 22(4), 1569-1574") and sodium sulphide (100 mg, 1.3 mmol) were added to 4 mL of N,N-dimethylformamide. Upon completion of the addition, the reaction solution was heated to 80° C. and stirred for 2 hours. The reaction solution was mixed with 50 mL of water, added dropwise with 1 M hydrochloric acid to adjust the pH to 5~6, and extracted with ethyl acetate (50 mL×3). The organic phases were combined, dried over anhydrous sodium sulfate, and filtered. The filtrate was concentrated under reduced pressure to obtain the title compound 6-bromoquinoline-4-thiol 3b (257 mg, a yellow oil), which was used directly in the next step.

Step 2

Ethyl 1-((6-bromoquinolin-4-yl)thio)cyclobutanecarboxylate

Under argon atmosphere, 6-bromoquinoline-4-thiol 3b (257 mg, 1.1 mmol), ethyl 1-bromocyclobutanecarboxylate (266 mg, 1.3 mmol) and cesium carbonate (371 mg, 1.1 mmol) were added to 5 mL of N,N-dimethylformamide, successively. The reaction solution was heated to 60° C. and stirred for 2 hours. The reaction solution was filtered and the filter cake was washed with ethyl acetate (10 mL×3). The filtrate was concentrated under reduced pressure to obtain the title compound ethyl 1-((6-bromoquinolin-4-yl)thio)cyclobutanecarboxylate 3c (300 mg, a brown oil), yield: 77%.

MS m/z (ESI): 368.2 [M+1]

$^1$H NMR (400 MHz, CDCl$_3$) δ 8.67 (d, J=4.77 Hz, 1H), 8.31 (d, J=2.13 Hz, 1H), 7.94 (d, J=8.91 Hz, 1H), 7.78 (dd, J=9.03, 2.13 Hz, 1H), 7.15 (d, J=4.89 Hz, 1H), 4.16 (q, J=7.15 Hz, 2H), 2.86-3.04 (m, 2H), 2.39-2.51 (m, 2H), 2.25-2.37 (m, 1H), 2.00-2.15 (m, 1H), 1.16 (t, J=7.09 Hz, 3H)

Step 3

1-((6-bromoquinolin-4-yl)thio)cyclobutanecarboxylic acid

Ethyl 1-((6-bromoquinolin-4-yl)thio)cyclobutanecarboxylate 3c (100 mg, 0.27 mmol) and lithium hydroxide monohydrate (23 mg, 0.55 mmol) were dissolved in 6 mL of a mixture of tetrahydrofuran, ethanol and water (V:V:V=4:1:1). After stirring for 3 hours, the reaction solution was added dropwise with 1 M hydrochloric acid to adjust the pH to 5~6. The reaction solution was separated, and the aqueous phase was extracted with dichloromethane (10 mL×3). The organic phases were combined, washed with saturated sodium chloride solution (10 mL×1), dried over anhydrous sodium sulfate, and filtered. The filtrate was concentrated under reduced pressure and the residue was purified by thin layer chromatography with elution system A to obtain the title compound 1-((6-bromoquinolin-4-yl)thio)cyclobutanecarboxylic acid 3 (20 mg, a white solid), yield: 22%.

MS m/z (ESI): 338.0 [M+1]

$^1$H NMR (400 MHz, DMSO) δ 13.17 (s, 1H), 8.75-8.79 (m, 1H), 8.24 (s, 1H), 7.87-7.98 (m, 2H), 7.21-7.25 (m, 1H), 2.83-2.95 (m, 2H), 2.30-2.41 (m, 2H), 2.16-2.27 (m, 1H), 1.97-2.08 (m, 1H)

Example 4

1-((6-methoxyquinolin-4-yl)thio)cyclobutanecarboxylic acid

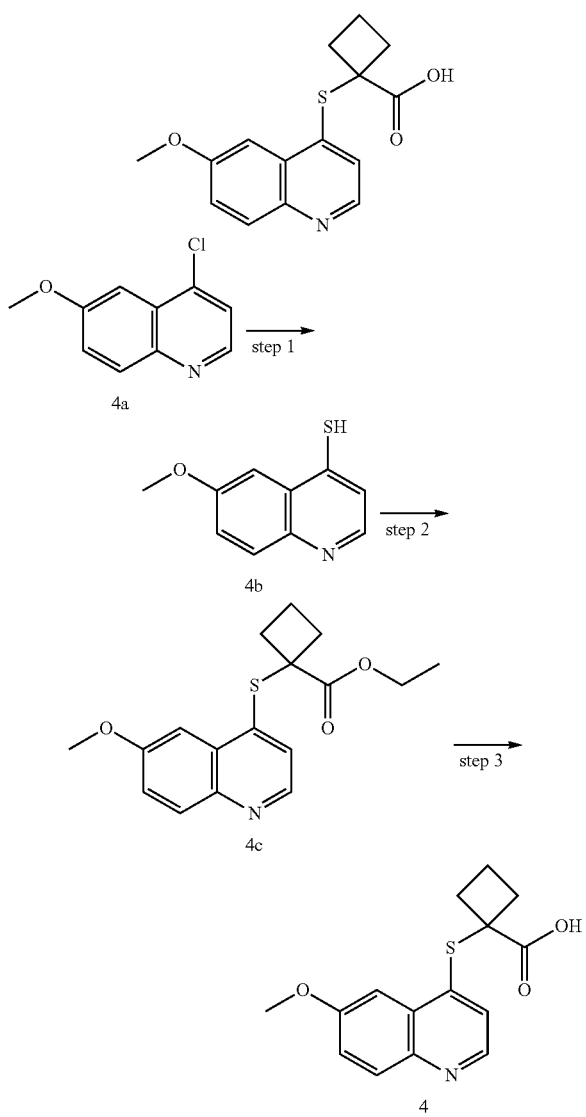

Step 1

6-methoxyquinoline-4-thiol 4-chloro-6-methoxyquinoline 4a (590 mg, 3.1 mmol, prepared by a method disclosed in International Patent Application Publication WO2003087098) and sodium sulfide (713 mg, 9.3 mmol) were added to 4 mL of N,N-dimethylformamide. Upon completion of the addition, the reaction solution was heated to 80° C. and stirred for 2 hours. The reaction solution was concentrated under reduced pressure and the residue was mixed with 5 mL of methanol, stirred uniformly, followed by addition of sodium borohydride (59 mg, 1.5 mmol). Upon completion of the addition, the reaction solution was stirred for 2 hours, and concentrated under reduced pressure. The residue was mixed with 10 mL of water, stirred uniformly, added dropwise with 1 M hydrochloric acid to adjust the pH to 5~6, and extracted with ethyl acetate (50 mL×3). The organic phases were combined, dried over anhydrous sodium sulfate, and filtered. The filtrate was concentrated under reduced pressure to obtain the title compound 6-methoxyquinoline-4-thiol 4b (477 mg, a yellow solid), which was used directly in the next step.

MS m/z (ESI): 192.2 [M+1]

Step 2

Ethyl 1-((6-methoxyquinolin-4-yl)thio)cyclobutanecarboxylate 6-methoxyquinoline-4-thiol 4b (477 mg, 2.5 mmol), ethyl 1-bromocyclobutanecarboxylate (620 mg, 2.9 mmol) and cesium carbonate (326 mg, 7.5 mmol) were added to 10 mL of N,N-dimethylformamide, successively. The reaction solution was heated to 60° C. and stirred for 2 hours. The reaction solution was mixed with 50 mL of water, and extracted with ethyl acetate (50 mL×4). The organic phases were combined, dried over anhydrous sodium sulfate, and filtered. The filtrate was concentrated under reduced pressure to obtain the title compound ethyl 1-((6-methoxyquinolin-4-yl)thio)cyclobutanecarboxylate 4c (620 mg, a brown oil), yield: 78%.

MS m/z (ESI): 318.2 [M+1]

Step 3

1-((6-methoxyquinolin-4-yl)thio)cyclobutanecarboxylic acid

Ethyl 1-((6-methoxyquinolin-4-yl)thio)cyclobutanecarboxylate 4c (50 mg, 0.15 mmol) and sodium hydroxide (19 mg, 0.47 mmol) were dissolved in 6 mL of a mixture of tetrahydrofuran, ethanol and water (V:V:V=4:1:1), and stirred for 16 hours. The reaction solution was evaporated under reduced pressure to remove tetrahydrofuran, added dropwise with 3 M hydrochloric acid to adjust the pH to 5~6, and extracted with dichloromethane (10 mL×3). The organic phases were combined, washed with saturated sodium chloride solution (10 mL×1), dried over anhydrous sodium sulfate, and filtered. The filtrate was concentrated under reduced pressure to obtain the title compound 1-((6-methoxyquinolin-4-yl)thio)cyclobutanecarboxylic acid 4 (10 mg, a yellow solid), yield: 22%.

MS m/z (ESI): 290.2 [M+1]

$^1$H NMR (400 MHz, CD$_3$OD) δ 8.45 (d, 1H), 7.91 (d, 1H), 7.42-7.45 (m, 2H), 7.33 (d, 1H), 3.96 (s, 3H), 2.96-3.04 (m, 2H), 2.43-2.47 (m, 2H), 2.30-2.33 (m, 1H), 2.09-2.11 (m, 1H)

Example 5

1-((6-(2-methoxyethoxy)quinolin-4-yl)thio)cyclobutanecarboxylic acid

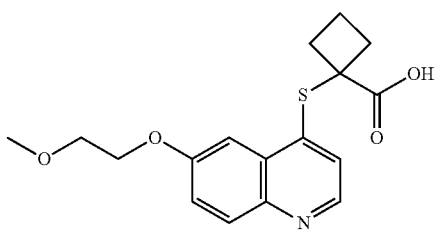

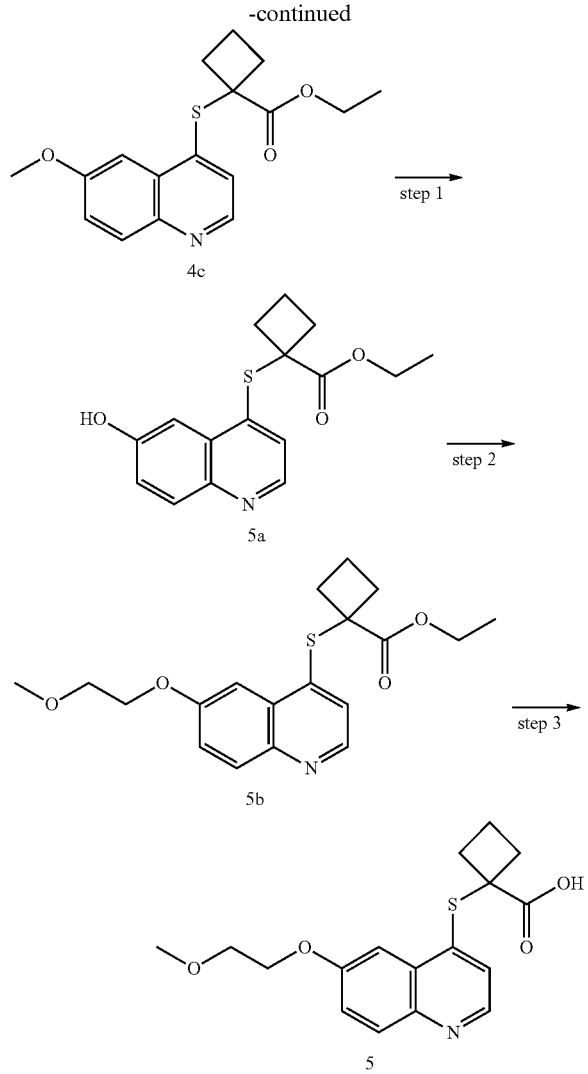

Step 1

Ethyl 1-((6-hydroxyquinolin-4-yl)thio)cyclobutanecarboxylate

Ethyl 1-((6-methoxyquinolin-4-yl)thio)cyclobutanecarboxylate 4c (200 mg, 0.63 mmol) was dissolved in 10 mL of dichloromethane, and added dropwise with a solution of boron bromide (400 mg, 1.58 mmol) in dichloromethane (5 mL). Upon completion of the addition, the reaction solution was stirred for 2 hours. The reaction solution was mixed with 30 mL of water, added dropwise with saturated sodium bicarbonate solution to adjust the pH to 8~9, and extracted with dichloromethane (50 mL×3). The organic phases were combined, washed with saturated sodium chloride solution, dried over anhydrous sodium sulfate, and filtered. The filtrate was concentrated under reduced pressure to obtain the title compound ethyl 1-((6-hydroxyquinolin-4-yl)thio)cyclobutanecarboxylate 5a (100 mg, a brown oil), which was used directly in the next step.

MS m/z (ESI): 304.2 [M+1]

Step 2

Ethyl 1-((6-(2-methoxyethoxy)quinolin-4-yl)thio)cyclobutanecarboxylate

Ethyl 1-((6-hydroxyquinolin-4-yl)thio)cyclobutanecarboxylate 5a (50 mg, 0.17 mmol), 1-bromo-2-methoxyethane (28 mg, 0.20 mmol) and potassium carbonate (34 mg, 0.25 mmol) were added to 5 mL of N,N-dimethylformamide, successively. The reaction solution was heated to 60° C. and stirred for 2 hours. The reaction solution was mixed with 50 mL of water, and extracted with ethyl acetate (50 mL×4). The organic phases were combined, washed with saturated sodium chloride solution, dried over anhydrous sodium sulfate, and filtered. The filtrate was concentrated under reduced pressure to obtain the title compound ethyl 1-((6-(2-methoxyethoxy)quinolin-4-yl)thio)cyclobutanecarboxylate 5b (40 mg, a brown oil), yield: 67%.

MS m/z (ESI): 362.2 [M+1]

Step 3

1-((6-(2-methoxyethoxy)quinolin-4-yl)thio)cyclobutanecarboxylic acid

Ethyl 1-((6-(2-methoxyethoxy)quinolin-4-yl)thio)cyclobutanecarboxylate 5b (40 mg, 0.11 mmol) and sodium hydroxide (11 mg, 0.28 mmol) were dissolved in 5 mL of a mixture of tetrahydrofuran and water (V:V=1:1), and stirred for 3 hours. The reaction solution was added with 10 mL of water, and washed with ethyl acetate. The aqueous phase was added dropwise with 2 M hydrochloric acid to adjust the pH to 5~6, and extracted with n-butanol (15 mL×3). The organic phases were combined, washed with saturated sodium chloride solution (10 mL×1), dried over anhydrous sodium sulfate, and filtered. The filtrate was concentrated under reduced pressure and the residue was purified by thin layer chromatography with elution system A to obtain the title compound 1-((6-(2-methoxyethoxy)quinolin-4-yl)thio)cyclobutanecarboxylic acid 5 (3 mg, a white solid), yield: 8.1%.

MS m/z (ESI): 334.3 [M+1]

$^1$H NMR (400 MHz, CD3OD) δ 8.46 (d, 1H), 7.89 (d, 1H), 7.47 (d, 1H), 7.44 (d, 1H), 7.34 (d, 1H), 4.28 (t, 2H), 3.84 (t, 2H), 3.46 (s, 3H), 2.96-3.02 (m, 2H), 2.30-2.46 (m, 3H), 2.07-2.16 (m, 1H)

Example 6

1-((6-(3-fluorophenyl)quinolin-4-yl)thio)cyclobutanecarboxylic acid

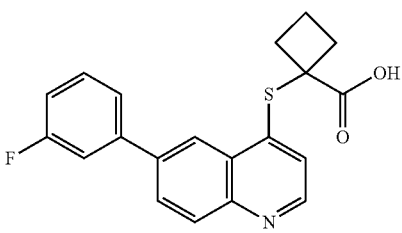

Step 2

1-((6-(3-fluorophenyl)quinolin-4-yl)thio)cyclobutanecarboxylic acid

Ethyl 1-((6-(3-fluorophenyl)quinolin-4-yl)thio)cyclobutanecarboxylate 6b (85 mg, 0.24 mmol) and lithium hydroxide monohydrate (20 mg, 0.48 mmol) were dissolved in 6 mL of a mixture of tetrahydrofuran, methanol and water (V:V:V=4:1:1). The reaction solution was stirred for 16 hours, added dropwise with 1 M hydrochloric acid to adjust the pH to 5~6, and extracted with dichloromethane (15 mL×3). The organic phases were combined, washed with saturated sodium chloride solution (10 mL×1), dried over anhydrous sodium sulfate, and filtered. The filtrate was concentrated under reduced pressure and the residue was purified by thin layer chromatography with elution system A to obtain the title compound 1-((6-(3-fluorophenyl)quinolin-4-yl)thio)cyclobutanecarboxylic acid 6 (10 mg, a yellow solid), yield: 13%.

MS m/z (ESI): 352.2 [M−1]

$^1$H NMR (400 MHz, DMSO) δ 13.30 (s, 1H), 8.56-8.60 (m, 1H), 8.22-8.26 (m, 1H), 8.0-8.10 (m, 2H), 7.56-7.68 (m, 4H), 7.24-7.32 (m, 1H), 2.80-2.91 (m, 2H), 2.03-2.21 (m, 3H), 1.84-1.95 (m, 1H)

Example 7

1-((6-(4-fluorophenyl)quinolin-4-yl)thio)cyclobutanecarboxylic acid

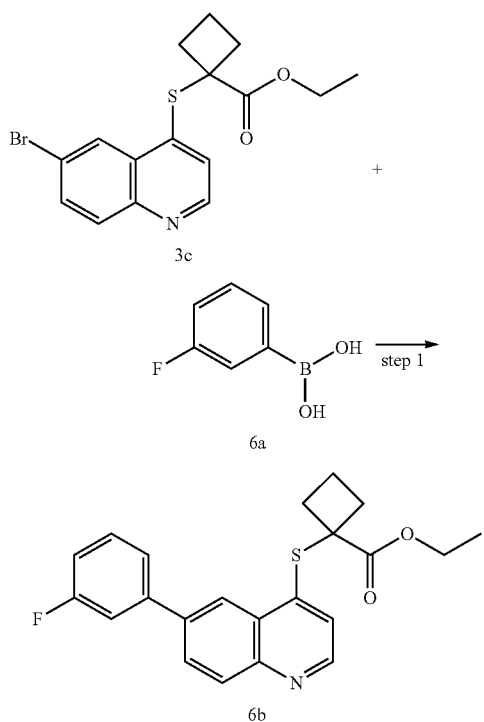

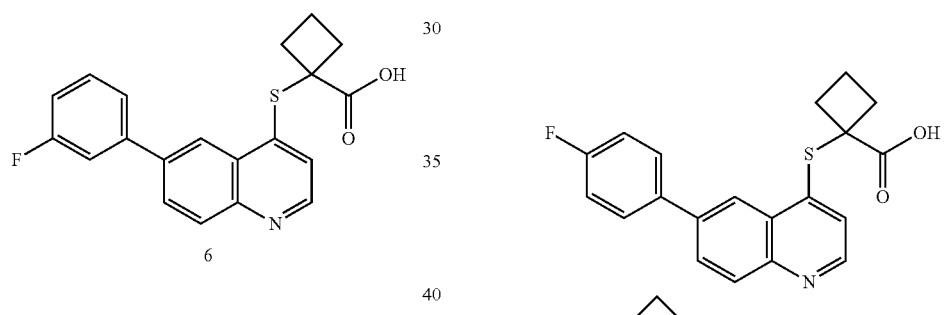

Step 1

Ethyl 1-((6-(3-fluorophenyl)quinolin-4-yl)thio)cyclobutanecarboxylate

Under argon atmosphere, ethyl 1-((6-bromoquinolin-4-yl)thio)cyclobutanecarboxylate 3c (100 mg, 0.27 mmol), (3-fluorophenyl)boronic acid 6a (46 mg, 0.33 mmol), [1,1'-Bis(diphenylphosphino)ferrocene]dichloropalladium (20 mg, 0.03 mmol) and sodium carbonate (43 mg, 0.41 mmol) were added to 5 mL of a mixture of 1,4-dioxane and water (V:V=4:1), successively. Upon completion of the addition, the reaction solution was heated to 90° C. and stirred for 16 hours. The reaction solution was filtered and the filtrate was mixed with 10 mL of water, stirred uniformly, and extracted with dichloromethane (15 mL×3). The organic phases were combined, washed with saturated sodium chloride solution, dried over anhydrous sodium sulfate, and filtered. The filtrate was concentrated under reduced pressure to obtain the title compound ethyl 1-((6-(3-fluorophenyl)quinolin-4-yl)thio)cyclobutanecarboxylate 6b (85 mg, a black oil), yield: 89%.

MS m/z (ESI): 382.0 [M+1]

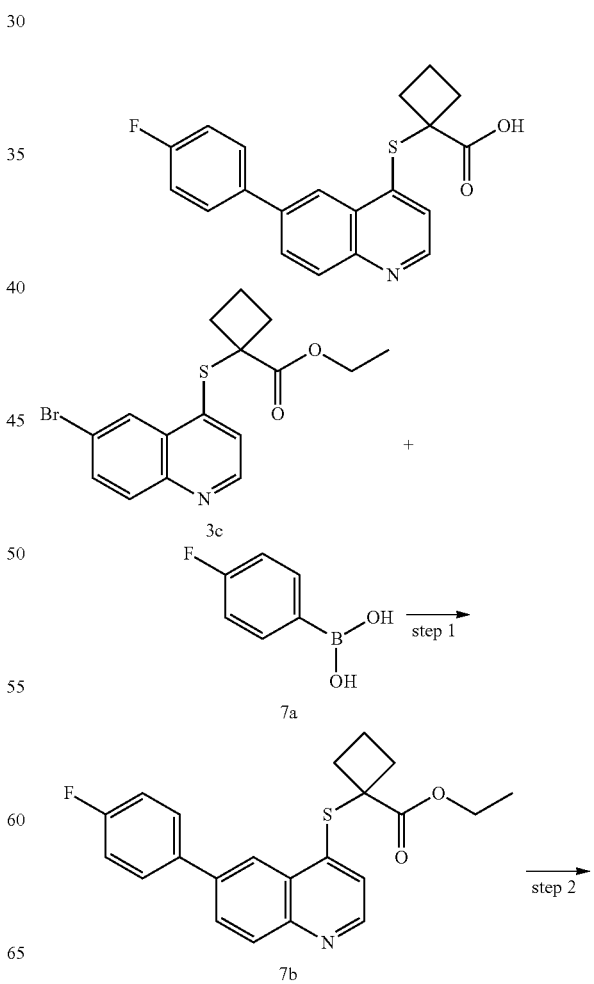

-continued

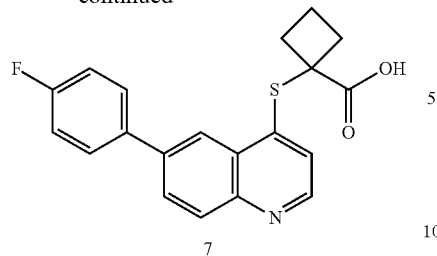

7

Step 1

Ethyl 1-((6-(4-fluorophenyl)quinolin-4-yl)thio)cyclobutanecarboxylate

Under argon atmosphere, ethyl 1-((6-bromoquinolin-4-yl)thio)cyclobutanecarboxylate 3c (100 mg, 0.27 mmol), (4-fluorophenyl)boronic acid 7a (46 mg, 0.33 mmol), [1,1'-bis(diphenylphosphino)ferrocene]dichloropalladium (20 mg, 0.03 mmol) and sodium carbonate (43 mg, 0.41 mmol) were added to 5 mL of a mixture of 1,4-dioxane and water (V:V=4:1), successively. Upon completion of the addition, the reaction solution was heated to 90° C. and stirred for 16 hours. The reaction solution was filtered and the filtrate was mixed with 10 mL of water, stirred uniformly, and extracted with dichloromethane (15 mL×3). The organic phases were combined and washed with saturated sodium chloride solution, dried over anhydrous sodium sulfate, and filtered. The filtrate was concentrated under reduced pressure to obtain the title compound ethyl 1-((6-(4-fluorophenyl)quinolin-4-yl)thio)cyclobutanecarboxylate 7b (90 mg, a black oil), yield: 87%.

MS m/z (ESI): 382.0 [M+1]

Step 2

1-((6-(4-fluorophenyl)quinolin-4-yl)thio)cyclobutanecarboxylic acid

Ethyl 1-((6-(4-fluorophenyl)quinolin-4-yl)thio)cyclobutanecarboxylate 7b (90 mg, 0.24 mmol) and lithium hydroxide monohydrate (20 mg, 0.48 mmol) were dissolved in 6 mL of a mixture of tetrahydrofuran, methanol and water (V:V:V=4:1:1). The reaction solution was stirred for 16 hours, added dropwise with 1 M hydrochloric acid to adjust the pH to 5-6, and extracted with dichloromethane (15 mL×3). The organic phases were combined, washed with saturated sodium chloride solution (10 mL×1), dried over anhydrous sodium sulfate, and filtered. The filtrate was concentrated under reduced pressure and the residue was purified by thin layer chromatography with elution system A to obtain the title compound 1-((6-(4-fluorophenyl)quinolin-4-yl)thio)cyclobutanecarboxylic acid 7 (10 mg, a yellow solid), yield: 12%.

MS m/z (ESI): 354.3 [M+1]

$^1$H NMR (400 MHz, DMSO) δ 13.20 (s, 1H), 8.60-8.64 (m, 1H), 8.18-8.23 (m, 1H), 8.03-8.07 (m, 2H), 7.83-7.88 (m, 2H), 7.43-7.47 (m, 1H), 7.31-7.39 (m, 2H), 2.83-2.95 (m, 2H), 2.19-2.30 (m, 2H), 2.07-2.18 (m, 1H), 1.89-2.0 (m, 1H)

Example 8

1-((6-(3-(trifluoromethyl)phenyl)quinolin-4-yl)thio)cyclobutanecarboxylic acid

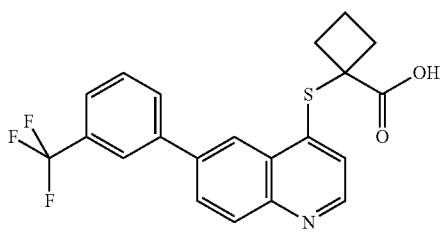

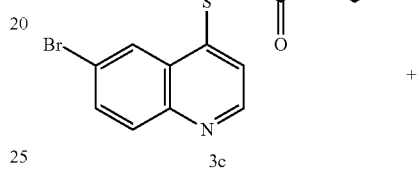

3c

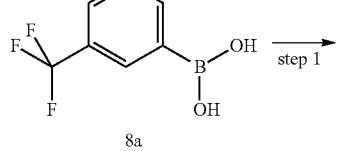

8a

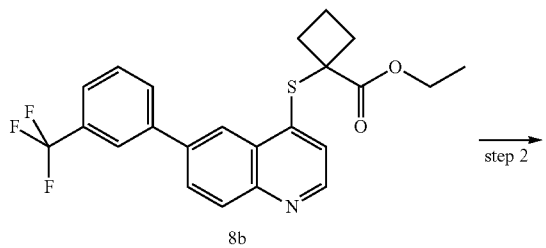

8b

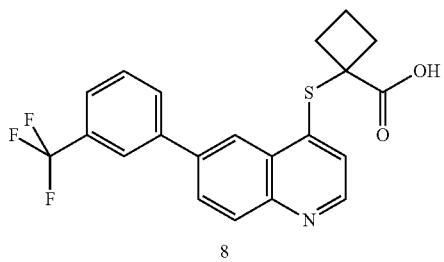

8

Step 1

Ethyl 1-((6-(3-(trifluoromethyl)phenyl)quinolin-4-yl)thio)cyclobutanecarboxylate Under argon atmosphere, ethyl 1-((6-bromoquinolin-4-yl)thio)cyclobutanecarboxylate 3c (150 mg, 0.41 mmol), (3-(trifluoromethyl)phenyl)boronic acid 8a (93 mg, 0.49 mmol), [1, L-bis(diphenylphosphino)ferrocene]dichloropalladium (30 ma, 0.04 mmol) and sodium carbonate (65 mg, 0.62 mmol) were added to 5 mL of a mixture of 1,4-dioxane and water (V:V=4:1), successively. Upon completion of the addition, the reaction solution was heated to 90° C. and stirred for 16 hours. The reaction solution was filtered and the filtrate was added with 10 mL of water, stirred uniformly, extracted with dichloromethane (15 mL×3). The organic phases were combined and washed with saturated sodium chloride solution, dried over anhydrous sodium sulfate, and filtered. The filtrate was concentrated under reduced pressure to obtain the title compound ethyl 1-((6-(3-(trifluoromethyl)phenyl)quinolin-4-yl)thio)cyclobutanecarboxylate 8b (150 mg, a brown oil), yield: 85%.

MS m/z (ESI): 432.3 [M+1]

Step 2

1-((6-(3-(trifluoromethyl)phenyl)quinolin-4-yl)thio)cyclobutanecarboxylic acid

Ethyl 1-((6-(3-(trifluoromethyl)phenyl)quinolin-4-yl)thio)cyclobutanecarboxylate 8b (150 mg, 0.35 mmol) and sodium hydroxide (28 mg, 0.70 mmol) were dissolved in 6 mL of a mixture of tetrahydrofuran, methanol and water (V:V:V=4:1:1). The reaction solution was stirred for 16 hours, added dropwise with 1 M hydrochloric acid to adjust the pH to 5~6, and extracted with dichloromethane (15 mL×3). The organic phases were combined, washed with saturated sodium chloride solution (10 mL×1), dried over anhydrous sodium sulfate, and filtered. The filtrate was concentrated under reduced pressure and the residue was purified by thin layer chromatography with elution system A to obtain the title compound 1-((6-(3-(trifluoromethyl)phenyl)quinolin-4-yl)thio)cyclobutanecarboxylic acid 8 (10 mg, a yellow solid), yield: 7%.

MS m/z (ESI): 404.3 [M+1]

$^1$H NMR (400 MHz, DMSO) δ 13.09 (s, 1H), 8.78-8.86 (m, 1H), 8.33-8.38 (m, 1H), 8.22-8.31 (m, 1H), 8.08-8.18 (m, 3H), 7.75-7.87 (m, 2H), 7.25-7.29 (m, 1H), 2.90-3.02 (m, 2H), 2.35-2.48 (m, 2H), 2.21-2.32 (m, 1H), 1.99-2.12 (m, 1H)

Example 9

1-((6-(methoxymethyl)quinolin-4-yl)thio)cyclobutanecarboxylic acid

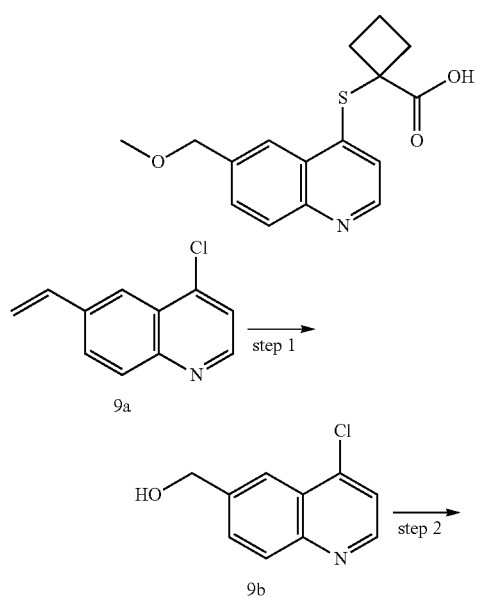

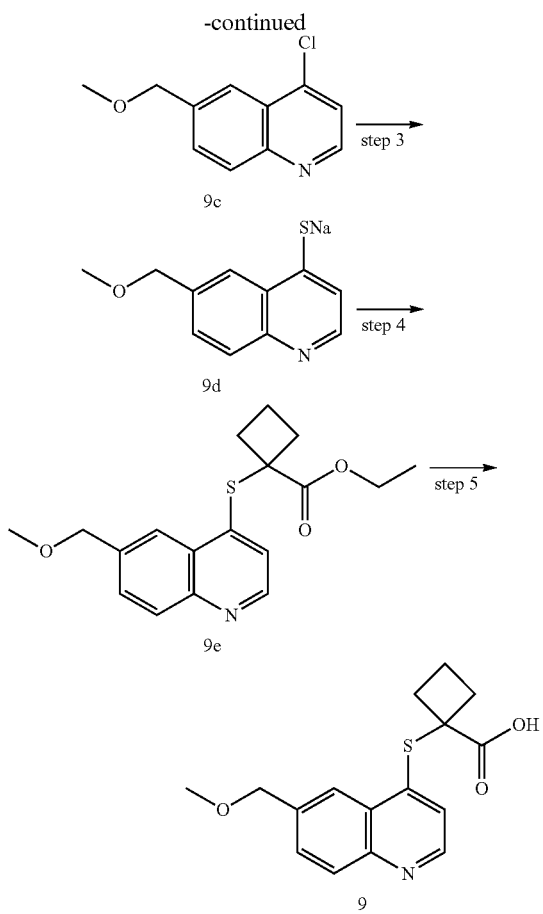

Step 1

(4-chloroquinolin-6-yl)methanol 4-chloro-6-vinylquinoline 9a (300 mg, 1.6 mmol, prepared by a method disclosed in International Patent Application Publication WO2006132739) was dissolved in 40 mL of a mixture of methanol and dichloromethane (V:V=1:3). The reaction solution was purged with ozone three times and stirred for 3 hours in a dry ice-acetone bath (−78° C.). After air replacement, the reaction solution was stirred for 0.5 hours, followed by addition of sodium borohydride (240 mg, 6.4 mmol). The dry ice-acetone bath was removed, and the reaction solution was warmed to room temperature and stirred for 0.5 hours. The reaction solution was mixed with 20 mL of saturated ammonium chloride solution, left to stand and separate, and the aqueous phase was extracted with dichloromethane (50 mL×3). The organic phases were combined, washed with saturated sodium chloride solution (50 mL×1), dried over anhydrous sodium sulfate, and filtered. The filtrate was concentrated under reduced pressure to obtain the title compound (4-chloroquinolin-6-yl)methanol 9b (200 mg, a white solid), yield: 67%.

MS m/z (ESI): 194.1 [M+1]

Step 2

4-chloro-6-(methoxymethyl)quinoline (4-chloroquinolin-6-yl)methanol 9b (100 mg, 0.52 mmol) was dissolved in 3 mL of tetrahydrofuran in an ice bath (0°

C.), sodium hydride (19 mg, 0.78 mmol) was added, and the reaction solution was stirred for 10 minutes, followed by addition of iodomethane (221 mg, 1.56 mmol). Upon completion of the addition, the ice bath was removed, and the reaction solution was slowly warmed up to room temperature, and stirred for 2 hours. The reaction solution was concentrated under reduced pressure, and the residue was dissolved in 50 mL of ethyl acetate, washed with saturated sodium chloride solution (10 mL×3), dried over anhydrous magnesium sulfate, and filtered. The filtrate was concentrated under reduced pressure to obtain the title compound 4-chloro-6-(methoxymethyl)quinoline 9c (108 mg, a white solid), which was used directly in the next step.

MS m/z (ESI): 208.1 [M+1]

Step 3

Sodium 6-(methoxymethyl)quinoline-4-thiolate

Under argon atmosphere, 4-chloro-6-(methoxymethyl) quinoline 9c (108 mg, 0.52 mmol) and sodium sulfide (48 mg, 0.62 mmol) were added to 5 mL of N,N-dimethylformamide. Upon completion of the addition, the reaction solution was heated to 80° C. and stirred for 2 hours. The reaction mixture of sodium 6-(methoxymethyl)quinoline-4-thiolate 9d in DMF was used directly in the next step.

MS m/z (ESI): 306.1 [M+1]

Step 4

Ethyl 1-((6-(methoxymethyl)quinolin-4-yl)thio)cyclobutanecarboxylate

Under argon atmosphere, ethyl 1-bromocyclobutanecarboxylate (128 mg, 0.62 mmol) was added to the mixture of sodium 6-(methoxymethyl)quinoline-4-thiolate 9d (118 mg, 0.52 mmol) in N,N-dimethylformamide, which was pre-prepared in step 3. Upon completion of the addition, the reaction solution was heated to 80° C., stirred for 4 hours and concentrated under reduced pressure to obtain the title compound ethyl 1-((6-(methoxymethyl)quinolin-4-yl)thio) cyclobutanecarboxylate 9e (172 mg, a brown solid), which was used directly in the next step.

MS m/z (ESI): 332.1 [M+1]

Step 5

1-((6-(methoxymethyl)quinolin-4-yl)thio)cyclobutanecarboxylic acid

Ethyl 1-((6-(methoxymethyl)quinolin-4-yl)thio)cyclobutanecarboxylate 9e (172 mg, 0.52 mmol) and lithium hydroxide monohydrate (87 mg, 2.08 mmol) were dissolved in 4 mL of a mixture of tetrahydrofuran and water (V:V=1: 1). The reaction solution was stirred for 16 hours, and added dropwise with 1 M hydrochloric acid to adjust the pH to 5~6. The organic phase was concentrated under reduced pressure and the residue was purified by thin layer chromatography with elution system A to obtain the title compound 1-((6-(methoxymethyl)quinolin-4-yl)thio)cyclobutanecarboxylic acid 9 (3 mg, a white solid), the yield of four steps: 2%.

MS m/z (ESI): 304.2 [M+1]

$^1$H NMR (400 MHz, CDCl$_3$) δ 8.59 (s, 1H), 7.95-8.10 (m, 2H), 7.55-7.70 (d, 1H), 7.28-7.34 (d, 1H), 4.58 (s, 2H), 3.41 (s, 3H), 3.01-3.16 (m, 2H), 2.36-2.49 (m, 2H), 2.21-2.35 (m, 1H), 2.05-2.20 (m, 1H)

Example 10

1-((4-cyanonaphthalen-1-yl)thio)cyclobutanecarboxylic acid

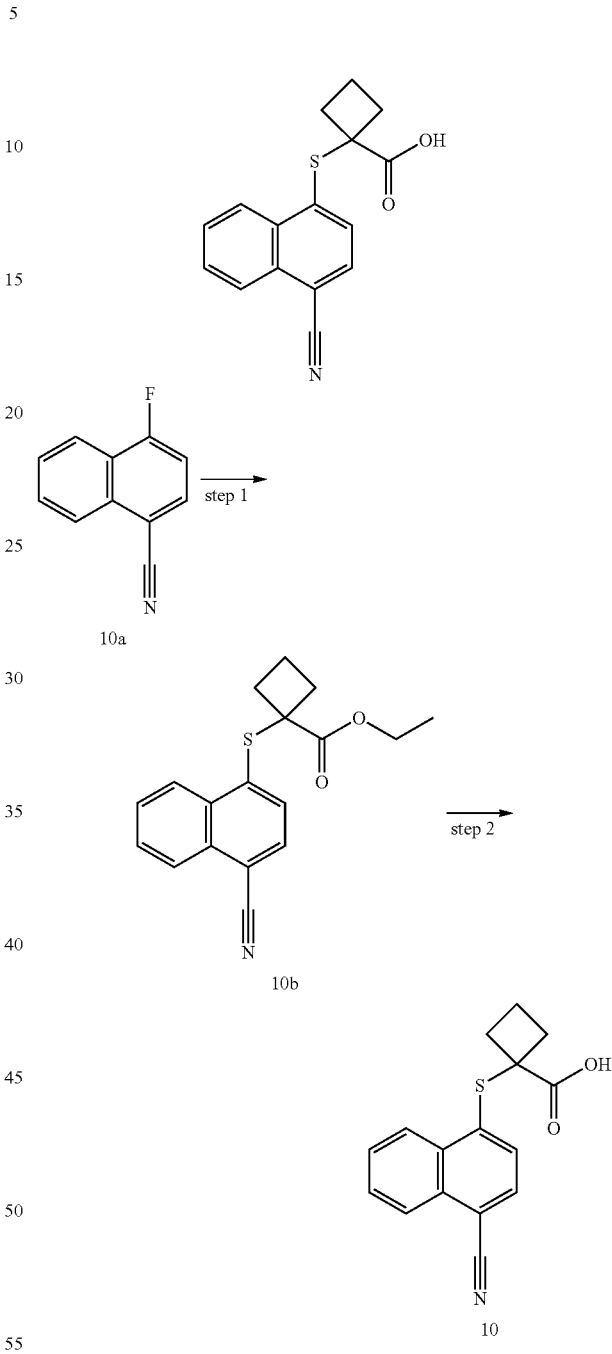

Step 1

Ethyl 1-((4-cyanonaphthalen-1-yl)thio)cyclobutanecarboxylate 4-fluoro-1-naphthonitrile 10a (60 mg, 0.35 mmol) and sodium sulfide (30 mg, 0.38 mmol) were added to 0.8 mL of N,N-dimethylformamide. Upon completion of the addition, the reaction solution was stirred for 24 hours at room temperature. The reaction process was monitored by LC-MS until completion of the reaction, and a DMF solution of sodium 4-cyanonaphthalen-thiolate was obtained, and used directly in the next step. Ethyl 1-bromocyclobutanecarboxylate (60 mg, 0.32 mmol) was directly added to the pre-prepared DMF solution of 4-cyanonaphthalen-thiolate. The reaction solution was heated to 60° C., and the reaction process was monitored by LC-MS until completion of the reaction. The reaction solution was mixed with 20 mL of water, and extracted with ethyl acetate (30 mL×3). The organic phases were combined, and washed with saturated sodium chloride solution. The organic phase was separated, and concentrated under reduced pressure to obtain the title compound ethyl 1-((4-cyanonaphthalen-1-yl)thio)cyclobutanecarboxylate 10b (127 mg, a brown solid), which was used directly in the next step.

MS m/z (ESI): 312.1 [M+1]

Step 2

1-((4-cyanonaphthalen-1-yl)thio)cyclobutanecarboxylic acid

Ethyl 1-((4-cyanonaphthalen-1-yl)thio)cyclobutanecarboxylate 10b (127 mg, 0.41 mmol) and lithium hydroxide monohydrate (69 mg, 1.64 mmol) were dissolved in 1.5 mL of a mixture of tetrahydrofuran and water (V:V=2:1), and the reaction solution was stirred for 3 hours. The reaction process was monitored by LC-MS until completion of the reaction. The reaction solution was evaporated under reduced pressure to remove tetrahydrofuran, and mixed with 10 mL of water. The aqueous phase was washed with diethyl ether, added dropwise with 1 M diluted hydrochloric acid to adjust the pH to 2, and extracted with dichloromethane (15 mL×3). The organic phases were combined, and washed with saturated sodium chloride solution. The organic phase was separated, and concentrated under reduced pressure. The residue was purified by thin layer chromatography with elution system A to obtain the title compound 1-((4-cyanonaphthalen-1-yl)thio)cyclobutanecarboxylic acid 10 (5 mg, a pale yellow solid), the yield of two steps: 4%.

MS m/z (ESI): 282.1 [M−1]
$^1$H NMR (400 MHz, CDCl$_3$) δ 8.44 (d, J=8.2 Hz, 1H), 8.27 (d, J=8.0 Hz, 1H), 7.82 (d, J=7.4 Hz, 1H), 7.72 (dt, J=23.9, 7.3 Hz, 2H), 7.41 (d, J=7.4 Hz, 1H), 3.06-2.85 (m, 2H), 2.54-2.30 (m, 3H), 2.16-2.00 (m, 1H)

Example 11

1-((1,6-naphthyridin-4-yl)thio)cyclobutanecarboxylic acid

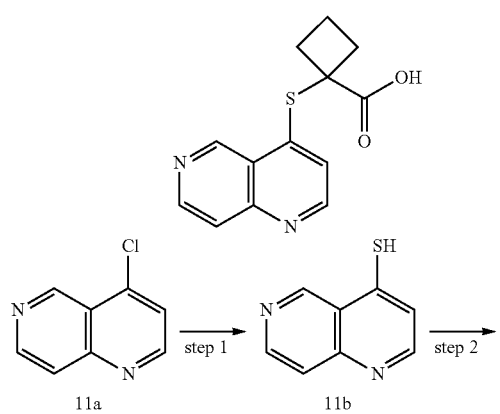

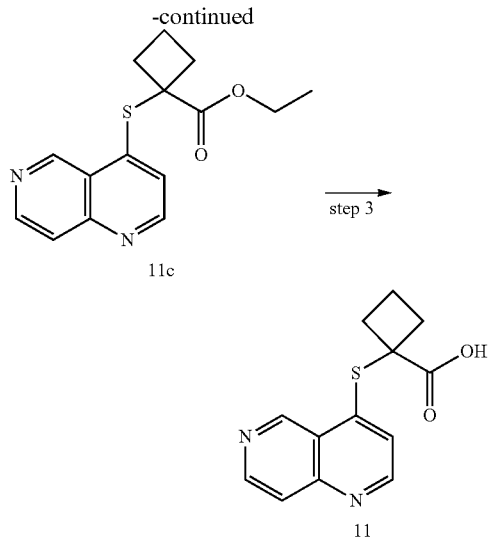

Step 1

1,6-naphthyridine-4-thiol 4-chloro-1,6-naphthyridine 11a (60 mg, 0.36 mmol, prepared by a method disclosed in International Patent Application Publication WO2008124083) was dissolved in 2 mL of N,N-dimethylformamide, followed by addition of sodium sulfide (30 mg, 0.40 mmol). Upon completion of the addition, the reaction solution was heated to 70° C. and stirred for 5 hours. The reaction solution was concentrated under reduced pressure, and the residue was mixed with 5 mL of methanol, stirred uniformly, and sodium borohydride (12 mg, 0.3 mmol) was added. Upon completion of the addition, the reaction solution was stirred for 2 hours, and concentrated under reduced pressure. The residue was mixed with 10 mL of water, stirred uniformly, added dropwise with 1 M hydrochloric acid to adjust the pH to 5~6, and extracted with ethyl acetate (50 mL×3). The organic phases were combined, dried over anhydrous sodium sulfate, and filtered. The filtrate was concentrated under reduced pressure to obtain the title compound 1,6-naphthyridine-4-thiol 11b (58 mg, a yellow oil), which was used directly in the next step.

MS m/z (ESI): 161.1 [M−1]

Step 2

Ethyl 1-((1,6-naphthyridin-4-yl)thio)cyclobutanecarboxylate

Under argon atmosphere, 1,6-naphthyridine-4-thiol 11b (58 mg, 0.32 mmol) was dissolved in 3 mL of N,N-dimethylformamide, followed by addition of ethyl 1-bromocyclobutanecarboxylate (98 mg, 0.47 mmol). Upon completion of the addition, the reaction solution was heated to 70° C. and stirred for 16 hours. The reaction solution was mixed with 20 mL of water, and extracted with dichloromethane (30 mL×3). The organic phases were combined, washed with saturated sodium chloride solution, dried over anhydrous sodium sulfate, and filtered. The filtrate was concentrated under reduced pressure to obtain the title compound ethyl 1-((1,6-naphthyridin-4-yl)thio)cyclobutanecarboxylate 11c (50 mg, a brown solid), which was used directly in the next step.

MS m/z (ESI): 289.2 [M+1]

Step 3

1-((1,6-naphthyridin-4-yl)thio)cyclobutanecarboxylic acid

Ethyl 1-((1,6-naphthyridin-4-yl)thio)cyclobutanecarboxylate 11c (50 mg, 0.17 mmol) was dissolved in 4 mL of a mixture of methanol and water (V:V=1:1), followed by addition of sodium hydroxide (28 mg, 0.68 mmol). Upon completion of the addition, the reaction solution was heated to 50° C. and stirred for 16 hours. The reaction solution was evaporated under reduced pressure to remove methanol, mixed with 10 mL of water, added dropwise with 1 M hydrochloric acid to adjust the pH to 4, and extracted with dichloromethane (30 mL×3). The organic phases were combined, washed with saturated sodium chloride solution, dried over anhydrous sodium sulfate, and filtered. The filtrate was concentrated under reduced pressure, and the residue was washed with 1 mL of a mixture of methanol and water (V:V=1:1) to obtain the title compound 1-((1,6-naphthyridin-4-yl)thio)cyclobutanecarboxylic acid 11 (8 mg, a brown solid), the yield of three steps: 9%.

MS m/z (ESI): 261.1 [M+1]

$^1$H NMR (400 MHz, DMSO) δ 13.28 (s, 1H), 9.50 (s, 1H), 8.91 (d, J=4.8 Hz, 1H), 8.78 (d, J=5.8 Hz, 1H), 7.90 (d, J=5.8 Hz, 1H), 7.27 (d, 0.1=4.8 Hz, 1H), 3.04-2.83 (m, 2H), 2.46-2.34 (m, 2H), 2.30-2.20 (m, 1H), 2.12-1.93 (m, 1H)

Example 12

1-((6-fluoroquinolin-4-yl)thio)cyclobutanecarboxylic acid

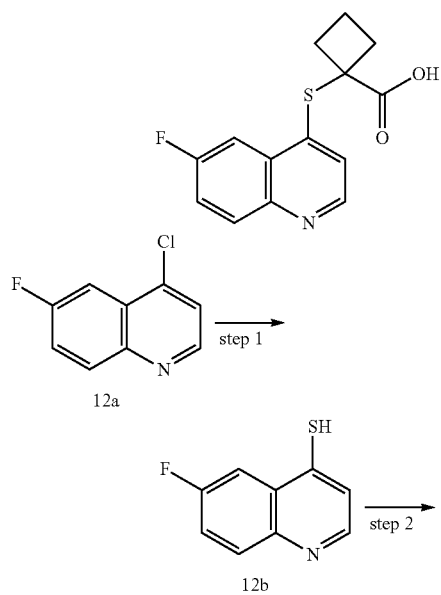

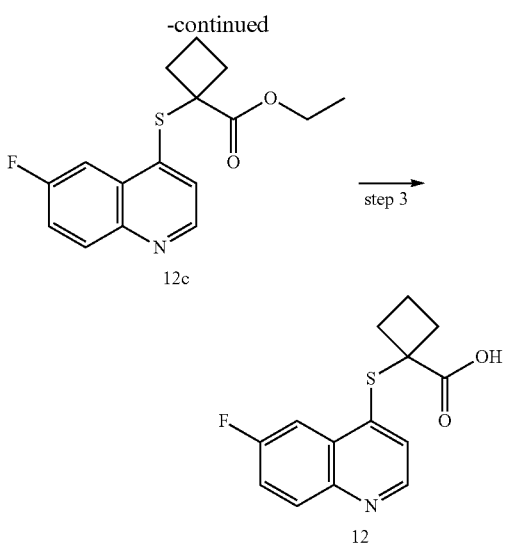

Step 1

6-fluoroquinoline-4-thiol

Under argon atmosphere, 6-fluoro-4-chloroquinoline 12a (100 mg, 0.55 mmol, prepared by a well known method disclosed in "Indian Journal of Heterocyclic Chemistry, 2006, 15 (3), 253-258") and sodium sulfide (129 mg, 1.65 mmol) were added to 5 mL of N,N-dimethylformamide. Upon completion of the addition, the reaction solution was heated to 80° C. and stirred for 2 hours. The reaction solution was concentrated under reduced pressure, mixed with 10 mL of water, added dropwise with 1 M hydrochloric acid to adjust the pH to 5~6, and extracted with ethyl acetate (30 mL×3). The organic phases were combined, washed with saturated sodium chloride solution, dried over anhydrous sodium sulfate, and filtered. The filtrate was concentrated under reduced pressure to obtain the title compound 6-fluoroquinoline-4-thiol 12b (100 mg, a yellow solid), which was used directly in the next step.

Step 2

Ethyl 1-((6-fluoroquinolin-4-yl)thio)cyclobutanecarboxylate 6-fluoroquinoline-4-thiol 12b (100 mg, 0.56 mmol), ethyl 1-bromocyclobutanecarboxylate (139 mg, 0.67 mmol) and cesium carbonate (545 mg, 1.67 mmol) were added to 5 mL of N,N-dimethylformamide, successively. The reaction solution was heated to 60° C. and stirred for 2 hours. The reaction solution was concentrated under reduced pressure, mixed with 20 mL of water, stirred uniformly, and extracted with ethyl acetate (30 mL×3). The organic phases were combined, washed with saturated sodium chloride solution, dried over anhydrous sodium sulfate, and filtered. The filtrate was concentrated under reduced pressure to obtain the title compound ethyl 1-((6-fluoroquinolin-4-yl)thio)cyclobutanecarboxylate 12c (100 mg, a yellow oil), yield: 59%.

MS m/z (ESI): 306.1 [M+1]

Step 3

1-((6-fluoroquinolin-4-yl)thio)cyclobutanecarboxylic acid

Ethyl 1-((6-fluoroquinolin-4-yl)thio)cyclobutanecarboxylate 12c (100 mg, 0.30 mmol) and sodium hydroxide (39 mg, 0.98 mmol) were dissolved in 6 mL of a mixture of tetrahydrofuran, ethanol and water (V:V:V=4:1:1). After stirring for 2 hours, the reaction solution was concentrated under reduced pressure, mixed with 20 mL of water, stirred uniformly, added dropwise with 1 M hydrochloric acid to adjust the pH to 5~6, and extracted with ethyl acetate (30 mL×3). The organic phases were combined, washed with saturated sodium chloride solution (10 mL×1), dried over anhydrous sodium sulfate, and filtered. The filtrate was concentrated under reduced pressure, and the residue was purified by silica gel column chromatography with elution system A to obtain the title compound 1-((6-fluoroquinolin-4-yl)thio)cyclobutanecarboxylic acid 12 (10 mg, a white solid), yield: 11%.

MS m/z (ESI): 278.1 [M+1]

$^1$H NMR (400 MHz, CD$_3$OD) δ 8.52 (s, 1H), 7.97-8.01 (m, 1H), 7.81-7.84 (m, 1H), 7.57-7.59 (m, 1H), 7.46 (s, 1H), 2.94-3.02 (m, 2H), 2.23-2.28 (m, 2H), 1.94-2.07 (m, 2H)

Example 13

1-((6-(2-methoxy-2-oxoethoxy)quinolin-4-yl)thio)cyclobutanecarboxylic acid

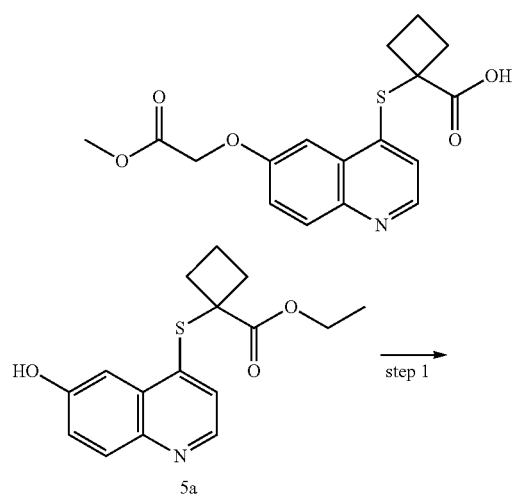

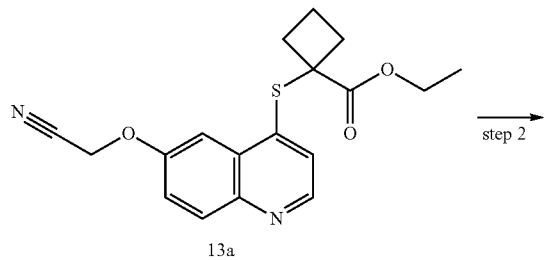

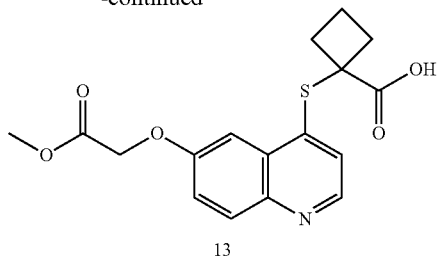

Step 1

Ethyl 1-((6-(cyanomethoxy)quinolin-4-yl)thio)cyclobutanecarboxylate

Ethyl 1-((6-hydroxyquinolin-4-yl)thio)cyclobutanecarboxylate 5a (50 mg, 0.17 mmol), bromoacetonitrile (24 mg, 0.20 mmol) and potassium carbonate (34 mg, 0.25 mmol) were added to 5 mL of ATA-dimethylformamide, successively. Upon completion of the addition, the reaction solution was heated to 60° C. and stirred for 2 hours. The reaction solution was mixed with 20 mL of water, and extracted with ethyl acetate (30 mL×3). The organic phases were combined, dried over anhydrous sodium sulfate, and filtered. The filtrate was concentrated under reduced pressure, and the residue was purified by silica gel column chromatography with elution system C to obtain the title compound ethyl 1-((6-(cyanomethoxy)quinolin-4-yl)thio)cyclobutanecarboxylate 13a (35 mg, a colourless oil), yield: 63%.

MS m/z (ESI): 343.1 [M−1]

Step 2

1-((6-(2-methoxy-2-oxoethoxy)quinolin-4-yl)thio)cyclobutanecarboxylic acid

Ethyl 1-((6-(cyanomethoxy)quinolin-4-yl)thio)cyclobutanecarboxylate 13a (35 mg, 0.10 mmol) was dissolved in 6 mL of a mixture of tetrahydrofuran, methanol and water (V:V:V=4:1:1), followed by addition of sodium hydroxide (6 mg, 0.15 mmol). The reaction solution was stirred for 2 hours, evaporated under reduced pressure to remove tetrahydrofuran, mixed with 10 mL of water, added dropwise with 2 M hydrochloric acid to adjust the pH to 5~6, and extracted with ethyl acetate (20 mL×3). The organic phases were combined, washed with saturated sodium chloride solution, dried over anhydrous sodium sulfate, and filtered. The filtrate was concentrated under reduced pressure, and the residue was purified by thin layer chromatography with elution system A to obtain the title compound 1-((6-(2-methoxy-2-oxoethoxy)quinolin-4-yl)thio)cyclobutanecarboxylic acid 13 (3 mg, an off-white solid), yield: 9%.

MS m/z (ESI): 348.2 [M+1]

$^1$H NMR (400 MHz, DMSO) δ 8.80 (d, 1H), 8.17 (d, 1H), 7.75 (d, 1H), 7.43 (d, 1H), 7.33 (d, 1H), 5.10 (s, 2H), 3.78 (s, 3H), 2.94-3.06 (m, 2H), 2.38-2.46 (m, 2H), 2.23-2.31 (m, 1H), 2.02-2.12 (m, 1H)

Example 14

1-((6-(2-(methylamino)-2-oxoethoxy)quinolin-4-yl)thio)cyclobutanecarboxylic acid

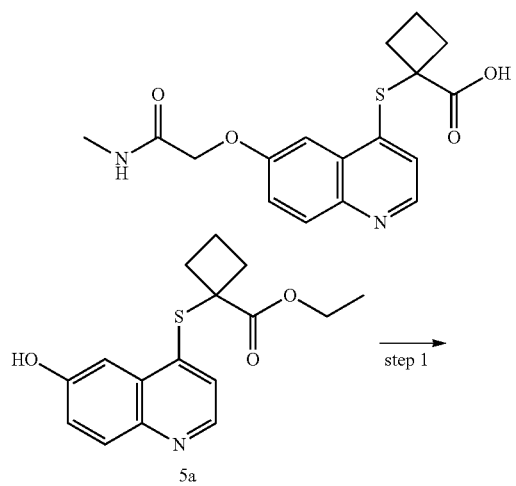

Step 1

Ethyl 1-((6-(2-(methylamino)-2-oxoethoxy)quinolin-4-yl)thio)cyclobutanecarboxylate Ethyl 1-((6-hydroxyquinolin-4-yl)thio)cyclobutanecarboxylate 5a (50 mg, 0.17 mmol), 2-chloro-N-methylacetamide (50 mg, 0.17 mmol) and potassium carbonate (35 mg, 0.25 mmol) were added to 4 mL of N,N-dimethylformamide, successively. Upon completion of the addition, the reaction solution was heated to 60° C. and stirred for 3 hours, followed by addition of 20 mL of water, and extraction with ethyl acetate (30 mL×3). The organic phases were combined, dried over anhydrous sodium sulfate, and filtered. The filtrate was concentrated under reduced pressure to obtain the title compound ethyl 1-((6-(2-(methylamino)-2-oxoethoxy)quinolin-4-yl)thio)cyclobutanecarboxylate 14a (40 mg, a brown oil), yield: 65%.

MS m/z (ESI): 373.3 [M−1]

Step 2

1-((6-(2-(methylamino)-2-oxoethoxy)quinolin-4-yl)thio)cyclobutanecarboxylic acid Ethyl 1-((6-(2-(methylamino)-2-oxoethoxy)quinolin-4-yl)thio)cyclobutanecarboxylate 14a (40 mg, 0.11 mmol) was dissolved in 5 mL a mixture of tetrahydrofuran and water (V:V=4:1), followed by addition of sodium hydroxide (11 mg, 0.27 mmol). The reaction solution was stirred for 2 hours, and evaporated under reduced pressure to remove tetrahydrofuran, followed by addition of 10 mL of water, dropwise addition of 2 M hydrochloric acid to adjust the pH to 5~6, and extraction with ethyl acetate (20 mL×3). The organic phases were combined, washed with saturated sodium chloride solution, dried over anhydrous sodium sulfate, and filtered. The filtrate was concentrated under reduced pressure, and the residue was purified by thin layer chromatography with elution system A to obtain the title compound 1-((6-(2-(methylamino)-2-oxoethoxy)quinolin-4-yl)thio)cyclobutanecarboxylic acid 14 (5 mg, a brown solid), yield: 14%.

MS m/z (ESI): 347.1 [M+1]

$^1$H NMR (400 MHz, DMSO) δ 8.76 (d, 1H), 8.10 (d, 1H), 7.67 (d, 1H), 7.45 (d, 1H), 7.30 (d, 1H), 4.71 (s, 1H), 4.42 (s, 1H), 2.96-3.06 (m, 2H), 2.73 (s, 3H), 2.34-2.44 (m, 2H), 2.24-2.32 (m, 1H), 2.02-2.22 (m, 1H)

Example 15

1-((6-(2-hydroxyethoxy)quinolin-4-yl)thio)cyclobutanecarboxylic acid

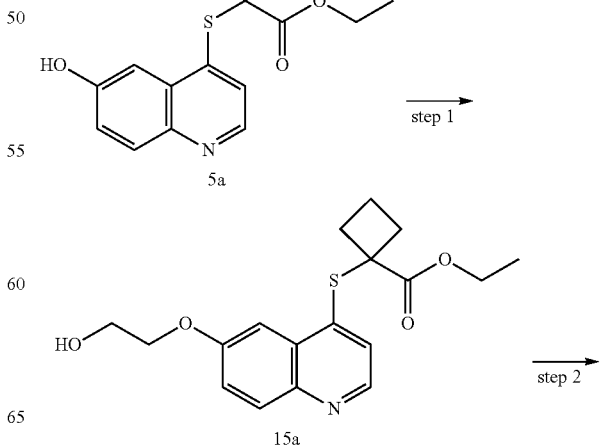

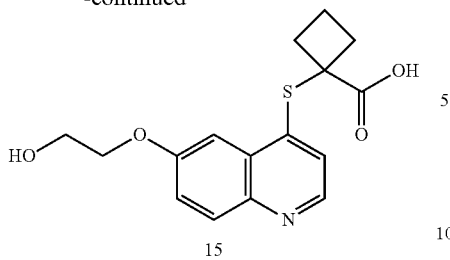

Step 1

Ethyl 1-((6-(2-hydroxyethoxy)quinolin-4-yl)thio)cyclobutanecarboxylate

Ethyl 1-((6-hydroxyquinolin-4-yl)thio)cyclobutanecarboxylate 5a (50 mg, 0.17 mmol), 2-bromoethanol (25 mg, 0.20 mmol) and potassium carbonate (35 mg, 0.25 mmol) were added to 5 mL of N,N-dimethylformamide, successively. The reaction solution was heated to 60° C. and stirred for 3 hours, followed by addition of 20 mL of water, and extraction with ethyl acetate (30 mL×3). The organic phases were combined, dried over anhydrous sodium sulfate, and filtered. The filtrate was concentrated under reduced pressure to obtain the title compound ethyl 1-((6-(2-hydroxyethoxy)quinolin-4-yl)thio)cyclobutanecarboxylate 15a (50 mg, a brown oil), yield: 88%.

MS m/z (ESI): 348.2 [M+1]

Step 2

1-((6-(2-hydroxyethoxy)quinolin-4-yl)thio)cyclobutanecarboxylic acid

Ethyl 1-((6-(2-hydroxyethoxy)quinolin-4-yl)thio)cyclobutanecarboxylate 15a (50 mg, 0.14 mmol) was dissolved in 5 mL of a mixture of tetrahydrofuran and water (V:V=4:1), followed by addition of sodium hydroxide (15 mg, 0.36 mmol). The reaction was stirred for 2 hours, then evaporated under reduced pressure to remove tetrahydrofuran, and mixed with 10 mL of water, followed by dropwise addition of 2 M hydrochloric acid to adjust the pH to 5~6, and extraction with n-butanol (20 mL×3). The organic phases were combined, washed with saturated sodium chloride solution, dried over anhydrous sodium sulfate, and filtered. The filtrate was concentrated under reduced pressure, and the residue was purified by silica gel column chromatography with elution system A to obtain the title compound 1-((6-(2-hydroxyethoxy)quinolin-4-yl)thio)cyclobutanecarboxylic acid 15 (5 mg, a white solid), yield: 11%.

MS m/z (ESI): 320.2 [M+1]

$^1$H NMR (400 MHz, CD3OD) δ 8.58 (d, 1H), 7.98 (d, 1H), 7.66 (d, 1H), 7.56 (d, 1H), 7.45 (d, 1H), 4.26 (t, 2H), 3.99 (t, 2H), 3.02-3.10 (m, 2H), 2.48-2.54 (m, 2H), 2.32-2.38 (m, 1H), 2.16-2.26 (m, 1H)

Example 16

1-((6-acetamidoquinolin-4-thio)cyclobutanecarboxylic acid

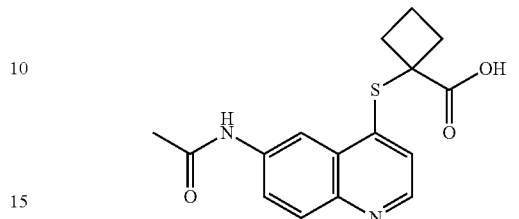

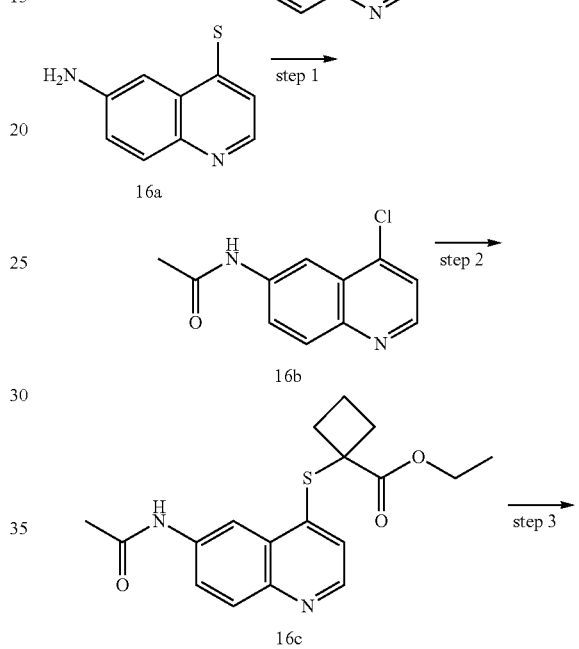

Step 1

N-(4-chloroquinolin-6-yl)acetamide 4-chloroquinolin-6-amine 16a (80 mg, 0.45 mmol, prepared by a well known method disclosed in "*Chinese Chemical Letters*, 2011, 22(3), 253-255"), acetyl chloride (35 mg, 0.45 mmol) and triethylamine (91 mg, 0.90 mmol) were added to 2 mL of N,N-dimethylformamide, successively. The reaction solution was stirred for 16 hours, and 10 mL of water were added to quench the reaction. The aqueous phase was separated, and extracted with dichloromethane (15 mL×3). The organic phases were combined, washed with saturated sodium chloride solution, and filtered. The filtrate was concentrated under reduced pressure, and the residue was purified by thin layer chromatography with elution system A to obtain the title compound N-(4-chloroquinolin-6-yl)acetamide 16b (80 mg, a yellow solid), which was used directly in the next step.

Step 2

Ethyl 1-((6-acetamidoquinolin-4-yl)thio)cyclobutanecarboxylate

Under argon atmosphere, N-(4-chloroquinolin-6-yl)acetamide 16b (112 mg, 0.51 mmol) and sodium sulfide (48 mg, 0.61 mmol) were dissolved in 2 mL of N,N-dimethylformamide. The reaction solution was heated to 80° C. and stirred for 2 hours. Ethyl 1-bromocyclobutanecarboxylate (126 mg, 0.61 mmol) and cesium carbonate (497 mg, 1.53 mmol) were added to the reaction solution. Upon completion of the addition, the reaction solution was heated to 60° C. and stirred for 2 hours. The reaction solution was filtered, and the filter cake was washed with dichloromethane (10 mL×2). The filtrate was concentrated under reduced pressure, and the residue was purified by thin layer chromatography with elution system C to obtain the title compound ethyl 1-((6-acetamidoquinolin-4-yl)thio)cyclobutanecarboxylate 16c (45 mg, a yellow solid), yield: 26%.

MS m/z (ESI): 345.3 [M+1]

Step 3

1-((6-acetamidoquinolin-4-yl)thio)cyclobutanecarboxylic acid

Ethyl 1-((6-acetamidoquinolin-4-yl)thio)cyclobutanecarboxylate 16c (45 mg, 0.13 mmol) was dissolved in 6 mL of a mixture of tetrahydrofuran, ethanol and water (V:V:V=4:1:1), followed by addition of lithium hydroxide monohydrate (11 mg, 0.26 mmol). The reaction solution was stirred for 2 hours, added dropwise with 1 M hydrochloric acid to adjust the pH to 5~6, mixed with 10 mL of dichloromethane, and the organic phase was separated. The aqueous phase was extracted with dichloromethane (10 mL×2). The organic phases were combined, washed with saturated sodium chloride solution, dried over anhydrous sodium sulfate, and filtered. The filtrate was concentrated under reduced pressure to obtain the title compound 1-((6-acetamidoquinolin-4-yl)thio)cyclobutanecarboxylic acid 16 (8 mg, a white solid), yield: 20° A.

MS m/z (ESI): 315.2 [M−1]

$^1$H NMR (400 MHz, DMSO) δ 13.15 (s, 1H), 10.08 (s, 1H), 8.55-8.61 (m, 2H), 7.62-7.70 (m, 2H), 7.48-7.55 (m, 1H), 2.78-2.89 (m, 2H), 2.27 (s, 3H), 2.02-2.18 (m, 3H), 1.82-1.93 (m, 1H)

Example 17

1-((6-cyanoquinolin-4-yl)thio)cyclobutanecarboxylic acid

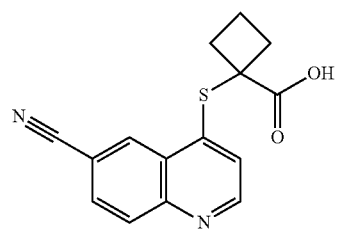

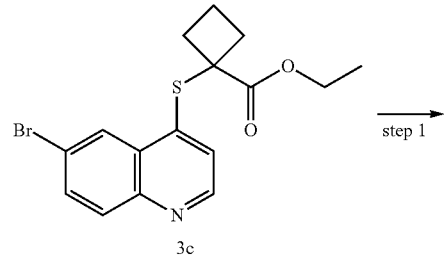

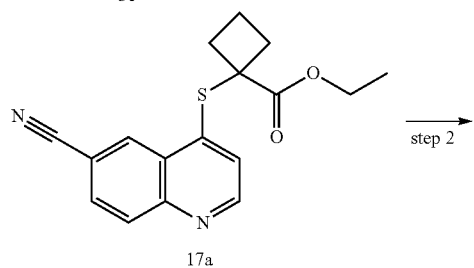

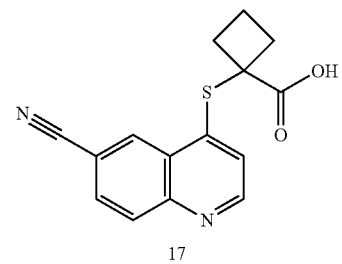

Step 1

Ethyl 1-((6-cyanoquinolin-4-yl)thio)cyclobutanecarboxylate

Ethyl 1-((6-bromoquinolin-4-yl)thio)cyclobutanecarboxylate 3c (100 mg, 0.27 mmol) was dissolved in 5 mL of N,N-dimethylformamide, followed by addition of cuprous cyanide (24 mg, 0.27 mmol). Upon completion of the addition, the reaction solution was heated to 130° C. and stirred for 27 hours. The reaction solution was filtered, and the filter cake was washed with dichloromethane (10 mL×2). The filtrate was concentrated under reduced pressure, and the residue was purified by thin layer chromatography with elution system C to obtain the title compound ethyl 1-((6-cyanoquinolin-4-yl)thio)cyclobutanecarboxylate 17a (80 mg, a yellow oil), yield: 94%.

MS m/z (ESI): 313.2 [M+1]

Step 2

1-((6-cyanoquinolin-4-yl)thio)cyclobutanecarboxylic acid

Ethyl 1-((6-cyanoquinolin-4-yl)thio)cyclobutanecarboxylate 17a (25 mg, 0.08 mmol) and lithium hydroxide monohydrate (3 mg, 0.16 mmol) were dissolved in 4 mL of a mixture of tetrahydrofuran and water (V:V=4:1). The reaction solution was stirred for 16 hours, and added dropwise with 1 M hydrochloric acid to adjust the pH to 5~6, followed by addition of 10 mL of dichloromethane, and separation of the organic phase. The aqueous phase was extracted with dichloromethane (10 mL×2). The organic phases were combined, washed with saturated sodium chloride solution, dried over anhydrous sodium sulfate and filtered. The filtrate was concentrated under reduced pressure, and the residue was purified by thin layer chromatography with elution system A to obtain the title compound 1-((6-cyanoquinolin-4-yl)thio) cyclobutanecarboxylic acid 17 (10 mg, a white solid), yield: 44%.

MS m/z (ESI): 283.2 [M−1]

$^1$H NMR (400 MHz, DMSO) δ 13.10 (s, 1H), 8.68-8.78 (m, 1H), 8.48-8.57 (m, 1H), 7.98-8.15 (m, 2H), 7.64-7.72 (m, 1H), 2.80-2.95 (m, 2H), 2.05-2.24 (m, 3H), 1.84-1.96 (m, 1H)

Example 18

1-((6-(3-cyanophenyl)quinolin-4-yl)thio)cyclobutanecarboxylic acid

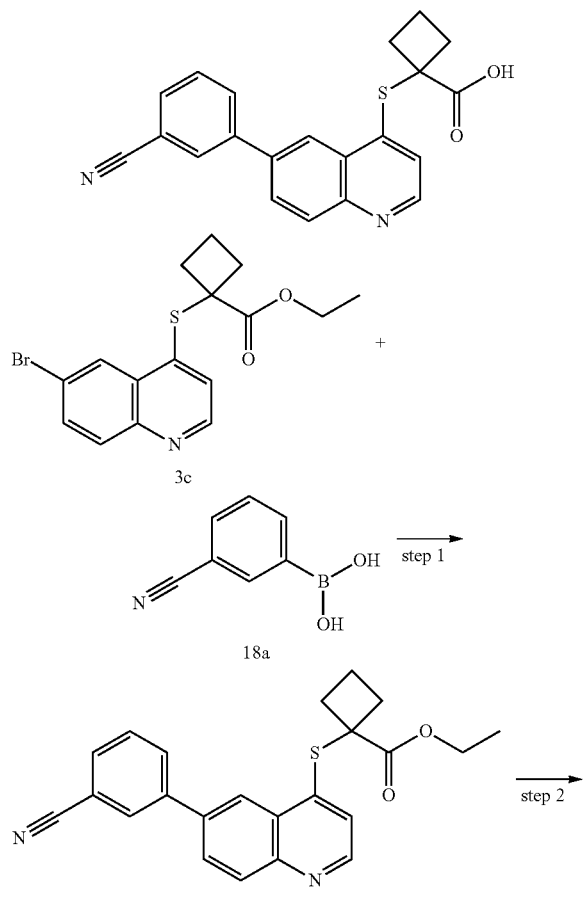

Step 1

Ethyl 1-((6-(3-cyanophenyl)quinolin-4-yl)thio)cyclobutanecarboxylate

Under argon atmosphere, ethyl 1-((6-bromoquinolin-4-yl) thio)cyclobutanecarboxylate 3c (100 mg, 0.27 mmol), (3-cyanophenyl)boronic acid 18a (48 mg, 0.33 mmol), [1,1'-Bis(diphenylphosphino)ferrocene]dichloropalladium (20 mg, 0.03 mmol) and sodium carbonate (43 mg, 0.41 mmol) were added to 5 mL of a mixture of 1,4-dioxane and water (V:V=4:1), successively. Upon completion of the addition, the reaction solution was heated to 90° C., and stirred for 2 hours. The reaction solution was filtered, and the filtrate was mixed with 10 mL of water, stirred uniformly, and extracted with dichloromethane (15 mL×3). The organic phases were combined, washed with saturated sodium chloride solution, dried over anhydrous sodium sulfate, and filtered. The filtrate was concentrated under reduced pressure to obtain the title compound ethyl 1-((6-(3-cyanophenyl)quinolin-4-yl)thio)cyclobutanecarboxylate 18b (90 mg, a brown liquid), yield: 85%.

MS m/z (ESI): 389.0 [M+1]

Step 2

1-((6-(3-cyanophenyl)quinolin-4-yl)thio)cyclobutanecarboxylic acid

Ethyl 1-((6-(3-cyanophenyl)quinolin-4-yl)thio)cyclobutanecarboxylate 18b (90 mg, 0.23 mmol) and lithium hydroxide monohydrate (19 mg, 0.46 mmol) were dissolved in 6 mL of a mixture of tetrahydrofuran, methanol and water (V:V:V=4:1:1). The reaction solution was stirred for 16 hours, added dropwise with 1 M hydrochloric acid to adjust the pH to 5-6, and mixed with 10 mL of dichloromethane. The organic phase was separated, and the aqueous phase was extracted with dichloromethane (10 mL×2). The organic phases were combined, washed with saturated sodium chloride solution, dried over anhydrous sodium sulfate, and filtered. The filtrate was concentrated under reduced pressure, and the residue was purified by thin layer chromatography with elution system C to obtain the title compound 1-((6-(3-cyanophenyl)quinolin-4-yl)thio)cyclobutanecarboxylic acid 18 (10 mg, a yellow solid), yield: 12%.

MS m/z (ESI): 361.1 [M+1]

$^1$H NMR (400 MHz, DMSO) δ 13.30 (s, 1H), 8.59-8.64 (m, 1H), 8.27-8.34 (m, 2H), 8.10-8.19 (m, 2H), 8.03-8.09 (m, 1H), 7.89-7.93 (m, 1H), 7.74-7.78 (m, 1H), 7.54-7.59 (m, 1H), 2.81-2.95 (m, 2H), 2.16-2.27 (m, 2H), 2.06-2.15 (m, 1H), 1.87-1.98 (m, 1H)

Example 19

1-((6-(4-(trifluoromethyl)phenyl)quinolin-4-yl)thio) cyclobutanecarboxylic acid

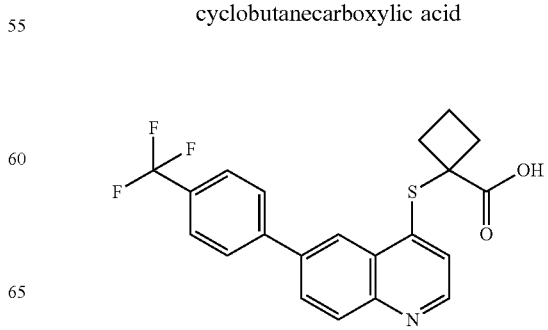

65

-continued

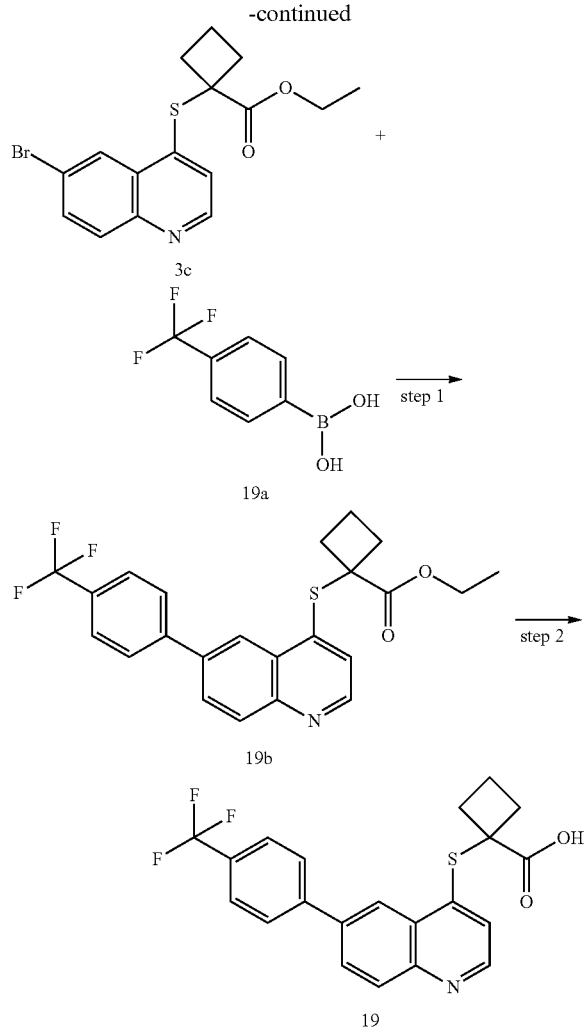

Step 1

Ethyl 1-((6-(4-(trifluoromethyl)phenyl)quinolin-4-yl)thio)cyclobutanecarboxylate Under argon atmosphere, ethyl 1-((6-bromoquinolin-4-yl)thio)cyclobutanecarboxylate 3c (100 mg, 0.27 mmol), (4-(trifluoromethyl)phenyl)boronic acid 19a (62 mg 0.33 mmol), [1,1'-Bis(diphenylphosphino)ferrocene]dichloropalladium (20 mg, 0.03 mmol) and sodium carbonate (43 mg, 0.41 mmol) were added to 5 mil, of a mixture of 1,4-dioxane and water (V:V=4:1), successively. Upon completion of the addition, the reaction solution was heated to 90° C. and stirred for 2 hours. The reaction solution was filtered, and the filtrate was mixed with 10 mL of water, stirred uniformly, and extracted with dichloromethane (15 mL×3). The organic phases were combined, washed with saturated sodium chloride solution, dried over anhydrous sodium sulfate, and filtered. The filtrate was concentrated under reduced pressure to obtain the title product ethyl 1-((6-(4-(trifluoromethyl)phenyl)quinolin-4-yl)thio)cyclobutanecarboxylate 19b (90 mg, a brown liquid), which was used directly in the next step.

MS m/z (ESI): 432.0 [M+1]

66

Step 2

1-((6-(4-(trifluoromethyl)phenyl)quinolin-4-yl)thio)cyclobutanecarboxylic acid

Ethyl 1-((6-(4-(trifluoromethyl)phenyl)quinolin-4-yl)thio)cyclobutanecarboxylate 19b (90 mg, 0.21 mmol) and sodium hydroxide (17 mg, 0.42 mmol) were dissolved in 6 mL of a mixture of tetrahydrofuran, methanol and water (V:V:V=4:1:1). The reaction was stirred for 16 hours, added dropwise with 1 M hydrochloric acid to adjust the pH to 5~6, and mixed with 10 mL of dichloromethane. The organic phase was separated, and the aqueous phase was extracted with dichloromethane (10 mL×2). The organic phases were combined, washed with saturated sodium chloride solution, dried over anhydrous sodium sulfate, and filtered. The filtrate was concentrated under reduced pressure, and the residue was purified by thin layer chromatography with elution system A to obtain the title compound 1-((6-(4-(trifluoromethyl)phenyl)quinolin-4-yl)thio)cyclobutanecarboxylic acid 19 (10 mg, a yellow solid), yield: 12%.

MS m/z (ESI): 404.3 [M+1]

$^1$H NMR (400 MHz, DMSO) δ 13.20 (s, 1H), 8.74-8.82 (m, 1H), 8.32-8.38 (m, 1H), 8.12-8.23 (m, 2H), 8.01-8.07 (m, 2H), 7.88-7.94 (m, 2H), 7.21-7.28 (m, 1H), 2.87-2.98 (m, 2H), 2.35-2.45 (m, 2H), 2.21-2.30 (m, 1H), 1.98-2.10 (m, 1H)

Example 20

1-((6-(4-cyanophenyl)quinolin-4-yl)thio)cyclobutanecarboxylic acid

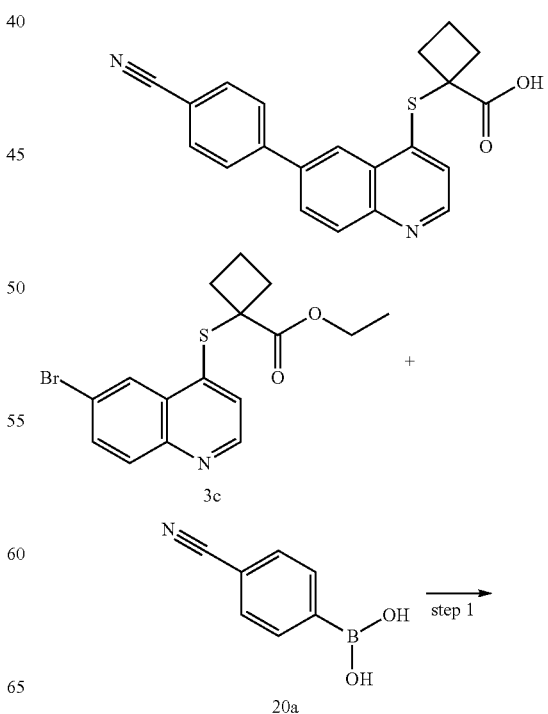

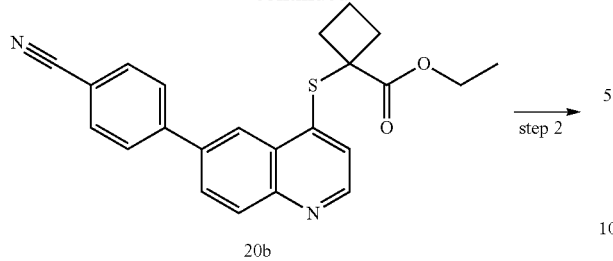

20b

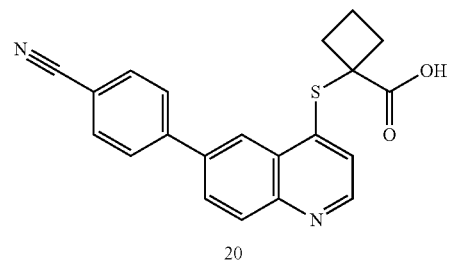

20

Step 1

Ethyl 1-((6-(4-cyanophenyl)quinolin-4-yl)thio)cyclobutanecarboxylate

Under argon atmosphere, ethyl 1-((6-bromoquinolin-4-yl)thio)cyclobutanecarboxylate 3c (100 mg, 0.27 mmol), (4-cyanophenyl)boronic acid 20a (48 mg, 0.33 mmol), [1,1'-Bis(diphenylphosphino)ferrocene]dichloropalladium (20 mg, 0.03 mmol) and sodium carbonate (43 mg, 0.41 mmol) were added to 5 mL of a mixture of 1,4-dioxane and water (V:V=4:1), successively. Upon completion of the addition, the reaction solution was heated to 90° C. and stirred for 2 hours. The reaction solution was filtered, and the filtrate was mixed with 10 mL of water, stirred uniformly, and extracted with dichloromethane (15 mL×3). The organic phases were combined, washed with saturated sodium chloride solution, dried over anhydrous sodium sulfate, and filtered. The filtrate was concentrated under reduced pressure to obtain the title compound ethyl 1-((6-(4-cyanophenyl)quinolin-4-yl)thio)cyclobutanecarboxylate 20b (90 mg, a brown liquid), yield: 85%.

MS m/z (ESI): 389.3 [M+1]

Step 2

1-((6-(4-cyanophenyl)quinolin-4-yl)thio)cyclobutanecarboxylic acid

Ethyl 1-((6-(4-cyanophenyl)quinolin-4-yl)thio)cyclobutanecarboxylate 206 (90 mg, 0.23 mmol) and lithium hydroxide monohydrate (19 mg, 0.46 mmol) were dissolved in 6 mL of a mixture of tetrahydrofuran, methanol and water (V:V:V=4:1:1). The reaction solution was stirred for 16 hours, added dropwise with 1 M hydrochloric acid to adjust the pH to 5~6, and mixed with 10 mL of dichloromethane. The organic phase was separated, and the aqueous phase was extracted with dichloromethane (10 mL×2). The organic phases were combined, washed with saturated sodium chloride solution, dried over anhydrous sodium sulfate, and filtered. The filtrate was concentrated under reduced pressure, and the residue was purified by thin layer chromatography with elution system C to obtain the title compound 1-((6-(4-cyanophenyl)quinolin-4-yl)thio)cyclobutanecarboxylic acid 20 (10 mg, a yellow solid), yield: 12%.

MS m/z (ESI): 361.2 [M+1]

$^1$H NMR (400 MHz, DMSO) δ 13.30 (s, 1H), 8.81-8.90 (m, 1H), 8.36-8.41 (m, 1H), 8.24-8.30 (m, 1H), 8.14-8.19 (m, 1H), 7.97-8.12 (m, 4H), 7.27-7.35 (m, 1H), 2.90-3.04 (m, 2H), 2.36-2.47 (m, 2H), 2.21-2.34 (m, 1H), 2.0-2.13 (m, 1H)

Example 21

1-((6-(2-fluorophenyl)quinolin-4-yl)thio)cyclobutanecarboxylic acid

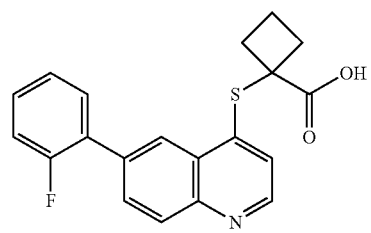

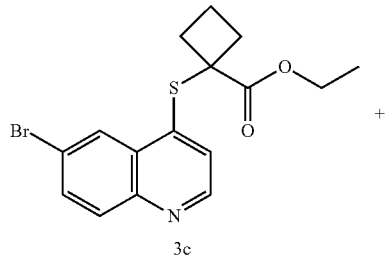

3c

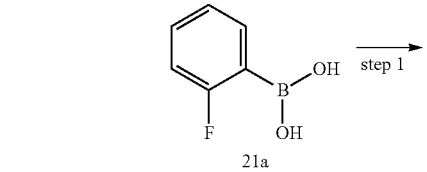

21a

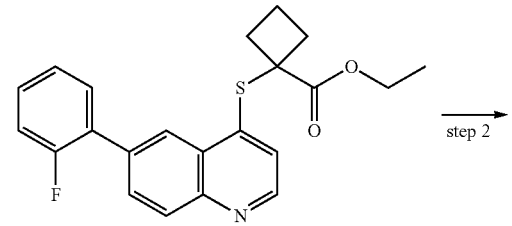

21b

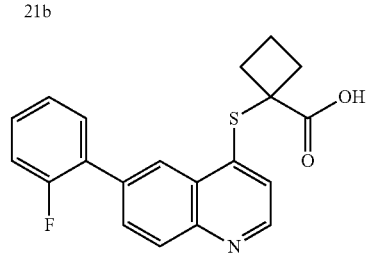

21

Step 1

Ethyl 1-((6-(2-fluorophenyl)quinolin-4-yl)thio)cyclobutanecarboxylate

Under argon atmosphere, ethyl 1-((6-bromoquinolin-4-yl)thio)cyclobutanecarboxylate 3c (100 mg, 0.27 mmol), (2-fluorophenyl)boronic acid 21a (46 mg, 0.33 mmol), [1,1'-Bis(diphenylphosphino)ferrocene]dichloropalladium (20 mg, 0.03 mmol) and sodium carbonate (43 mg, 0.41 mmol) were added to 2.5 mL of a mixture of 1,4-dioxane and water (V:V=4:1), successively. Upon completion of the addition, the reaction solution was heated to 90° C. and stirred for 2 hours. The reaction solution was filtered, and the filtrate was mixed with 10 mL of water, stirred uniformly, and extracted with dichloromethane (15 mL×3). The organic phases were combined, washed with saturated sodium chloride solution, dried over anhydrous sodium sulfate, and filtered. The filtrate was concentrated under reduced pressure to obtain the title compound ethyl 1-((6-(2-fluorophenyl)quinolin-4-yl)thio)cyclobutanecarboxylate 21b (80 mg, a brown liquid), yield: 77%.

MS m/z (ESI): 382.3 [M+1]

Step 2

1-((6-(2-fluorophenyl)quinolin-4-yl)thio)cyclobutanecarboxylic acid

Ethyl 1-((6-(2-fluorophenyl)quinolin-4-yl)thio)cyclobutanecarboxylate 21b (80 mg, 0.21 mmol) and sodium hydroxide (17 mg, 0.42 mmol) were dissolved in 6 mL of a mixture of tetrahydrofuran, methanol and water (V:V:V=4:1:1). The reaction solution was stirred for 16 hours, added dropwise with 1 M hydrochloric acid to adjust the pH to 5~6, and mixed with 10 mL of dichloromethane. The organic phase was separated, and the aqueous phase was extracted with dichloromethane (10 mL×2). The organic phases were combined, washed with saturated sodium chloride solution, dried over anhydrous sodium sulfate, and filtered. The filtrate was concentrated under reduced pressure, and the residue was purified by thin layer chromatography with elution system C to obtain the title compound 1-((6-(2-fluorophenyl)quinolin-4-yl)thio)cyclobutanecarboxylic acid 21 (10 mg, a yellow solid), yield: 14%.

MS m/z (ESI): 354.3 [M+1]
$^1$H NMR (400 MHz, DMSO) δ 13.30 (s, 1H), 8.78-8.86 (m, 1H), 8.24-8.29 (m, 1H), 8.13-8.20 (m, 1H), 8.01-8.10 (m, 1H), 7.66-7.76 (m, 1H), 7.48-7.59 (m, 1H), 7.35-7.46 (m, 2H), 7.25-7.33 (m, 1H), 2.88-3.02 (m, 2H), 2.33-2.45 (m, 2H), 2.18-2.30 (m, 1H), 1.96-2.10 (m, 1H)

Example 22

1-((6-(2-(trifluoromethyl)phenyl)quinolin-4-yl)thio)cyclobutanecarboxylic acid

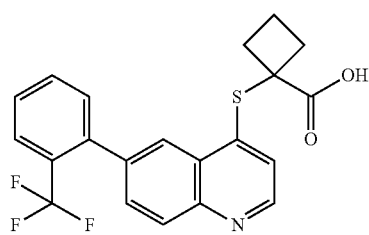

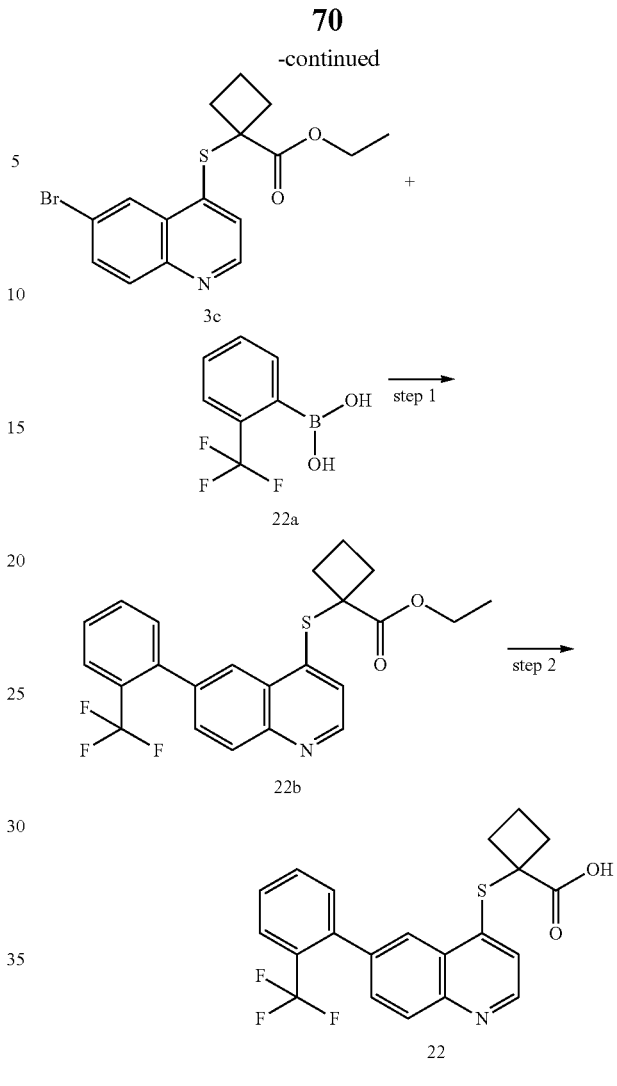

Step 1

Ethyl 1-((6-(2-(trifluoromethyl)phenyl)quinolin-4-yl)thio)cyclobutanecarboxylate Under argon atmosphere, ethyl 1-((6-bromoquinolin-4-yl)thio)cyclobutanecarboxylate 3c (100 mg, 0.27 mmol), (2-(trifluoromethyl)phenyl)boronic acid 22a (62 mg, 0.33 mmol), [1,1'-Bis(diphenylphosphino)ferrocene]dichloropalladium (20 mg, 0.03 mmol) and sodium carbonate (43 mg, 0.41 mmol) were added to 5 mL of a mixture of 1,4-dioxane and water (V:V=4:1), successively. Upon completion of the addition, the reaction solution was heated to 90° C. and stirred for 2 hours. The reaction solution was filtered, and the filtrate was mixed with 10 mL of water, stirred uniformly, and extracted with dichloromethane (15 mL×3). The organic phases were combined, washed with saturated sodium chloride solution, dried over anhydrous sodium sulfate, and filtered. The filtrate was concentrated under reduced pressure to obtain the title compound ethyl 1-((6-(2-(trifluoromethyl)phenyl)quinolin-4-yl)thio)cyclobutanecarboxylate 22b (90 mg, a black liquid), yield: 76%.

MS m/z (ESI): 432.3 [M+1]

Step 2

1-((6-(2-(trifluoromethyl)phenyl)quinolin-4-yl)thio)cyclobutanecarboxylic acid Ethyl 1-((6-(2-(trifluoromethyl)phenyl)quinolin-4-yl)thio)cyclobutanecarboxylate 22b (90 mg, 0.21 mmol) and lithium hydroxide monohydrate (18 mg, 0.42 mmol) were dissolved in 6 mL of a mixture of tetrahydrofuran, methanol and water (V:V:V=4:1:1). The reaction solution was stirred for 16 hours, added dropwise with 1 M hydrochloric acid to adjust the pH to 5~6, and mixed with 10 mL of dichloromethane. The organic phase was separated, and the aqueous phase was extracted with dichloromethane (10 mL×2). The organic phases were combined, washed with saturated sodium chloride solution, dried over anhydrous sodium sulfate, and filtered. The filtrate was concentrated under reduced pressure and the residue was purified by thin layer chromatography with elution system C to obtain the title compound 1-((6-(2-(trifluoromethyl)phenyl)quinolin-4-yl)thio)cyclobutanecarboxylic acid 22 (10 mg, a pale yellow solid), yield: 12%.

MS m/z (ESI): 404.3 [M+1]

$^1$H NMR (400 MHz, DMSO) δ 13.30 (s, 1H), 8.58-8.64 (m, 1H), 7.97-8.03 (m, 1H), 7.88-7.94 (m, 2H), 7.76-7.82 (m, 1H), 7.66-7.73 (m, 2H), 7.57-7.63 (m, 1H), 7.52-7.56 (m, 1H), 2.75-2.89 (m, 2H), 2.0-2.17 (m, 3H), 1.82-1.94 (m, 1H)

Example 23

1-((6-cyclopropylquinolin-4-yl)thio)cyclobutanecarboxylic acid

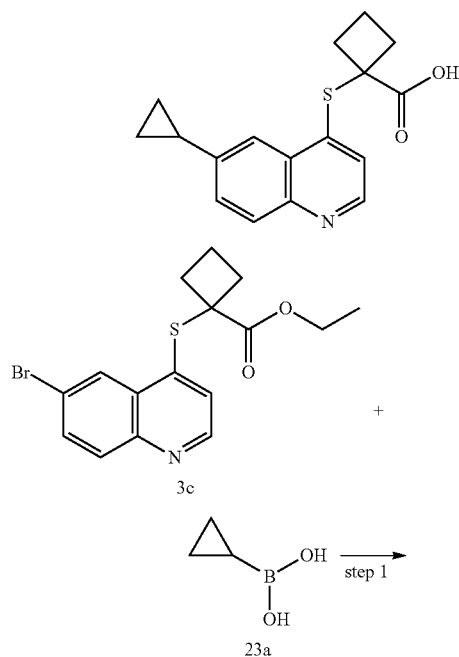

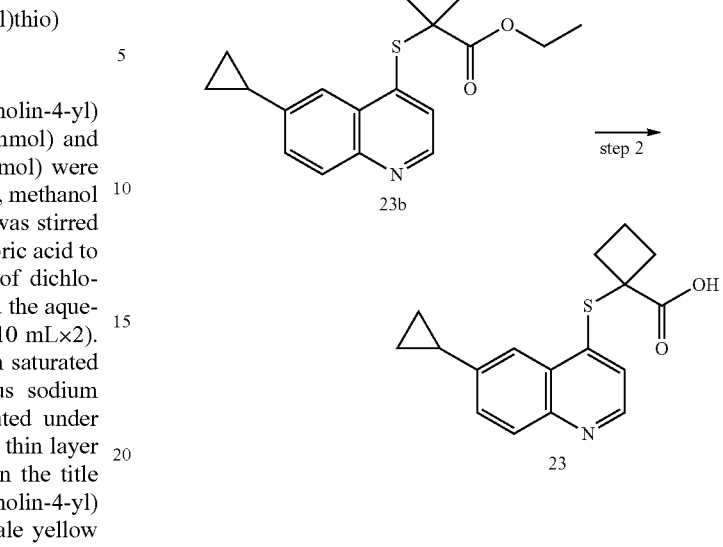

Step 1

Ethyl 1-((6-cyclopropylquinolin-4-yl)thio)cyclobutanecarboxylate

Under argon atmosphere, ethyl 1-((6-bromoquinolin-4-yl)thio)cyclobutanecarboxylate 3c (248 mg, 0.68 mmol), cyclopropylboronic acid 23a (174 mg, 2.0 mmol), [1,1'-Bis(diphenylphosphino)ferrocene]dichloropalladium (50 mg, 0.07 mmol) and sodium carbonate (108 mg, 1.02 mmol) were added to 5 mL of a mixture of 1,4-dioxane and water (V:V=4:1), successively. Upon completion of the addition, the reaction solution was heated to 90° C. and stirred for 17 hours. The reaction solution was filtered, and the filtrate was mixed with 10 mL of water, stirred uniformly, and extracted with dichloromethane (15 mL×3). The organic phases were combined, washed with saturated sodium chloride solution, dried over anhydrous sodium sulfate, and filtered. The filtrate was concentrated under reduced pressure to obtain the title compound ethyl 1-((6-cyclopropylquinolin-4-yl)thio)cyclobutanecarboxylate 23b (180 mg, a black oil), yield: 81%.

MS m/z (ESI): 328.3 [M+1]

Step 2

1-((6-cyclopropylquinolin-4-yl)thio)cyclobutanecarboxylic acid

Ethyl 1-((6-cyclopropylquinolin-4-yl)thio)cyclobutanecarboxylate 23b (180 mg, 0.55 mmol) and sodium hydroxide (44 mg, 1.10 mmol) were dissolved in 6 mL of a mixture of tetrahydrofuran, methanol and water (V:V:V=4:1:1). The reaction solution was stirred for 16 hours, added dropwise with 1 M hydrochloric acid to adjust the pH to 5~6, and mixed with 10 mL of dichloromethane. The organic phase was separated, and the aqueous phase was extracted with dichloromethane (10 mL×2). The organic phases were combined, washed with saturated sodium chloride solution, dried over anhydrous sodium sulfate, and filtered. The filtrate was concentrated under reduced pressure and the residue was purified by thin layer chromatography with elution system A to obtain the title compound 1-((6-cyclopropylquinolin-4-yl)thio)cyclobutanecarboxylic acid 23 (20 mg, a white solid), yield: 12%.

MS m/z (ESI): 300.3 [M+1]

¹H NMR (400 MHz, DMSO) δ 13.17 (s, 1H), 8.80-8.90 (m, 1H), 7.97-8.08 (m, 1H), 7.87-7.95 (m, 1H), 7.64-7.75 (m, 1H), 7.28-7.39 (m, 1H), 2.93-3.07 (m, 2H), 2.37-2.47 (m, 2H), 2.21-2.34 (m, 2H), 2.04-2.15 (m, 1H), 1.10-1.20 (m, 2H), 0.84-0.95 (m, 2H)

Example 24

1-((6-cyanomethoxy)quinolin-4-yl)thio)cyclobutanecarboxylic acid

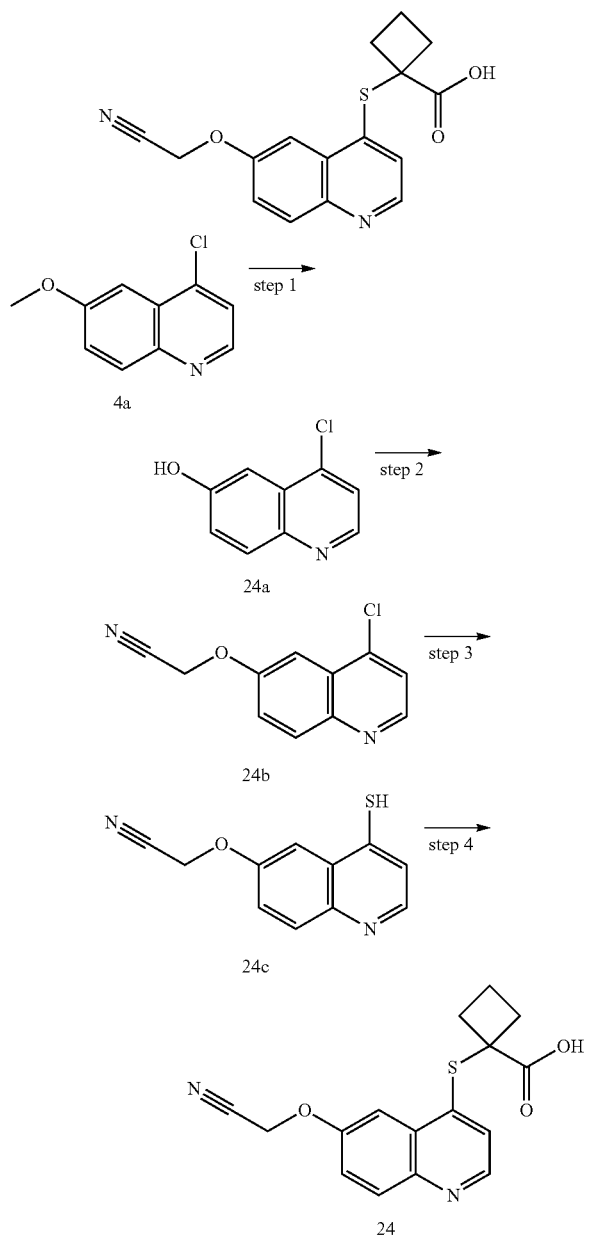

Step 1

4-chloroquinolin-6-ol 4-chloro-6-methoxyquinoline 4a (500 mg, 2.5 mmol) was dissolved in 10 mL of dichloromethane, and hydroiodic acid (45%, 5 mL) was added dropwise. Upon completion of the addition, the reaction solution was heated to 100° C. and stirred for 5 hours. 20 mL of water was added to the reaction solution, and the organic phase was separated. The aqueous phase was added dropwise with saturated sodium carbonate solution to adjusted the pH to 8~9, and extracted with dichloromethane (30 mL×3). The organic phases were combined, washed with saturated sodium chloride solution, dried over anhydrous sodium sulfate, and filtered. The filtrate was concentrated under reduced pressure to obtain the crude title compound 4-chloroquinolin-6-ol 24a (300 mg, a white solid), which was used directly in the next step.

MS m/z (ESI): 328.3 [M+1]

Step 2

2-((4-chloroquinolin-6-yl)oxy)acetonitrile 4-chloroquinolin-6-ol 24a (300 mg, 1.7 mmol) was dissolved in 10 mL of N,N-dimethylformamide, followed by addition of bromoacetonitrile (240 mg, 2.0 mmol) and potassium carbonate (350 mg, 2.5 mmol). Upon completion of the addition, the reaction solution was heated to 60° C. and stirred for 3 hours. The reaction solution was mixed with 50 mL of water, and extracted with ethyl acetate (50 mL×3). The organic phases were combined, washed with saturated sodium chloride solution, dried over anhydrous sodium sulfate, and filtered. The filtrate was concentrated under reduced pressure to obtain the title compound 2-((4-chloroquinolin-6-yl)oxy)acetonitrile 24b (300 mg, a off-white solid), yield: 81%

MS m/z (ESI): 219.1 [M+1]

Step 3

2-((4-mercaptoquinolin-6-yl)oxy)acetonitrile 2-((4-chloroquinolin-6-yl)oxy)acetonitrile 24b (250 mg, 1.15 mmol) was dissolved in 3 mL of N,N-dimethylformamide, followed by addition of sodium sulfide (90 mg, 1.15 mmol). Upon completion of the addition, the reaction solution was heated to 110° C. and stirred for 3 hours. The reaction solution was concentrated under reduced pressure, mixed with 10 mL of water, added dropwise with 1 M hydrochloric to adjust the pH to 5~6, and extracted with ethyl acetate (30 mL×3). The organic phases were combined, washed with saturated sodium chloride solution, dried over anhydrous sodium sulfate, and filtered. The filtrate was concentrated under reduced pressure to obtain the title compound 2-((4-mercaptoquinolin-6-yl)oxy)acetonitrile 24c (248 mg, a brown oil), which was used directly in the next step.

MS m/z (ESI): 217.0 [M+1]

Step 4

1-((6-(cyanomethoxy)quinolin-4-yl)thio)cyclobutanecarboxylic acid 2-((4-mercaptoquinolin-6-yl)oxy)acetonitrile 24c (248 mg, 1.15 mmol) was dissolved in 3 mL of N,N-dimethylformamide, followed by addition of 1-bromocyclobutanecarboxylic acid (249 mg, 1.38 mmol) and triethylamine (292 mg, 2.89 mmol). Upon completion of the addition, the reaction solution was heated to 60° C. and stirred for 3 hours. The reaction solution was mixed with 10 mL of water, and washed with ethyl acetate (20 mL×2). The aqueous phase was added dropwise with 2 M hydrochloric acid to adjust the pH to 3~4, and extracted with n-butanol (50 mL×3). The organic phases were combined, washed with saturated sodium chloride solution, dried over anhydrous sodium sulfate, and filtered. The filtrate was concentrated under reduced pressure, and the residue was purified by thin layer chromatography with elution system A to obtain the crude compound. The crude compound was separated by HPLC to obtain the title compound 1-((6-(cyanomethoxy)quinolin-4-yl)thio)cyclobutanecarboxylic acid 24 (10 mg, an off-white solid), the yield of two steps: 3%.

MS m/z (ESI): 313.1 [M−1]

$^1$H NMR (400 MHz, CD3OD) δ 8.49 (d, 1H), 7.95 (d, 1H), 7.65 (d, 1H), 7.51 (dd, 1H), 7.44 (d, 1H), 5.20 (s, 2H), 2.97-3.02 (m, 2H), 2.27-2.41 (m, 3H), 2.05-2.08 (m, 1H)

Example 25

1-((6-(cyclopropanecarboxamido)quinolin-4-yl)thio)cyclobutanecarboxylic acid

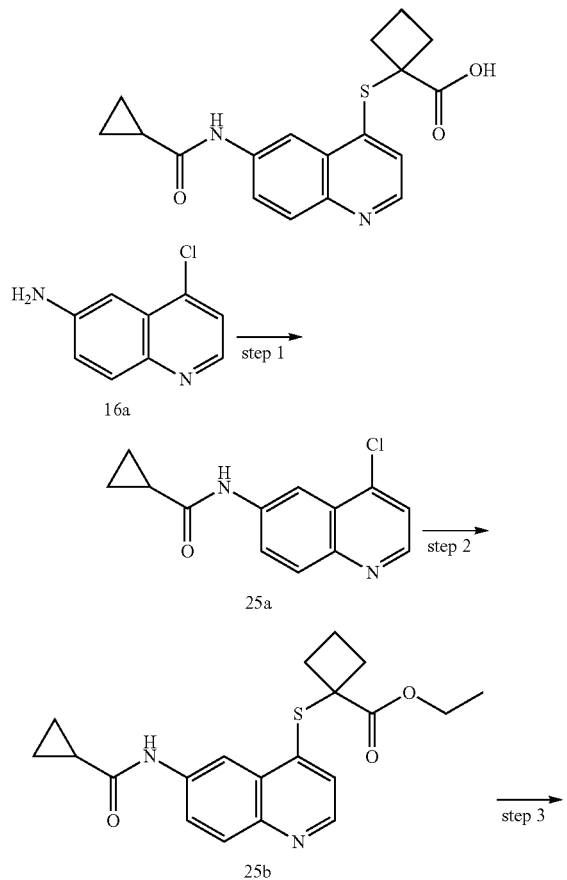

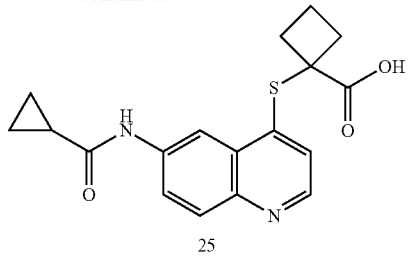

Step 1

N-(4-chloroquinolin-6-yl)cyclopropanecarboxamide 4-chloroquinolin-6-amine 16a (500 mg, 2.8 mmol), cyclopropanecarboxylic acid chloride (293 mg, 2.8 mmol) and triethylamine (566 mg, 5.6 mmol) were added to 5 mL of N,N-dimethylformamide, successively. The reaction was stirred for 16 hours, then 10 mL of water was added to quench the reaction. The aqueous phase was separated and extracted with dichloromethane (15 mL×3). The organic phases were combined, washed with saturated sodium chloride solution, and filtered. The filtrate was concentrated under reduced pressure, and the residue was purified by thin layer chromatography with elution system A to obtain the title compound N-(4-chloroquinolin-6-yl)cyclopropanecarboxamide 25a (350 mg, a yellow solid), yield: 51%.

MS m/z (ESI): 247.2 [M+1]

Step 2

Ethyl 1-((6-(cyclopropanecarboxamido)quinolin-4-yl)thio)cyclobutanecarboxylate

Under argon atmosphere, N-(4-chloroquinolin-6-yl)cyclopropanecarboxamide 25a (350 mg, 1.4 mmol) and sodium sulfide (133 mg, 1.7 mmol) were dissolved in 5 mL of N,N-dimethylformamide. The reaction solution was heated to 80° C. and stirred for 2 hours, followed by addition of ethyl 1-bromocyclobutanecarboxylate (352 mg, 1.7 mmol) and cesium carbonate (1.38 g, 4.3 mmol). Upon completion of the addition, the reaction solution was heated to 60° C. and stirred for 3 hours. The reaction solution was filtered, and the filter cake was washed with dichloromethane (10 mL×2). The filtrate was concentrated under reduced pressure, and the residue was purified by thin layer chromatography with elution system A to obtain the title compound ethyl 1-((6-(cyclopropanecarboxamido)quinolin-4-yl)thio)cyclobutanecarboxylate 25b (95 mg, a yellow solid), yield: 18%.

MS m/z (ESI): 371.1 [M+1]

Step 3

1-((6-(cyclopropanecarboxamido)quinolin-4-yl)thio)cyclobutanecarboxylic acid

Ethyl 1-((6-(cyclopropanecarboxamido)quinolin-4-yl)thio)cyclobutanecarboxylate 25b (95 mg. 0.26 mmol) was dissolved in 6 mL of a mixture of tetrahydrofuran, ethanol and water (V:V:V=4:1:1), followed by addition of lithium hydroxide monohydrate (22 mg, 0.51 mmol). The reaction solution was stirred for 16 hours, added dropwise with 1 M hydrochloric acid to adjust the pH to 5~6, and mixed with 10 mL of dichloromethane. The organic phase was separated, and the aqueous phase was extracted with dichloromethane (10 mL×2). The organic phases were combined, washed with saturated sodium chloride solution, dried over anhydrous sodium sulfate, and filtered. The filtrate was concentrated under reduced pressure, and the residue was purified by thin layer chromatography with elution system A to obtain the title compound 1-((6-(cyclopropanecarboxamido)quinolin-4-yl)thio)cyclobutanecarboxylic acid 25 (10 mg, a white solid), yield: 11%.

MS m/z (ESI): 343.4 [M+1]

$^1$H NMR (400 MHz, DMSO) δ 13.15 (s, 1H), 10.37 (s, 1H), 8.60-8.65 (m, 1H), 8.52-8.59 (m, 1H), 7.66-7.71 (m, 1H), 7.58-7.61 (m, 1H), 7.48-7.58 (m, 1H), 2.81-2.94 (m, 2H), 2.05-2.30 (m, 4H), 1.86-2.0 (m, 1H), 0.78-0.92 (m, 4H)

Example 26

1-((6-aminoquinolin-4-yl)thio)cyclobutanecarboxylic acid

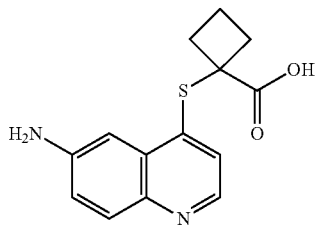

1-((6-(cyclopropanecarboxamido)quinolin-4-yl)thio)cyclobutanecarboxylic acid 25 (5 mg, 0.014 mmol) was dissolved in 5 mL of a mixture of 1,4-dioxane and water (V:V=4:1), followed by addition of 4 drops of 3 M concentrated hydrochloric acid. Upon completion of the addition, the reaction solution was heated to 90° C. and stirred for 16 hours. The reaction solution was concentrated under reduced pressure, and the residue was washed with diethyl ether (10 mL×2) to obtain the title compound 1-((6-aminoquinolin-4-yl)thio)cyclobutanecarboxylic acid 26 (15 mg, a khaki solid), yield: 3%.

MS m/z (ESI): 275.1 [M+1]

$^1$H NMR (400 MHz, DMSO) δ 13.17 (s, 1H), 8.62-8.67 (m, 1H), 7.43-7.50 (m, 1H), 7.33-7.39 (m, 1H), 7.13-7.24 (m, 2H), 3.20 (s, 2H), 2.87-3.0 (m, 2H), 2.31-2.43 (m, 2H), 2.17-2.28 (m, 1H), 1.96-2.10 (m, 1H)

Example 27

1-((6-(hydroxymethyl)quinolin-4-yl)thio)cyclobutanecarboxylic acid

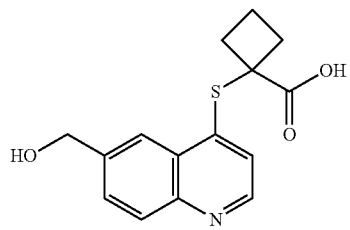

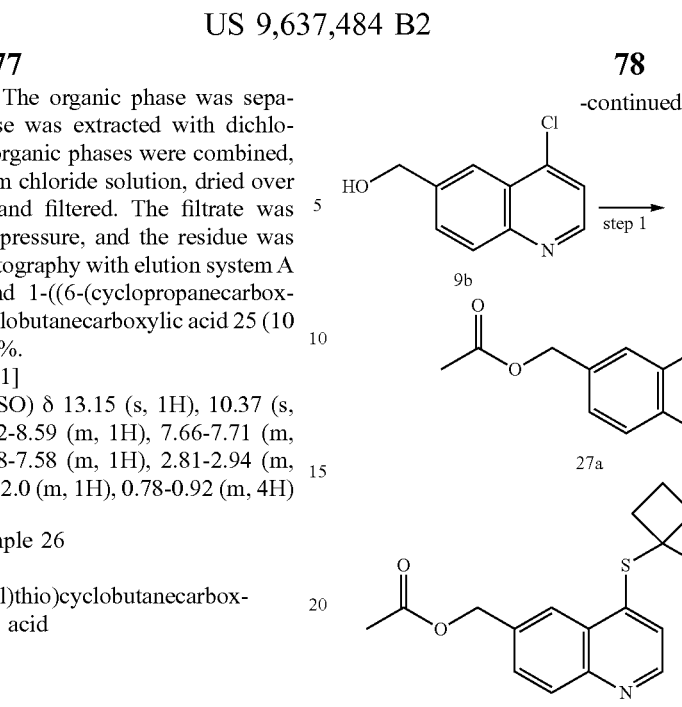

Step 1

(4-chloroquinolin-6-yl)methyl acetate

In an ice bath, (4-chloroquinolin-6-yl)methanol 9b (60 mg, 0.31 mmol) was dissolved in 4 mL of tetrahydrofuran, followed by addition of acetyl chloride (37 mg, 0.47 mmol). Upon completion of the addition, the ice bath was removed. The reaction solution was warmed up to room temperature naturally and stirred for 1 hour. The reaction solution was concentrated under reduced pressure, and the residue was dissolved in 50 mL of ethyl acetate, washed with saturated ammonium chloride solution (10 mL×2) and saturated sodium chloride solution (10 mL×2), successively, dried over anhydrous magnesium sulfate, and filtered. The filtrate was concentrated under reduced pressure to obtain the crude title compound (4-chloroquinolin-6-yl)methyl acetate 27a (73 mg, a white solid), which was used directly in the next step.

MS m/z (ESI): 236.1 [M+l]

Step 2

Ethyl 1-((6-(acetoxymethyl)quinolin-4-yl)thio)cyclobutanecarboxylate

Under argon atmosphere, (4-chloroquinolin-6-yl)methyl acetate 27a (73 mg, 0.31 mmol) and sodium sulfide (24 mg, 0.31 mmol) were added to 5 mL of N,N-dimethylformamide. Upon completion of the addition, the reaction solution was heated to 80° C. and stirred for 2 hours. After cooling down to room temperature, the reaction solution was mixed with ethyl 1-bromocyclobutanecarboxylate (77 mg, 0.37 mmol), then heated to 80° C. and stirred for a further 3 hours. The reaction solution was concentrated under reduced pressure to obtain the crude title compound ethyl 1-((6-(acetoxymethyl)quinolin-4-yl)thio)cyclobutanecarboxylate 27b (111 mg, a brown solid), which was used directly in the next step.

MS m/z (ESI): 360.2 [M+l]

Step 3

1-((6-(hydroxymethyl)quinolin-4-yl)thio)cyclobutanecarboxylic acid

Ethyl 1-((6-(acetoxymethyl)quinolin-4-yl)thio)cyclobutanecarboxylate 27b (111 mg, 0.31 mmol) was dissolved in 4 mL of a mixture of tetrahydrofuran and water (V:V=1:1), followed by addition of lithium hydroxide monohydrate (52 mg, 1.24 mmol). The reaction was stirred for 16 hours, and added dropwise with 1 M hydrochloric acid to adjust the pH to 5~6. The resulting solution was concentrated under reduced pressure, and the residue was purified by thin layer chromatography with elution system A to obtain the title compound 1-((6-(hydroxymethyl)quinolin-4-yl)thio)cyclobutanecarboxylic acid 27 (15 mg, a yellow solid), yield: 17%.

MS m/z (ESI): 290.2 [M+1]

¹H NMR (400 MHz, CD₃OD) δ 8.79 (s, 1H), 8.37-8.43 (m, 1H), 8.05-8.15 (m, 2H), 7.56-7.65 (d, 1H), 4.89 (s, 2H), 3.10-3.20 (m, 2H), 2.55-2.65 (m, 2H), 2.32-2.44 (m, 1H), 2.16-2.28 (m, 1H)

Example 28

1-((6-hydroxyquinolin-4-yl)thio)cyclobutanecarboxylic acid

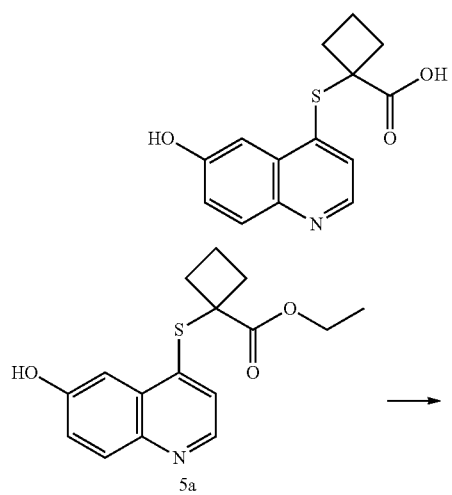

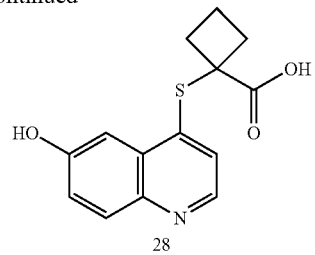

Ethyl 1-((6-hydroxyquinolin-4-yl)thio)cyclobutanecarboxylate 5a (50 mg, 0.17 mmol) was dissolved in 5 mL of a mixture of tetrahydrofuran and methanol (V:V=4:1), followed by addition of 1 mL of saturated sodium hydroxide solution. The reaction was stirred for 2 hours, then mixed with 20 mL of water, washed with ethyl acetate, added dropwise with 2 M hydrochloric acid to adjust the aqueous phase pH to 5~6, and extracted with n-butanol (15 mL×3). The organic phases were combined, concentrated under reduced pressure, and the residue was purified by thin layer chromatography with elution system A to obtain the title compound 1-((6-hydroxyquinolin-4-yl)thio)cyclobutanecarboxylic acid 28 (8 mg, a yellow solid), yield: 18%.

MS m/z (ESI): 274.1 [M−1]

¹H NMR (400 MHz, CD3OD) δ 8.54 (d, 1H), 7.98 (d, 1H), 7.58 (d, 1H), 7.53 (d, 1H), 7.44 (d, 1H), 3.04-3.13 (m, 2H), 2.48-2.56 (m, 2H), 2.32-2.39 (m, 1H), 2.14-2.22 (m, 1H)

Example 29

1-((6-(2-cyanoethyl)quinolin-4-yl)thio)cyclobutanecarboxylic acid

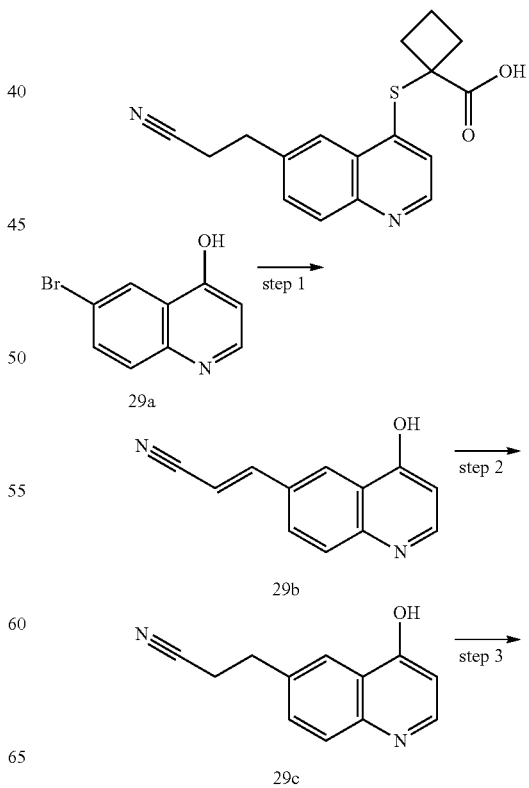

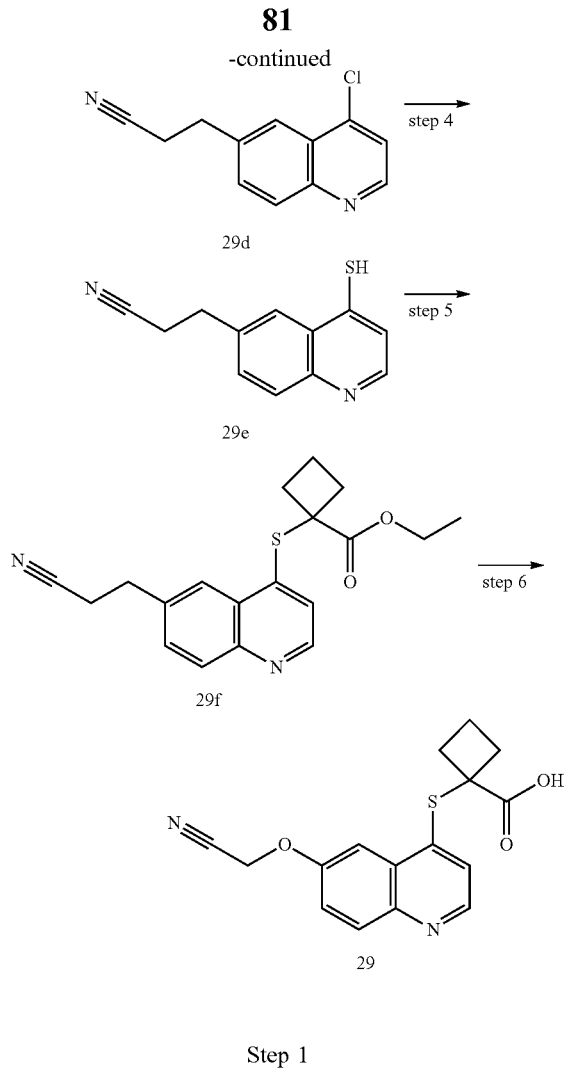

Step 1

(E)-3-(4-hydroxyquinolin-6-yl)acrylonitrile

Under argon atmosphere, 6-bromoquinolin-4-ol 29a (4.2 g, 18.9 mmol), acrylonitrile (1.5 g, 28.3 mmol), triethylamine (3.8 g, 37.7 mmol), triphenylphosphine (3.7 g, 14.2 mmol) and palladium acetate (420 mg, 1.89 mmol) were added to 10 mL of NA-dimethylformamide, successively. Upon completion of the addition, the reaction solution was heated to 140° C. and stirred for 3 hours, then mixed with 30 mL of water, and extracted with ethyl acetate (50 mL×3). The organic phases were combined, washed with saturated sodium chloride solution, dried over anhydrous sodium sulfate, and filtered. The filtrate was concentrated under reduced pressure, and the residue was purified by silica gel column chromatography with elution system A to obtain the title compound (E)-3-(4-hydroxyquinolin-6-yl)acrylonitrile 29b (1.5 g, a off-white solid), yield: 41%.

MS m/z (PSI): 195.0 [M−1]

Step 2

3-(4-hydroxyquinolin-6-yl)propanenitrile (E)-3-(4-hydroxyquinolin-6-yl)acrylonitrile 29b (50 mg, 0.26 mmol) was dissolved in 20 ml, of a mixture of dichloromethane and methanol (V:V=3:1), then triethylamine (10 mg, 0.10 mmol) and Pd/C (5 mg, 10%) were added, successively. Upon completion of the addition, the reaction solution was purged with hydrogen three times and stirred for 7 hours. The reaction solution was filtered through celite, and the filtrate was concentrated under reduced pressure to obtain the crude title compound 3-(4-hydroxyquinolin-6-yl) propanenitrile 29c (50 mg, a yellow oil), which was used directly in the next step.

MS m/z (ESI): 197.1 [M−1]

Step 3

3-(4-chloroquinolin-6-yl)propanenitrile 3-(4-hydroxyquinolin-6-yl)propanenitrile 29c (50 mg, 0.25 mmol) was added to 2 mL, of phosphorus oxychloride. The reaction solution was heated to 100° C. and stirred for 2 hours. After stopping heating, the reaction solution was cooled down to room temperature, and added to 20 mL ice water, followed by dropwise addition of saturated sodium bicarbonate solution to adjust the pH to 7~8, then extracted with dichloromethane (20 mL×3). The organic phases were combined, washed with saturated sodium chloride solution, dried over anhydrous sodium sulfate, and filtered. The filtrate was concentrated under reduced pressure to obtain the title compound 3-(4-chloroquinolin-6-yl)propanenitrile 29d (40 mg, a brown oil), yield: 73%.

MS m/z (ESI): 217.1 [M+1]

Step 4

3-(4-mercaptoquinolin-6-yl)propanenitrile 3-(4-chloroquinolin-6-yl)propanenitrile 29d (40 mg, 0.19 mmol) and sodium sulfide (22 mg, 0.28 mmol) was added to 3 mL of N,N-dimethylformamide. The reaction solution was heated to 100° C. and stirred for 3 hours, then mixed with 10 mL of water, followed by dropwise addition of 1 M hydrochloric acid to adjust the pH to 5~6, and extraction with ethyl acetate (30 mL×3). The organic phases were combined, washed with saturated sodium chloride solution, dried over anhydrous sodium sulfate, and filtered. The filtrate was concentrated under reduced pressure to obtain the title compound 3-(4-chloroquinolin-6-yl)propanenitrile 29e (40 mg, a yellow oil), which was used directly in the next step.

MS m/z (ESI): 215.1 [M+1]

Step 5

Ethyl 1-((6-(2-cyanoethyl)quinolin-4-yl)thio)cyclobutanecarboxylate 3-(4-chloroquinolin-6-yl)propanenitrile 29e (40 mg, 0.19 mmol), ethyl 1-bromocyclobutanecarboxylate (46 mg, 0.22 mmol) and potassium carbonate (39 mg, 0.28 mmol) were added to 4 mL of N,N-dimethylformamide, successively. The reaction solution was heated to 60° C., stirred for 2 hours, and concentrated under reduced pressure. The resulting solution was mixed with 20 mL of water, stirred uniformly, and extracted with ethyl acetate (30 mL×3). The organic phases were combined, washed with saturated sodium chloride solution, dried over anhydrous sodium sulfate, and filtered. The filtrate was concentrated under reduced pressure to obtain the title compound ethyl 1-((6-(2-cyanoethyl)quinolin-4-yl)thio)cyclobutanecarboxylate 29f (50 mg, a yellow oil), which was used directly in the next step.

MS m/z (ESI): 341.1 [M+1]

Step 6

1-((6-(2-cyanoethyl)quinolin-4-yl)thio)cyclobutanecarboxylic acid

Ethyl 1-((6-(2-cyanoethyl)quinolin-4-yl)thio)cyclobutanecarboxylate 29f (50 mg, 0.15 mmol) was dissolved in 5 mL of a mixture of tetrahydrofuran and water (V:V=4:1), followed by addition of sodium hydroxide (9 mg, 0.22 mmol). The reaction solution was stirred for 2 hours, then mixed with 10 mL of water, followed by dropwise addition of 2 M hydrochloric acid to adjust the pH to 5~6, and extraction with n-butanol (30 mL×3). The organic phases were combined, washed with saturated sodium chloride solution, dried over anhydrous sodium sulfate, and filtered. The filtrate was concentrated under reduced pressure, and the residue was purified by thin layer chromatography with elution system A to obtain the title compound 1-((6-(2-cyanoethyl)quinolin-4-yl)thio)cyclobutanecarboxylic acid 29 (5 mg, a white solid), yield: 11%.

MS m/z (ESI): 313.1 [M+1]

$^1$H NMR (400 MHz, CD3OD) δ 8.59 (d, 1H), 7.98 (d, 1H), 7.73 (d, 1H), 7.60 (d, 1H), 7.42 (d, 1H), 3.53 (t, 2H), 2.98-3.04 (m, 2H), 2.87 (t, 2H), 2.20-2.27 (m, 3H), 2.02-2.08 (m, 1H)

Example 30

1-((6-methylquinolin-4-yl)thio)cyclobutanecarboxylic acid

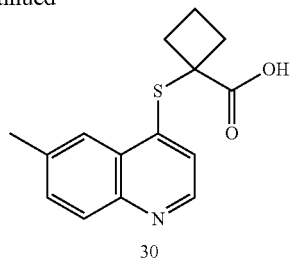

Step 1

Ethyl 1-((6-methylquinolin-4-yl)thio)cyclobutanecarboxylate

Ethyl 1-((6-bromoquinolin-4-yl)thio)cyclobutanecarboxylate 3c (200 mg, 0.55 mmol), trimethylboroxine (69 mg, 0.55 mmol), tetrakis(triphenylphosphine)palladium (64 mg, 0.06 mmol) and potassium carbonate (228 mg, 1.65 mmol) were added to 5 mL of a mixture of 1,4-dioxane and water (V:V=4:1). Upon completion of the addition, the reaction solution was heated to 110° C. and stirred for 16 hours. The reaction solution was filtered, and the filter cake was washed with dichloromethane (10 mL×2). The filtrate was combined and concentrated under reduced pressure. The residue was purified by thin layer chromatography with elution system C to obtain the title compound ethyl 1-((6-methylquinolin-4-yl)thio)cyclobutanecarboxylate 30a (6 mg, a yellow solid), yield: 6%.

MS m/z (ESI): 302.1 [M+1]

Step 2

1-((6-methylquinolin-4-yl)thio)cyclobutanecarboxylic acid

Ethyl 1-((6-methylquinolin-4-yl)thio)cyclobutanecarboxylate 30a (6 mg, 0.02 mmol) and lithium hydroxide monohydrate (2 mg, 0.04 mmol) were dissolved in 6 mL of a mixture of tetrahydrofuran, methanol and water (V:V:V=4:1:1). The reaction solution was stirred for 16 hours, added dropwise with 1 M hydrochloric acid to adjust the pH to 5~6, followed by addition of 10 mL of dichloromethane. The organic phase was separated, and the aqueous phase was extracted with dichloromethane (10 mL×2). The organic phases were combined, washed with saturated sodium chloride solution, dried over anhydrous sodium sulfate, and filtered. The filtrate was concentrated under reduced pressure, and the residue was purified by thin layer chromatography with elution system A to obtain the title compound 1-((6-methylquinolin-4-yl)thio)cyclobutanecarboxylic acid 30 (3 mg, a yellow solid), yield: 56%.

MS m/z (ESI): 274.2 [M+1]

$^1$H NMR (400 MHz, DMSO) δ 13.18 (s, 1H), 8.48-8.53 (m, 1H), 7.80-7.87 (m, 2H), 7.55-7.60 (m, 1H), 7.42-7.46 (m, 1H), 2.79-2.92 (m, 2H), 2.12-2.19 (m, 2H), 1.97-2.04 (m, 1H), 1.85-1.94 (m, 1H), 1.24 (s, 3H)

Example 31

1-((7-bromoquinolin-4-yl)thio)cyclobutanecarboxylic acid

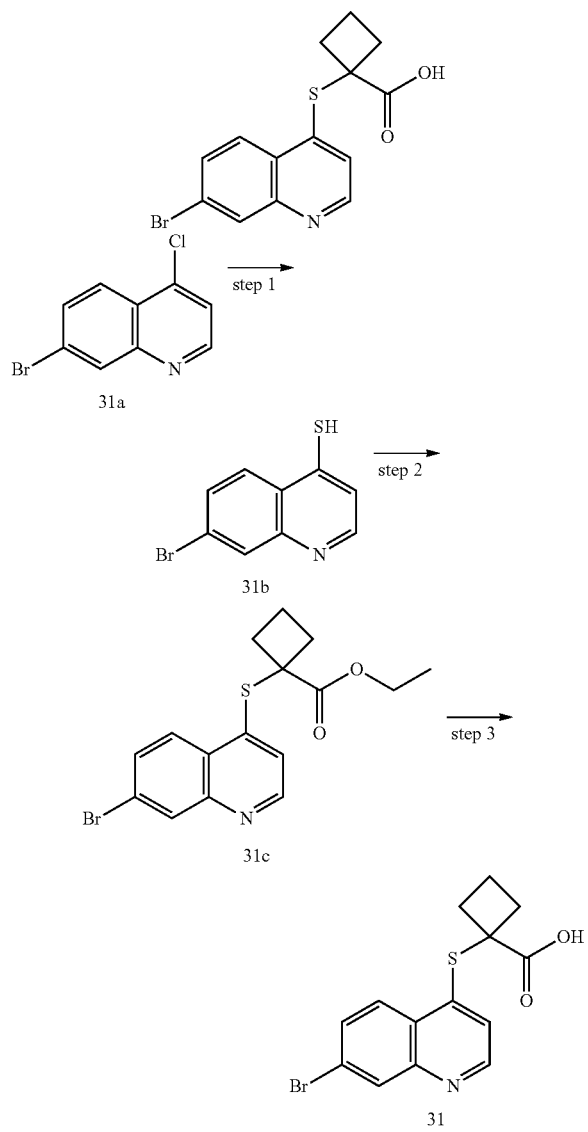

Step 1

7-bromoquinoline-4-thiol 7-bromo-4-chloroquinoline 31a (220 mg, 0.90 mmol) and sodium sulfide (212 mg, 2.70 mmol) were added to 10 mL of N,N-dimethylformamide. The reaction was heated to 80° C. and stirred for 2 hours. The reaction solution was concentrated under reduced pressure, mixed with 50 mL of water, followed by dropwise addition of 1 M hydrochloric acid to adjust the pH to 5~6, and extraction with ethyl acetate (50 mL×3). The organic phases were combined, washed with saturated sodium chlorine solution, dried over anhydrous sodium sulfate, and filtered. The filtrate was concentrated under reduced pressure to obtain the crude title compound 7-bromoquinoline-4-thiol 31b (220 mg, a yellow solid), which was used directly in the next step.

Step 2

Ethyl 1-((7-bromoquinolin-4-yl)thio)cyclobutanecarboxylate 7-bromoquinoline-4-thiol 31b (220 mg, 0.90 mmol), ethyl 1-bromocyclobutanecarboxylate (227 mg, 1.10 mmol) and cesium carbonate (896 mg, 2.70 mmol) were added to 5 mL of NA-dimethylformamide, successively. The reaction solution was heated to 60° C. and stirred for 2 hours, then mixed with 50 mL of water, stirred uniformly, and extracted with ethyl acetate (50 mL×3). The organic phases were combined, washed with saturated sodium chloride solution, dried over anhydrous sodium sulfate, and filtered. The filtrate was concentrated under reduced pressure, and the residue was purified by thin layer chromatography with elution system C to obtain the title compound ethyl 1-((7-bromoquinolin-4-yl)thio)cyclobutanecarboxylate 31c (100 mg, a colorless oil) yield: 30%.

MS m/z (ESI): 368.1 [M+1]

Step 3

((7-bromoquinolin-4-yl)thio)cyclobutanecarboxylic acid

Ethyl 1-((7-bromoquinolin-4-yl)thio)cyclobutanecarboxylate 31c (100 mg, 0.27 mmol) and lithium hydroxide monohydrate (34 mg, 0.82 mmol) were dissolved in 6 mL of a mixture of tetrahydrofuran, methanol and water (V:V:V=4:1:1). The reaction solution was stirred for 16 hours, then concentrated under reduced pressure, and mixed with 50 mL of water, followed by dropwise addition of 1 M hydrochloric acid to adjust the pH to 5~6, and extraction with ethyl acetate (50 mL×3). The organic phases were combined, washed with saturated sodium chloride solution, dried over anhydrous sodium sulfate, and filtered. The filtrate was concentrated under reduced pressure, and the residue was recrystallized from diethyl ether to obtain the title compound 1-((7-bromoquinolin-4-yl)thio)cyclobutanecarboxylic acid 31 (20 mg, a yellow solid), yield: 22%.

MS m/z (ESI): 338.0 [M+1]

$^1$H NMR (400 MHz, DMSO) δ 8.73 (d, 1H), 8.22 (s, 1H), 8.04 (d, 1H), 7.79 (d, 1H), 7.22 (s, 1H), 2.87-2.94 (m, 2H), 2.30-2.35 (m, 2H), 2.22-2.28 (m, 1H), 1.99-2.02 (m, 1H)

Example 32

1-((6-bromoquinolin-4-yl)thio)cyclopentanecarboxylic acid

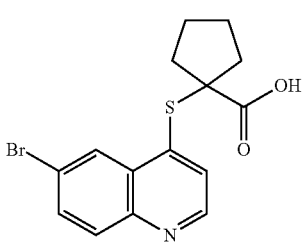

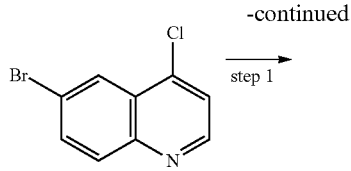

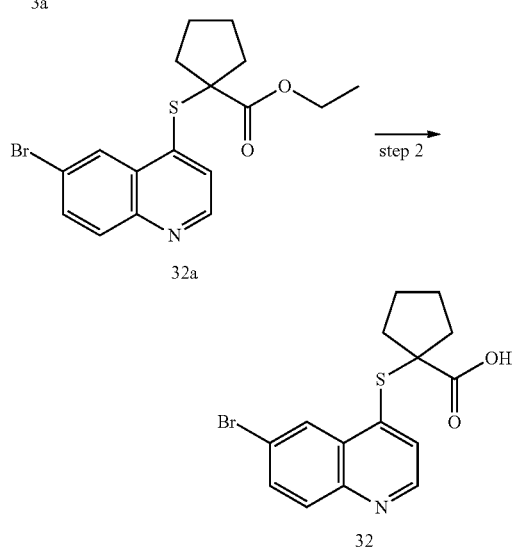

Step 1

Ethyl 1-((6-bromoquinolin-4-yl)thio)cyclopentanecarboxylate 6-bromo-4-chloroquinoline 3a (203 mg, 0.84 mmol, prepared by a well known method disclosed in "*Bioorganic & Medicinal Chemistry Letters*, 2012, 22 (4), 1569-1574") was added to 10 mL of N,N-dimethylformamide. Sodium sulfide (88 mg. 1.00 mmol) was grinded and added to the reaction solution. Upon completion of the addition, the reaction solution was heated to 80° C. and stirred for 2 hours. After stopping heating, the reaction solution was cooled down to 50° C., ethyl 1-bromocyclopentanecarboxylate (241 mg, 1.09 mmol) and cesium carbonate (821 mg, 2.52 mmol) were added. Upon completion of the addition, the reaction solution was stirred for a further 16 hours at 40° C. After stopping heating, the reaction solution was mixed with 30 mL of dichloromethane, stirred uniformly, filtered through celite after, and washed with dichloromethane. The filtrate was combined, concentrated under reduced pressure, and the residue was purified by silica gel column chromatography with elution system A to obtain the title compound ethyl 1-((6-bromoquinolin-4-yl)thio)cyclopentanecarboxylate 32a (118 mg, a purple oil), yield: 37.0%.

MS m/z (ESI): 380.1 [M+1]

Step 2

1-((6-bromoquinolin-4-yl)thio)cyclopentanecarboxylic acid

Ethyl 1-((6-bromoquinolin-4-yl)thio)cyclopentanecarboxylate 32a (110 mg, 0.29 mmol) was added to 14 mL of a mixture of tetrahydrofuran, ethanol and water (V:V:V=4:1:2), followed by addition of lithium hydroxide monohydrate (37 mg, 0.87 mmol). The reaction was stirred for 1 hour, then mixed with 2 mL sodium hydroxide solution (4N), and stirred for a further 1 hour. The reaction solution was mixed with 50 mL of water, and left to stand and separate. The aqueous phase was washed with 20 mL ethyl acetate, added dropwise with hydrochloric acid (1N) to adjust the pH to 3~4, and extracted with ethyl acetate (30 mL×2). The organic phases were combined, washed with saturated sodium chloride solution (30 mL), dried over anhydrous magnesium sulfate, and filtrated to remove the desiccant. The filtrate was concentrated under reduced pressure to obtain the title compound 1-((6-bromoquinolin-4-yl)thio)cyclopentanecarboxylic acid 32 (88 mg, a yellow solid), yield: 88%.

MS m/z (ESI): 352.1 [M+1]

$^1$H NMR (400 MHz, DMSO) δ 12.76 (s, 1H), 8.81 (d, 1H), 8.29-8.40 (m, 1H), 7.95-8.03 (m, 1H), 7.88-7.95 (m, 1H), 7.49 (d, 1H), 2.42 (d, 2H), 1.94-2.05 (m, 2H), 1.78-1.89 (m, 2H), 1.65-1.78 (m, 2H)

Example 33

1-((6-bromoquinolin-4-yl)thio)cyclopropanecarboxylic acid

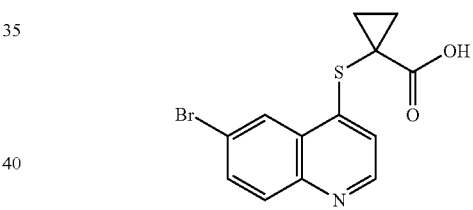

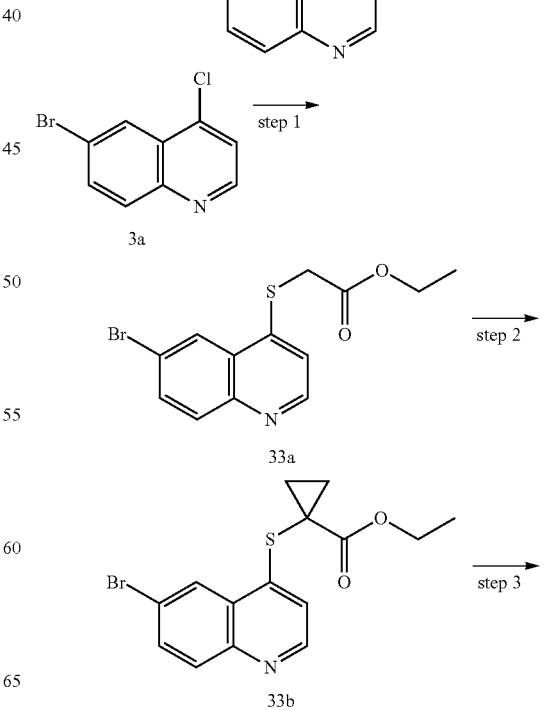

-continued

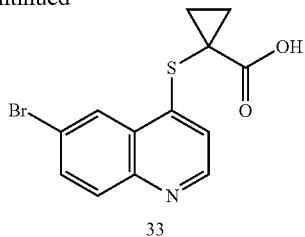
33

Step 1

Ethyl 2-((6-bromoquinolin-4-yl)thio)acetate 6-bromo-4-chloroquinoline 3a (628 mg, 2.59 mmol, prepared by a well known method disclosed in "*Bioorganic & Medicinal Chemistry Letters,* 2012, 22 (4), 1569-1574") was added to 20 mL of N,N-dimethylformamide. Sodium sulfide (242 mg, 3.11 mmol) was grinded and added to the reaction solution. Upon completion of the addition, the reaction solution was heated to 80° C. and stirred for 1 hour. After stopping heating, the reaction solution was cooled down to 50° C., and ethyl bromoacetate (563 mg, 3.37 mmol) and cesium carbonate (2.53 g, 7.77 mmol) were added. Upon completion of the addition, the reaction solution was stirred for a further 6 hours at 40° C. After stopping heating, the reaction solution was concentrated under reduced pressure, and the residue was purified by silica gel column chromatography with eluent systems A to obtain the title compound ethyl 2-((6-bromoquinolin-4-yl)thio)acetate 33a (658 mg, a yellow solid), yield: 78%.

MS m/z (ESI): 326.0 [M+1]

Step 2

Ethyl 1-((6-bromoquinolin-4-yl)thio)cyclopropanecarboxylate

Ethyl 2-((6-bromoquinolin-4-yl)thio)acetate 33a (440 mg, 1.35 mmol) was added to 5 mL of N,N-dimethylformamide, followed by addition of potassium carbonate (467 mg, 3.37 mmol), 1,2-dibromoethane (330 mg, 1.75 mmol) and tetrabutylammonium bromide (25 mg, 0.07 mmol). Upon completion of the addition, the reaction solution was heated to 50° C. and stirred for 16 hours. The reaction solution was concentrated under reduced pressure, and the residue was mixed with 100 mL of water and 30 mL of ethyl acetate, stirred uniformly, and left to stand and separate. The organic phase was washed with saturated sodium chloride solution (20 mL), dried over anhydrous magnesium sulfate, and filtered to remove the desiccant. The filtrate was concentrated under reduced pressure, and the residue was separated by HPLC to obtain the title compound ethyl 1-((6-bromoquinolin-4-yl)thio)cyclopropanecarboxylate 33b (57 mg, a off-white solid), which was used directly in the next step.

MS m/z (ESI): 352.1 [M+1]

Step 3

1-((6-bromoquinolin-4-yl)thio)cyclopropanecarboxylic acid

Ethyl 1-((6-bromoquinolin-4-yl)thio)cyclopropanecarboxylate 33b (55 mg, 0.16 mmol) was added to 7 mL of a mixture of tetrahydrofuran, ethanol and water (V:V:V=4:1:2), followed by addition of lithium hydroxide monohydrate (33 mg, 0.78 mmol). Upon completion of the addition, the reaction was stirred for 16 hours. The reaction solution was added dropwise with 1 M hydrochloric acid to adjust the pH<3, and concentrated under reduced pressure. The residue was dissolved in 30 mL of methanol, concentrated under reduced pressure again, and 20 mL of dichloromethane was added to the residue. Upon completion of the addition, the resulting solution was stirred for 10 minutes, and filtered. The filtrate was concentrated under reduced pressure to obtain the title compound 1-((6-bromoquinolin-4-yl)thio)cyclopropanecarboxylic acid 33 (20 mg, a yellow solid), yield: 40%.

MS m/z (ESI): 324.0 [M+1]

$^1$H NMR (400 MHz, DMSO) δ 8.90 (d, 1H), 8.16-8.25 (m, 2H), 8.05-8.15 (m, 1H), 7.63 (d, 1H), 1.90-1.96 (m, 2H), 1.43-1.52 (m, 2H)

TEST EXAMPLES

Biological Evaluation

Test Example 1

Assay for Determining the Activity of the Compounds of the Present Invention for Inhibiting URAT1

In vitro URAT1 assay can be used to identify compounds having potential activity for decreasing serum uric acid. In a suitable test, the vectors that encode human URAT1 (URAT1 cDNA: Guangzhou Copoeia EX-T4563-M02) were used to transfect cells (human embryonic kidney cells, HEK293: Cell Bank of the Chinese Academy of Sciences, GNHu18). The transfected cells—HEK293/hURAT1 cells—were obtained, then their uptake ability of radiolabeled uric acid was determined. The activity of the compounds as URAT1 inhibitors can be evaluated by the ability of the compounds to block the uptake of uric acid in the transfected cells.

The HEK293/hURAT1 cells in Eagle's minimal essential medium (EMEM) were inoculated in a 48-well plate that was coated with poly-D-lysine (Becton Dickinson, Catalog No. 356509), with an inoculation density of $10^5$ cells/well, and incubated overnight. A reaction solution containing $^{14}$C— uric acid (American Radioactive Compound, Catalog No. ARC 0513A) with a final concentration of 11.57 µM was prepared by the use or non-use of the test compounds in Hanks balanced salt solution (HBSS). The Hanks balanced salt solution (HBSS) contained 125 mM sodium gluconate, 4.8 mM potassium gluconate, 1.2 mM potassium dihydrogen phosphate, 1.2 mM magnesium sulfate, 1.3 mM calcium gluconate, 5.6 mM glucose and 25 mM HEPES (pH 7.3). After the medium was washed with the wash buffer (125 mM sodium gluconate, 10 mM HEPES, pH 7.3) for one time, the reaction solution prepared from the above step was added to each well and incubated at room temperature for 12 minutes. Then the reaction solution was removed, the cells were washed twice with the wash buffer and lysed with 0.2 M NaOH for 5 minutes. The cell lysate was transferred to a 96-well culture plate with a scintillation fluid (PerkinElmer, Catalog No. 1450-401), and counting of radioactivity was carried out on a Microbeta counter (PerkinElmer).

The test compounds were dissolved in DMSO, then DMSO with the same concentration was added to HEK293/hURAT1 cell wells without the test compounds. Cellular uptake of uric acid under various test conditions was expressed as average percentage inhibition rates in comparison to DMSO control. Radioactive values from the wells containing DMSO were considered as 100% uptake of the cells. $IC_{50}$ values were calculated from the data of the inhibition rates at various concentrations.

The above assay was used to determine the biochemical activity of the compounds of the present invention for inhibiting hURAT1. $IC_{50}$ values are shown in Table 1.

TABLE 1

$IC_{50}$ (nM) of the compounds of the present invention for inhibiting the activity of hURAT1

| Example No. | hURAT1 $IC_{50}$(nM) |
|---|---|
| 1 | 251 |
| 2 | 61 |
| 3 | 19 |
| 4 | 343 |
| 5 | 207 |
| 6 | 332 |
| 7 | 159 |
| 8 | 359 |
| 9 | 197 |
| 10 | 926 |
| 12 | 557 |
| 13 | 164 |
| 17 | 398 |
| 22 | 115 |
| 23 | 658 |
| 24 | 680 |
| 30 | 343 |
| 31 | 129 |
| 32 | 352 |
| 33 | 324 |

Conclusion: The compounds of the present invention had significant activity for inhibiting hURAT1.

Pharmacokinetics Assay

Test Example 2

Pharmacokinetics Assay of the Compounds of Example 1, Example 2 and Example 3 of the Present Invention 1. Abstract Sprague-Dawley (SD) rats were used as test animals. The compounds of Example 1, Example 2 and Example 3 were administered intragastrically to rats to determine the drug concentration in plasma at different time points by a LC/MS/MS method. The pharmacokinetic behavior of the compounds of the present invention was studied and evaluated in rats.

2. Protocol
2.1 Samples
Compounds of Example 1, Example 2 and Example 3.
2.2 Test Animals
12 Healthy adult SD rats, half male and half female, purchased from SINO-BRITSH SIPPR/BK LAB. ANIMAL LTD., CO, Certificate No.: SCXK (Shanghai) 2008-0016, were divided into three groups, with 4 rats in each group.

2.3 Preparation of the Test Compounds

The appropriate amounts of test compounds were weighed and mixed with 0.5% CMC-Na to prepare a 0.3 mg/mL suspension by an ultrasonic method.

2.4 Administration

After an overnight fast, 12 SD rats, half male and half female, were divided into 3 groups, with 4 rats in each group, and administered the compounds intragastrically at a dose of 3.0 mg/kg and an administration volume of 10 mL/kg.

3. Process

Blood samples (0.1 mL) were taken from the orbital sinus before administration, and at 0.5 h, 1 h, 2 h, 4 h, 6 h, 8 h, 11 h, 24 h and 48 h after administration, stored in heparinized tubes, and centrifuged for 10 minutes at 3,500 rpm to separate blood plasma. The plasma samples were stored at $-20°$ C.

The concentration of the test compounds in rat plasma after intragastrically administering the test compounds was analyzed by a LC-MS/MS method. The linearity range of the method is 2.0-5000 ng/ml, and the lower limit of quantification is 2.00 ng/ml. Plasma samples were analyzed after protein precipitation.

4. Results of Pharmacokinetic Parameters

Pharmacokinetic Parameters of the compounds of the present invention were shown as follows:

| | Pharmacokinetics Assay (3.0 mg/kg) | | | | | |
|---|---|---|---|---|---|---|
| Example No. | Plasma Conc. Cmax (ng/mL) | Area Under Curve AUC (ng/mL*h) | Half-Life $T\frac{1}{2}$ (h) | Mean Residence Time MRT (h) | Clearance CL/F (ml/min/kg) | Apparent Distribution Volume Vz/F (ml/kg) |
| 1 | 8795 ± 1760 | 20718 ± 5266 | 2.84 ± 0.65 | 3.15 ± 0.82 | 2.54 ± 0.68 | 652 ± 333 |
| 2 | 2708 ± 919 | 38190 ± 25141 | 8.83 ± 4.04 | 12.9 ± 5.8 | 1.95 ± 1.31 | 1214 ± 674 |
| 3 | 3470 ± 854 | 28374 ± 8544 | 5.35 ± 1.12 | 8.15 ± 1.30 | 1.89 ± 0.59 | 878 ± 335 |

Conclusion: The compounds of the present invention had good pharmacokinetic absorption and significant advantage of oral absorption.

What is claimed is:

1. A compound of formula (I), or a tautomer, mesomer, racemate, enantiomer, or diastereomer thereof, or mixture thereof, or a pharmaceutically acceptable salt thereof:

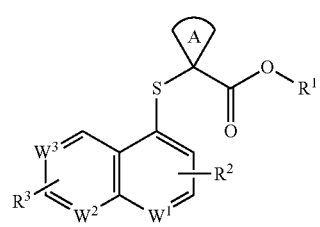

(I)

wherein:
ring A is cycloalkyl;
$W^1$ is N;
$W^2$ is $CR^b$, wherein $R^b$ is selected from the group consisting of hydrogen and alkyl;
$W^3$ is $CR^c$;
$R^c$ is selected from the group consisting of hydrogen, halogen, cyano, nitro, alkyl, alkenyl, alkynyl, cycloalkyl, heterocyclyl, aryl, heteroaryl, —OR⁴, —S(O)$_m$R⁴, —C(O)R⁴, —C(O)OR⁴, —C(O)NR⁵R⁶, —NR⁵R⁶ and —NR⁵C(O)R⁶, wherein the alkyl, alkenyl, alkynyl, cycloalkyl, heterocyclyl, aryl and heteroaryl are each independently optionally substituted with one or more groups selected from the group consisting of halogen, cyano, nitro, oxo, alkyl, haloalkyl, hydroxyalkyl, alkenyl, alkynyl, cycloalkyl, heterocyclyl, aryl, heteroaryl, —OR⁴, —S(O)$_m$R⁴, —C(O)R⁴, —C(O)OR⁴, —C(O)NR⁵R⁶, —NR⁵R⁶ and —NR⁵C(O)R⁶;

R¹ is hydrogen or alkyl;

R² and R³ are each independently selected from the group consisting of hydrogen, halogen, cyano, nitro, alkyl, haloalkyl and hydroxyalkyl;

R⁴ is selected from the group consisting of hydrogen, alkyl, halogen, cycloalkyl, heterocyclyl, aryl and heteroaryl, wherein the alkyl, cycloalkyl, heterocyclyl, aryl and heteroaryl are each independently optionally substituted with one or more groups selected from the group consisting of halogen, cyano, nitro, hydroxy, oxo, alkyl, haloalkyl, hydroxyalkyl, alkoxy, cycloalkyl, heterocyclyl, aryl, heteroaryl, carboxyl, alkoxycarbonyl, —C(O)NR⁵R⁶, —NR⁵R⁶ and —NR⁵C(O)R⁶;

R⁵ and R⁶ are each independently selected from the group consisting of hydrogen, alkyl, cycloalkyl, heterocyclyl, aryl and heteroaryl; and m is 0, 1, or 2.

2. The compound of formula (I), or the tautomer, mesomer, racemate, enantiomer, or diastereomer thereof, or mixture thereof, or the pharmaceutically acceptable salt thereof according to claim 1, wherein ring A is cyclopropyl, cyclobutyl or cyclopentyl.

3. The compound of formula (I), or the tautomer, mesomer, racemate, enantiomer, or diastereomer thereof, or mixture thereof, or the pharmaceutically acceptable salt thereof according to claim 1, wherein R$^c$ is selected from the group consisting of hydrogen, halogen, cyano, alkyl, cycloalkyl, aryl, —OR⁴, —NR⁵R⁶ and —NR⁵C(O)R⁶, wherein the alkyl, cycloalkyl and aryl are each independently optionally substituted with one or more groups selected from the group consisting of halogen, cyano, nitro, oxo, alkyl, haloalkyl, hydroxyalkyl, cycloalkyl and heterocyclyl.

4. The compound of formula (I), or the tautomer, mesomer, racemate, enantiomer, or diastereomer thereof, or mixture thereof, or the pharmaceutically acceptable salt thereof according to claim 1, wherein R$^c$ is selected from the group consisting of hydrogen, halogen, alkyl and haloalkyl.

5. The compound of formula (I), or the tautomer, mesomer, racemate, enantiomer, or diastereomer thereof, or mixture thereof, or the pharmaceutically acceptable salt thereof according to claim 1, wherein R² is hydrogen.

6. The compound of formula (I), or the tautomer, mesomer, racemate, enantiomer, or diastereomer thereof, or mixture thereof, or the pharmaceutically acceptable salt thereof according to claim 1, wherein R³ is hydrogen or halogen.

7. The compound of formula (I), or the tautomer, mesomer, racemate, enantiomer, or diastereomer thereof, or mixture thereof, or the pharmaceutically acceptable salt thereof according to claim 1, being a compound of formula (II) or a tautomer, mesomer, racemate, enantiomer, or diastereomer thereof, or mixture thereof, or a pharmaceutically acceptable salt thereof:

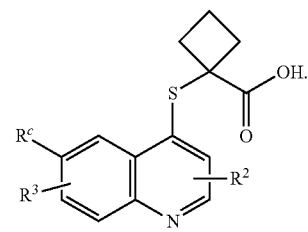

(II)

8. The compound of formula (I), or the tautomer, mesomer, racemate, enantiomer, or diastereomer thereof, or mixture thereof, or the pharmaceutically acceptable salt thereof according to claim 1, being a compound of formula (III) or a tautomer, mesomer, racemate, enantiomer, or diastereomer thereof, or mixture thereof, or a pharmaceutically acceptable salt thereof:

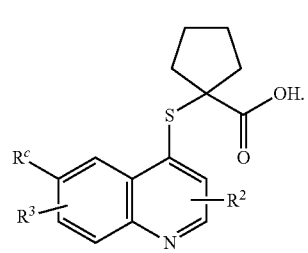

(III)

9. The compound of formula (I), or the tautomer, mesomer, racemate, enantiomer, or diastereomer thereof, or mixture thereof, or the pharmaceutically acceptable salt thereof according to claim 1, being a compound of formula (IV) or a tautomer, mesomer, racemate, enantiomer, or diastereomer thereof, or mixture thereof, or a pharmaceutically acceptable salt thereof:

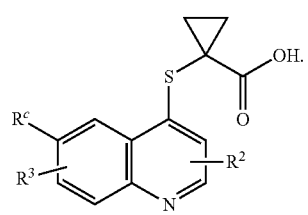

(IV)

10. The compound of formula (I), or the tautomer, mesomer, racemate, enantiomer, or diastereomer thereof, or mixture thereof, or the pharmaceutically acceptable salt thereof according to claim 1, wherein the compound is selected from the group consisting of:

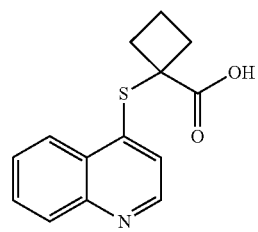

-continued
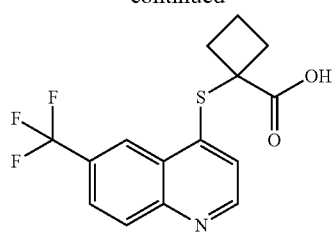
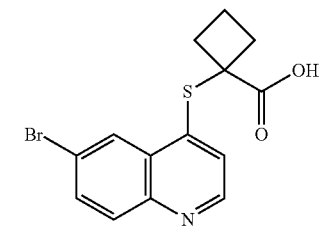
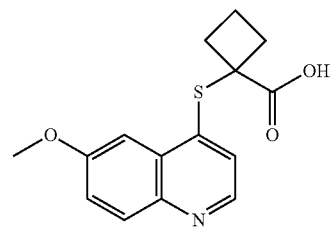
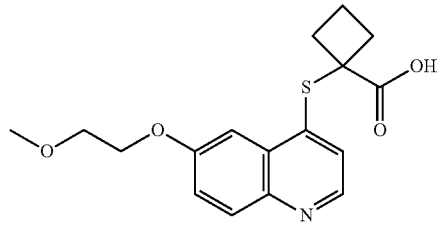
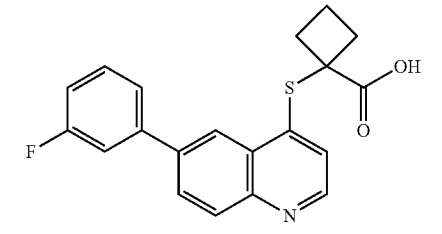
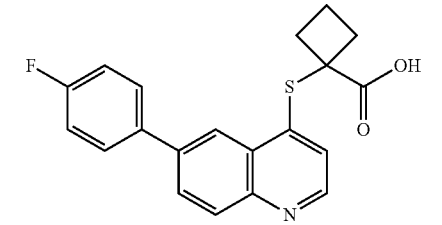
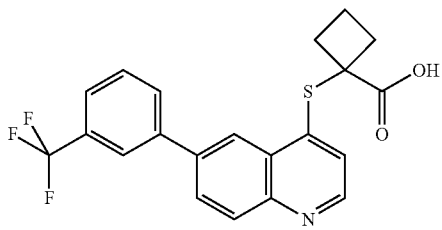
-continued
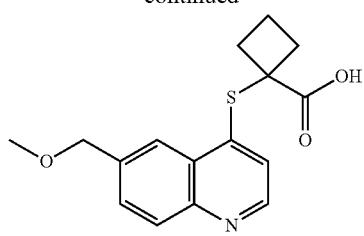
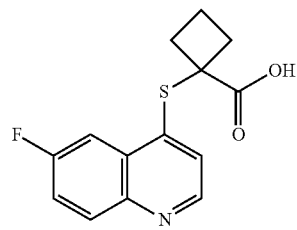
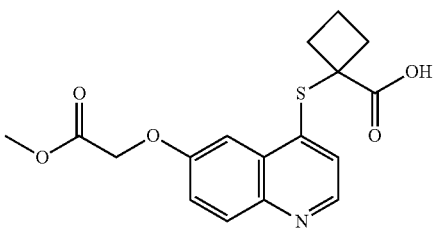
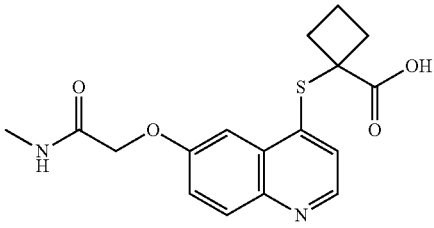
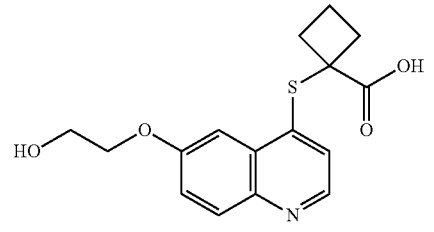
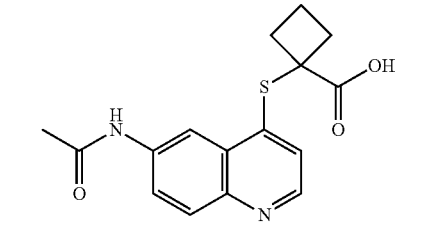
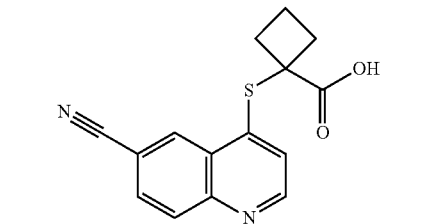

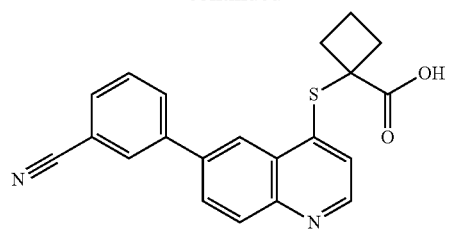
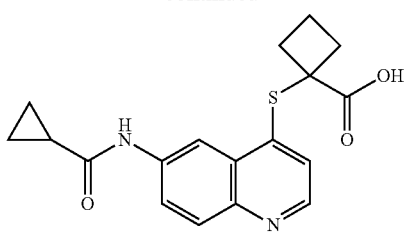
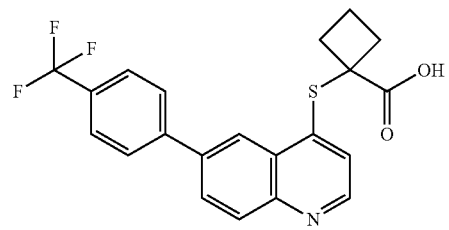
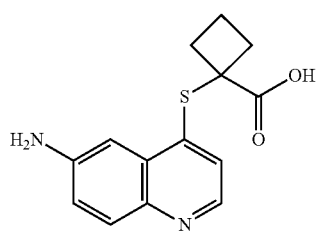 [SMILES: Nc1ccc2nccc(SC3(C(=O)O)CCC3)c2c1]
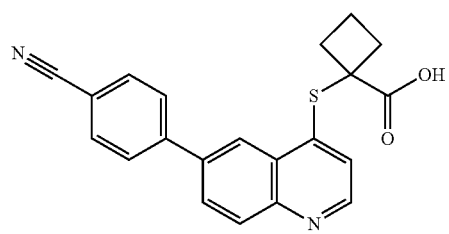
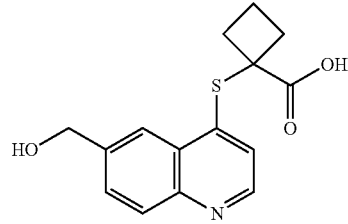
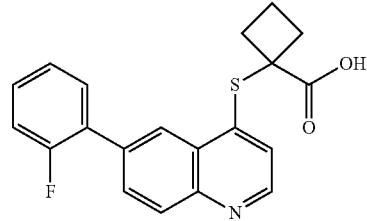
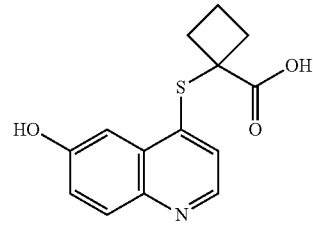
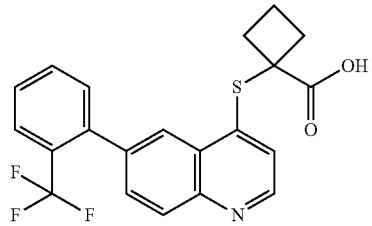
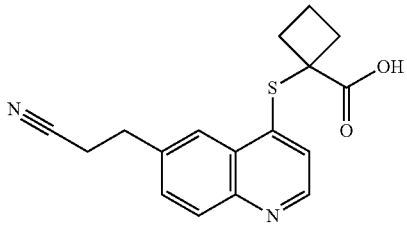
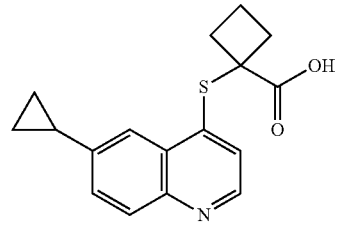
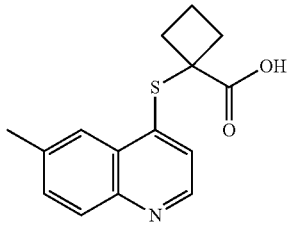
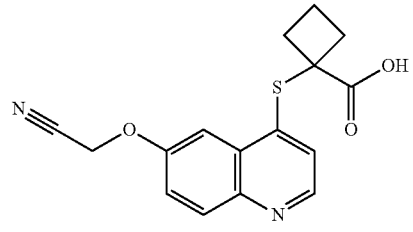
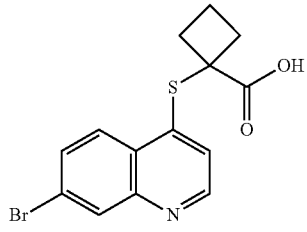

-continued
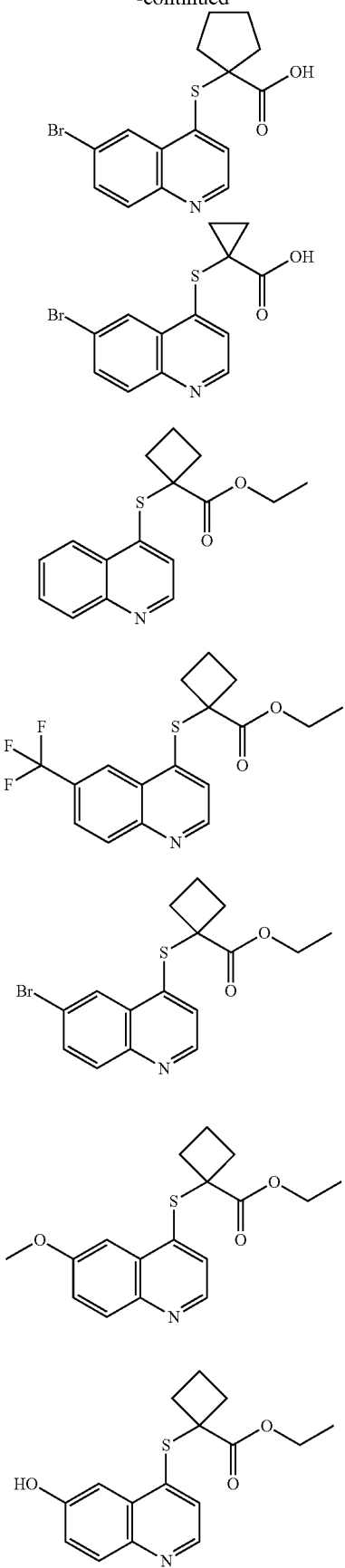
-continued
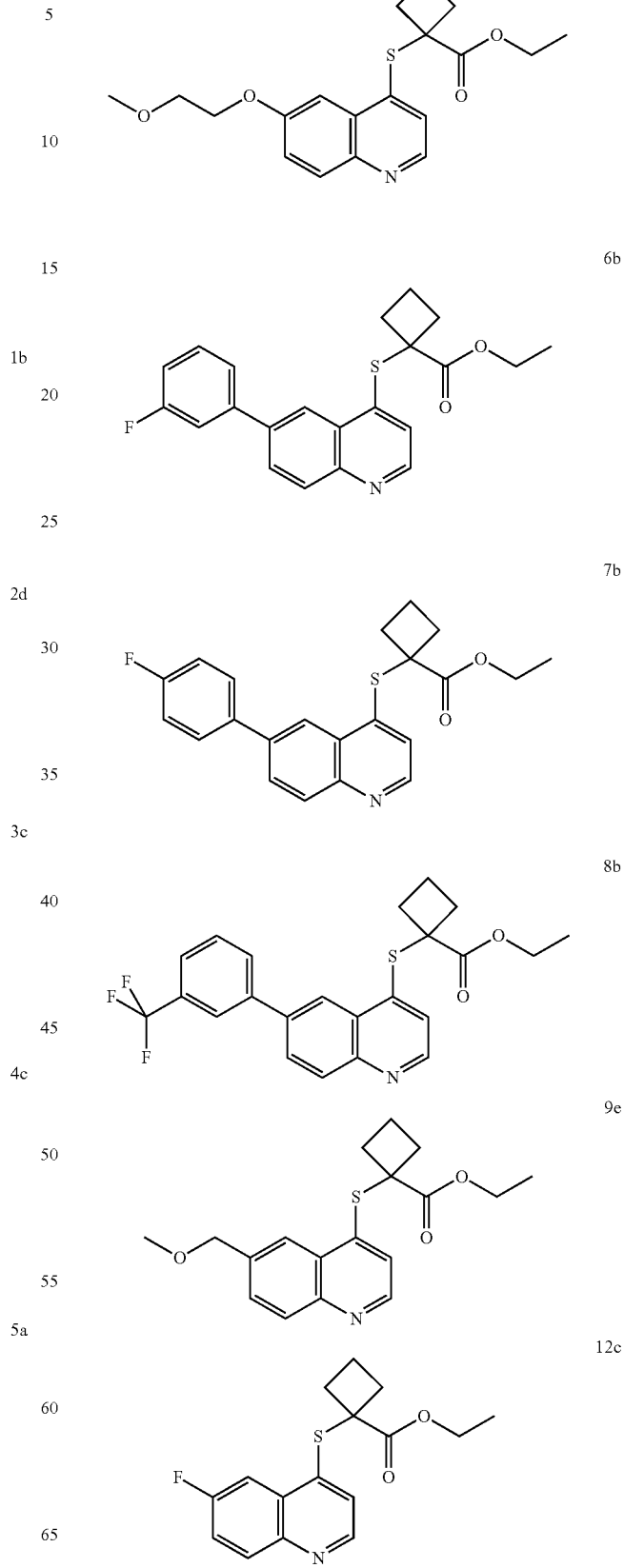

| | |
|---|---|
| 13a 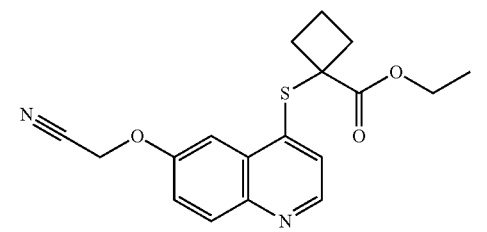 | 20b 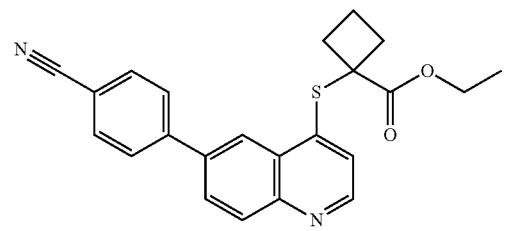 |
| 14a 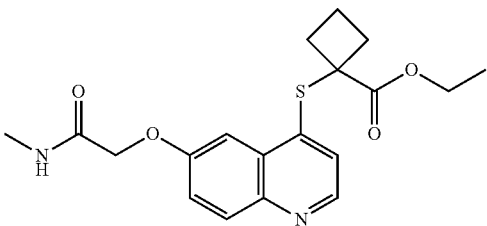 | 21b 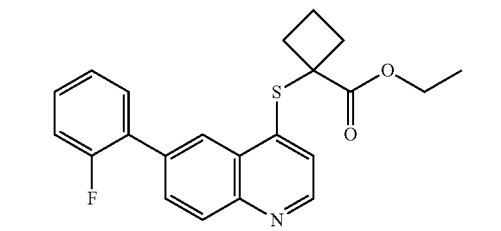 |
| 15a 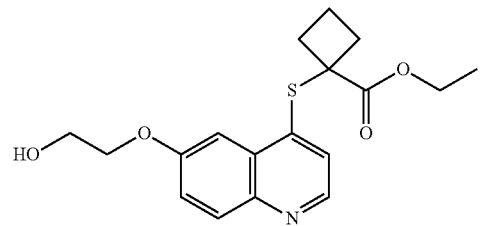 | 22b 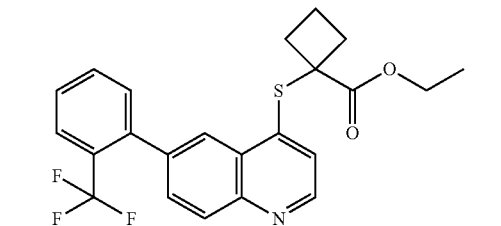 |
| 16c 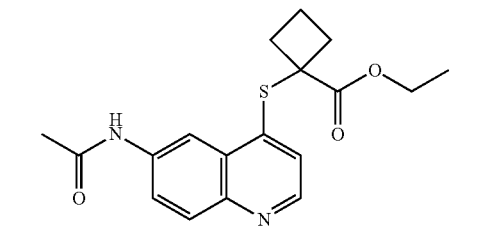 | 23b 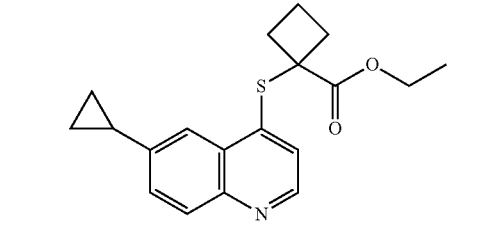 |
| 17a 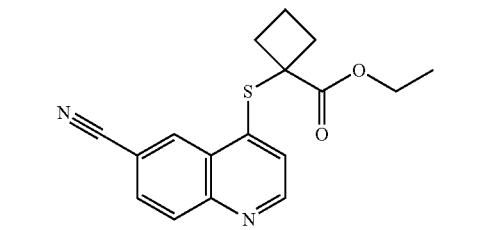 | 25b 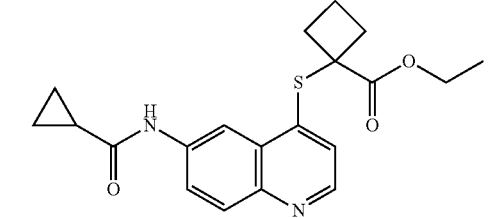 |
| 18b 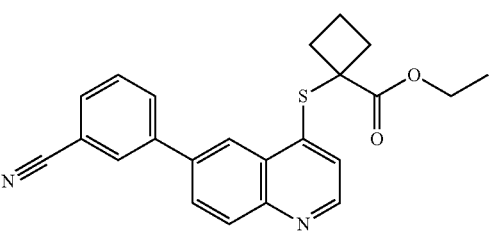 | 27b 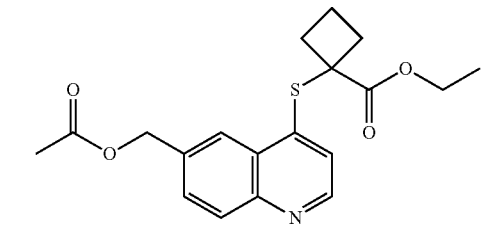 |
| 19b 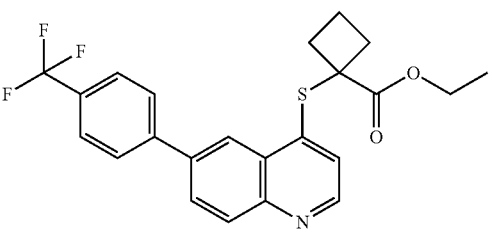 | 29f 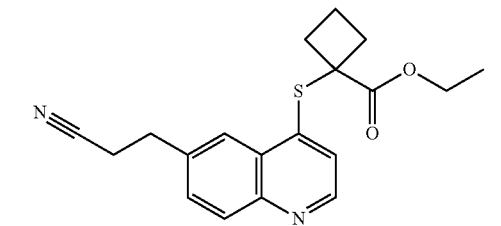 |

-continued

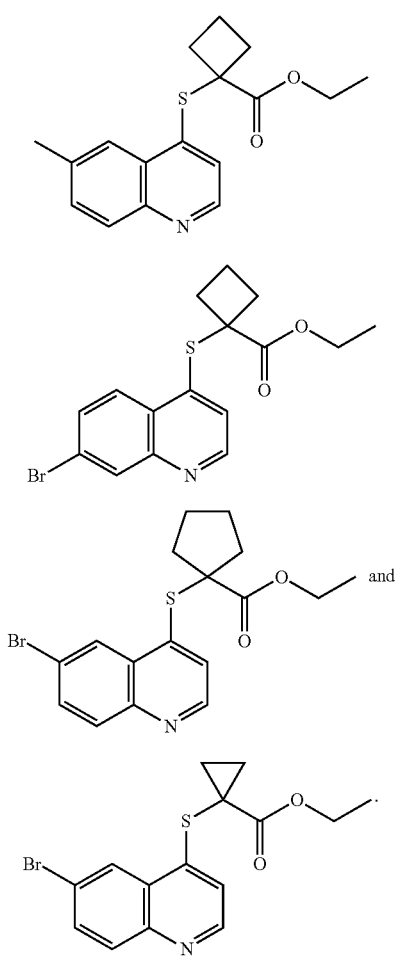

30a

31c

32a

33b

11. A process of preparing the compound of formula (I) according to claim 1, or the tautomer, mesomer, racemate, enantiomer, or diastereomer thereof, or mixture thereof, or the pharmaceutically acceptable salt thereof, comprising a step of:

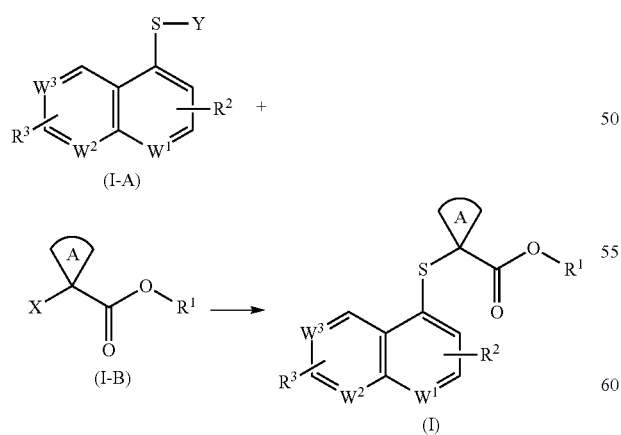

reacting a compound of formula (IA) with a compound of formula (IB) via a substitution reaction, and optionally hydrolyzing the resulting product under an alkaline condition to obtain the compound of formula (I);

wherein: X is a leaving group; and Y is a hydrogen or sodium atom.

12. A compound of formula (I-A), or a tautomer, mesomer, racemate, enantiomer, or diastereomer thereof, or mixture thereof, or a pharmaceutically acceptable salt thereof:

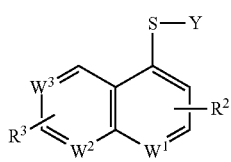

(I-A)

wherein:
Y is a hydrogen or sodium atom;
$W^1$ is N;
$W^2$ is $CR^b$;
$W^3$ is $CR^c$;
$R^b$ is hydrogen;
$R^2$ and $R^3$ are each independently hydrogen;
$R^c$ is alkyl or alkoxy, wherein the alkyl and alkoxy are each independently substituted with one or more groups selected from the group consisting of cyano and —$OR^4$; and
$R^4$ is selected from the group consisting of hydrogen and alkyl.

13. The compound of formula (IA), or the tautomer, mesomer, racemate, enantiomer, or diastereomer thereof, or mixture thereof, or the pharmaceutically acceptable salt thereof according to claim 12, wherein the compound is selected from the group consisting of:

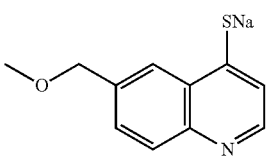

9d

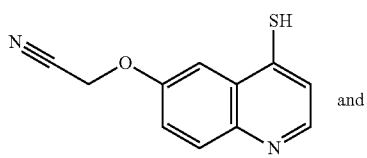

24c and

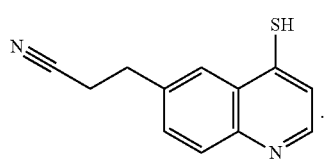

29e

14. A pharmaceutical composition comprising a therapeutically effective amount of the compound of formula (I), or the tautomer, mesomer, racemate, enantiomer, or diastereomer thereof, or mixture thereof, or the pharmaceutically acceptable salt thereof according to claim 1, and a pharmaceutically acceptable carrier, diluent or excipient.

15. The pharmaceutical composition according to claim 14, further comprising one or more additional uric-acid-lowering drugs selected from the group consisting of URAT1 inhibitors, xanthine oxidase inhibitors, xanthine dehydrogenase inhibitors, and xanthine oxidoreductase inhibitors.

16. A method for inhibiting URAT1, the method comprising a step of administering to a subject in need thereof the pharmaceutical composition according to claim 14.

17. A method for decreasing serum uric acid levels, the method comprising a step of administering to a subject in need thereof the pharmaceutical composition according to claim 14.

18. A method of treating a disease characterized by an abnormal uric acid level, the method comprising a step of administering to a subject in need thereof the pharmaceutical composition according to claim 14, wherein the disease is selected from the group consisting of gout and hyperuricemia.

19. The process according to claim 11, wherein X is halogen.

20. The pharmaceutical composition according to claim 15, wherein the one or more additional uric-acid-lowering drugs is allopurinol, febuxostat or topiroxostat.

* * * * *